(12) United States Patent
Brujic et al.

(10) Patent No.: US 8,315,821 B2
(45) Date of Patent: Nov. 20, 2012

(54) PACKING PROPERTIES OF PARTICULATE COMPOSITIONS

(75) Inventors: Jasna Brujic, New York, NY (US); Eric Corwin, Brooklyn, NY (US); Maxime Clusel, Grenoble (FR)

(73) Assignee: New York University, New York, NY (US)

( * ) Notice: Subject to any disclaimer, the term of this patent is extended or adjusted under 35 U.S.C. 154(b) by 368 days.

(21) Appl. No.: 12/686,036

(22) Filed: Jan. 12, 2010

(65) Prior Publication Data

US 2010/0211330 A1  Aug. 19, 2010

Related U.S. Application Data

(60) Provisional application No. 61/144,353, filed on Jan. 13, 2009.

(51) Int. Cl.
*G01N 31/00* (2006.01)
(52) U.S. Cl. ......................................... 702/30
(58) Field of Classification Search ........................ None
See application file for complete search history.

(56) References Cited

U.S. PATENT DOCUMENTS

| | | |
|---|---|---|
| 5,796,498 A | 8/1998 | French |
| 6,281,994 B1 | 8/2001 | Horikoshi et al. |
| 8,119,988 B2 * | 2/2012 | Daido et al. ............. 250/339.13 |

FOREIGN PATENT DOCUMENTS

| | | |
|---|---|---|
| CA | 1 159 674 A1 | 1/1984 |
| EP | 0 278 714 | 8/1988 |
| WO | WO 2008/127410 A2 | 10/2008 |
| WO | WO 2009/059008 A1 | 5/2009 |

OTHER PUBLICATIONS

Lee, Sang-Hyuk et al., "Holographic Microscopy of Holographically Trapped Three-Dimensional Structures", *Optics Express*, (2007) pp. 1505-1512, Optical Society of America.
International Search Report dated Apr. 30, 2010 for PCT/US2010/021045, 2 pages.
International Search Report dated Feb. 12, 2009 for PCT/US2008/081794, 1 page.

* cited by examiner

*Primary Examiner* — Aditya Bhat
(74) *Attorney, Agent, or Firm* — Foley & Lardner LLP

(57) ABSTRACT

A method and system for determining a packing property of a particulate composition. The method includes: obtaining size information relating to the particulate material; determining neighbor information from the size information; determining contact information from the size information; and determining a packing property from the neighbor information and the contact information, thereby enabling determination of the characteristic properties of the particulate composition. The method can be executed by use of a computer system to execute computer software instructions applied to data obtained on the particulate composition to determine a variety of properties of the particulate composition.

20 Claims, 53 Drawing Sheets

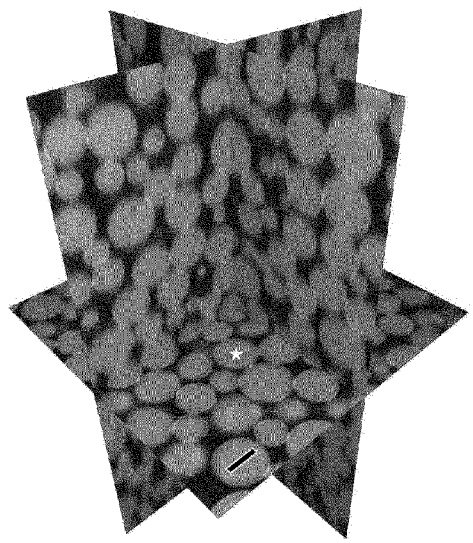
FIG. 1A
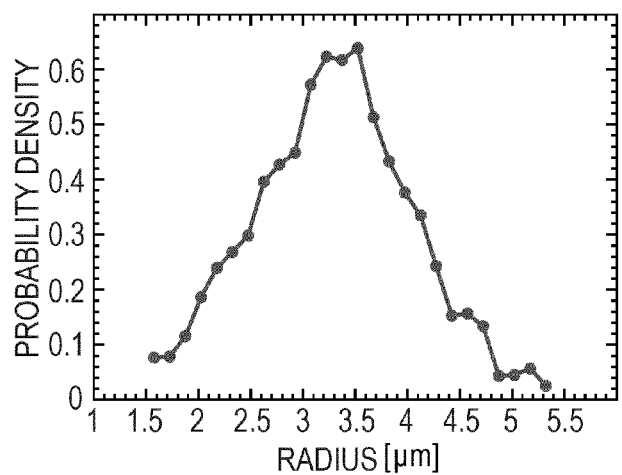
FIG. 1B
FIG. 1C(1)
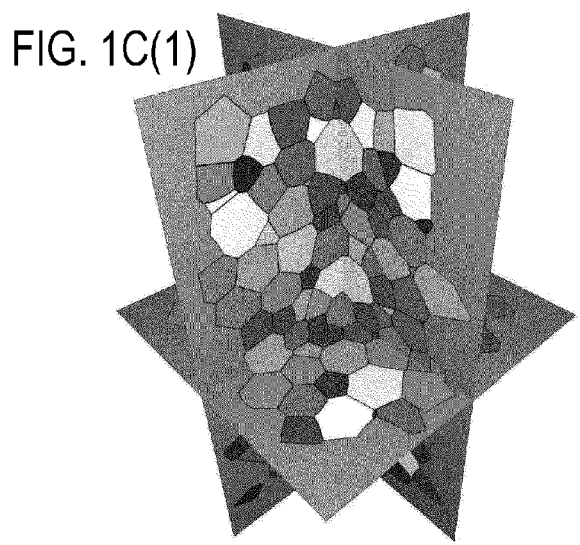
FIG. 1C(2)

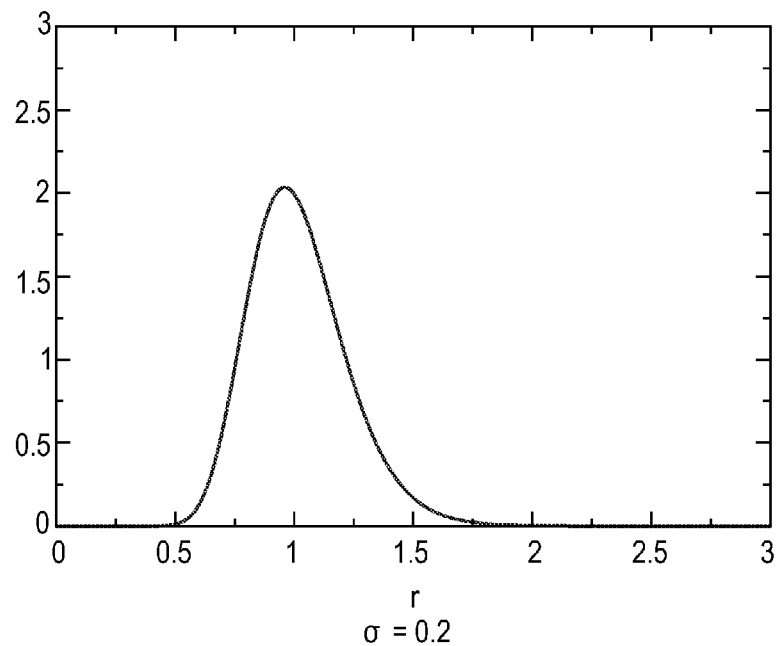
FIG. 11C σ = 0.2
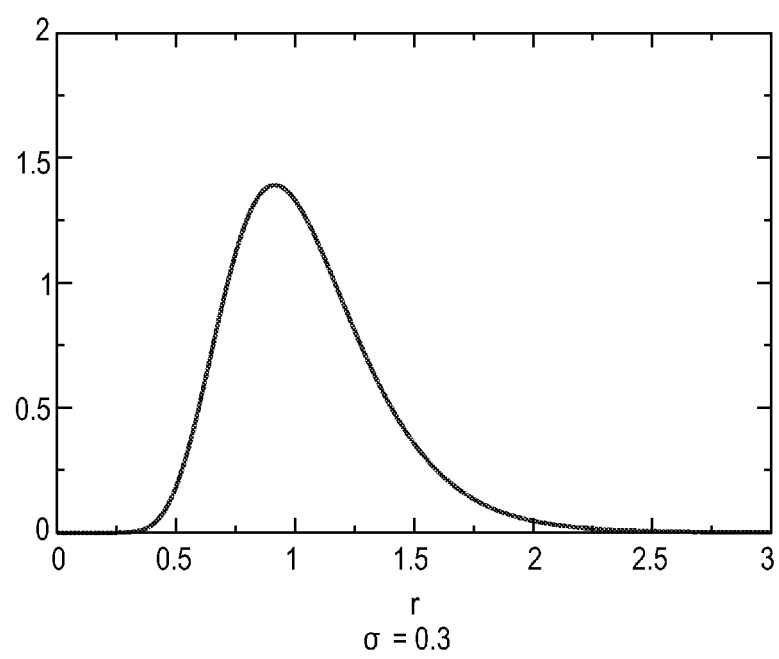
FIG. 11D σ = 0.3

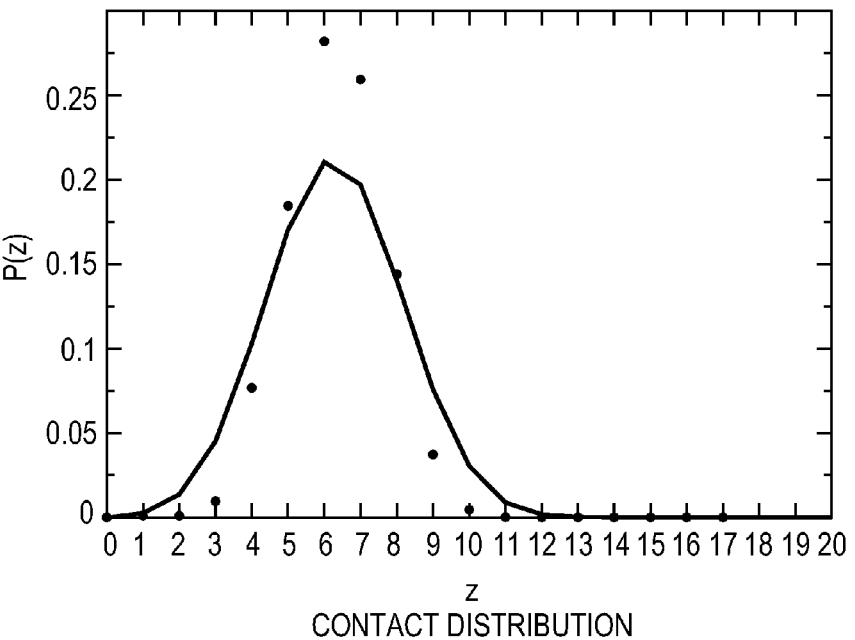
FIG. 11I CONTACT DISTRIBUTION
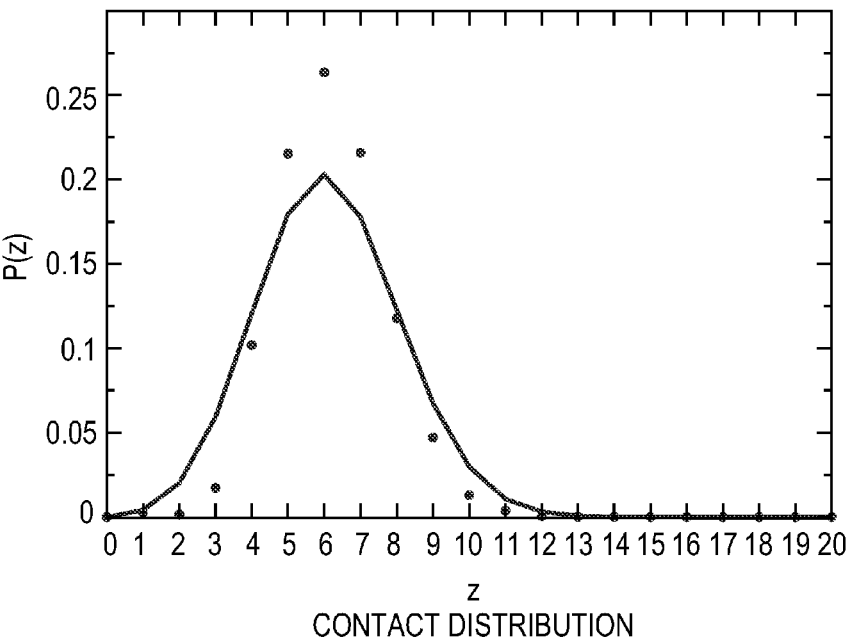
FIG. 11J CONTACT DISTRIBUTION

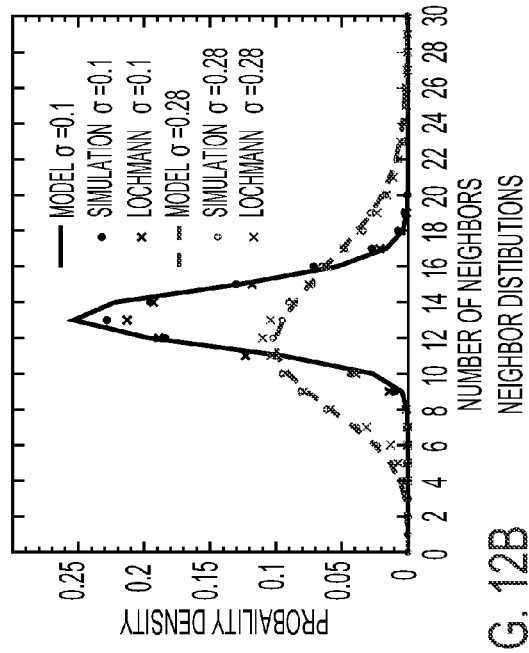
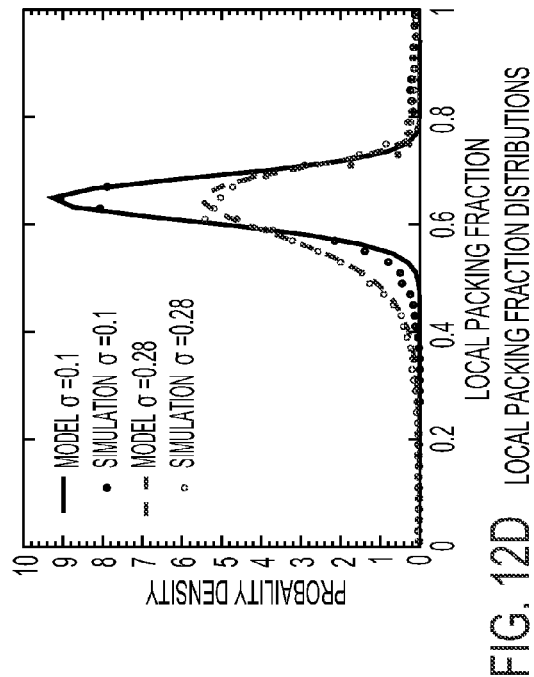
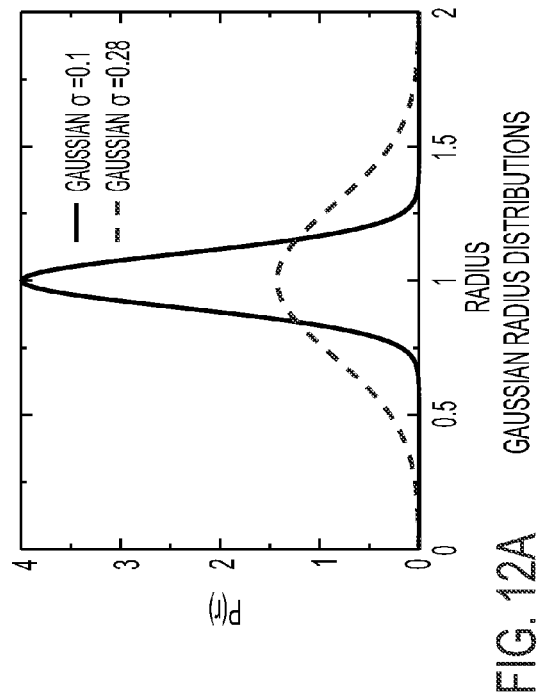
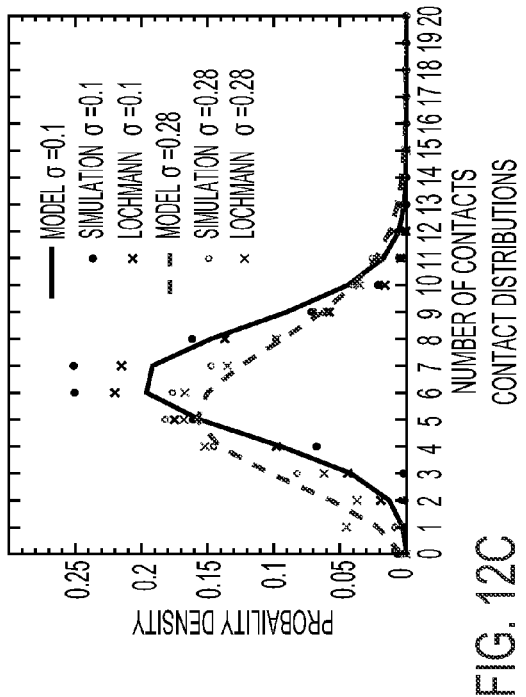
FIG. 12A GAUSSIAN RADIUS DISTRIBUTIONS
FIG. 12B NEIGHBOR DISTRIBUTIONS
FIG. 12C CONTACT DISTRIBUTIONS
FIG. 12D LOCAL PACKING FRACTION DISTRIBUTIONS

PACKING PROPERTIES OF PARTICULATE COMPOSITIONS

CROSS-REFERENCE TO RELATED PATENT APPLICATIONS

This application claims the benefit under 35 USC 119(e) of U.S. Application 61/144,353, filed Jan. 13, 2009 and is incorporated herein by reference in its entirety.

STATEMENT OF GOVERNMENT INTEREST

This work was partially supported by New York University MRSEC Award DMR: 0820341.

This invention is directed to packing properties of particulate compositions. More particularly, the invention is directed to establishing a methodology to characterize packing properties of particulates and also how to prepare particulate compositions to achieve a selected packing arrangement and attain desired properties associated with the particulate compositions.

BACKGROUND OF THE INVENTION

Particulate matter is a pervasive constituent, ranging from droplets of fat in mayonnaise to boulders in an avalanche. Collections of many particles are considered to be a state of matter different from solids, liquids or gasses, distinguished by the existence of an amorphous and mechanically stable jammed state. Packing problems are ubiquitous, ranging from oil extraction through porous rocks to grain storage in silos and the compaction of pharmaceutical powders in tablets or capsules. At a given density, particulate systems pack into a mechanically stable and in cases into an amorphous state. Theoretical frameworks have proposed a connection between jamming and the glass transition, the thermodynamics of jamming and geometric modeling of random packings. Nevertheless, a simple underlying mechanism for the random assembly of athermal particles, analogous to crystalline ordering, remains unknown.

SUMMARY OF THE INVENTION

The invention involves use of three-dimensional measurements of polydisperse packings of frictionless or emulsion particles to build a simple statistical model in which the complexity of the global packing is distilled into a local stochastic process. From the perspective of a single particle, the packing problem is reduced to the random assembly or formation of nearest neighbors, followed by a random choice of contacts among them. There are several key parameters in the model, the available solid angle around each particle and the ratio of contacts to neighbors; and these can be directly obtained from experiments. We demonstrate that this "granocentric" view captures the essential properties of the polydisperse emulsion packing, ranging from the microscopic distributions of nearest neighbors and contacts to local density fluctuations and all the way to the global packing density. This model reveals a general principle of organization for random packing and provides the foundation for a theory of jammed packings. In addition, application of our results to monodisperse and bidisperse systems provides quantitative agreement with previously measured trends in global density.

BRIEF DESCRIPTION OF THE DRAWINGS

FIG. 1A illustrates microstructure of a randomly-packed, polydisperse emulsion with a projection of a 3D confocal image of a creamed emulsion (scale bar is 3 micrometers) with droplets shown in green fluorescence (505-570 nm) and droplet contacts in yellow fluorescence (576-640 nm); and the "star" indicates a test particle described in FIG. 2A below; FIG. 1B shows a plot of emulsion droplet radii versus probability density with a mean value at 3.3 micrometers and a standard deviation of 0.74 micrometers; FIG. 1C (1) shows tessellation of the image in FIG. 1A with a local cell shown for each droplet and also the associated adjacent color map in grayscale map in FIG. 1C (2) indicating the number of neighbors of each droplet.

Figure 9A:
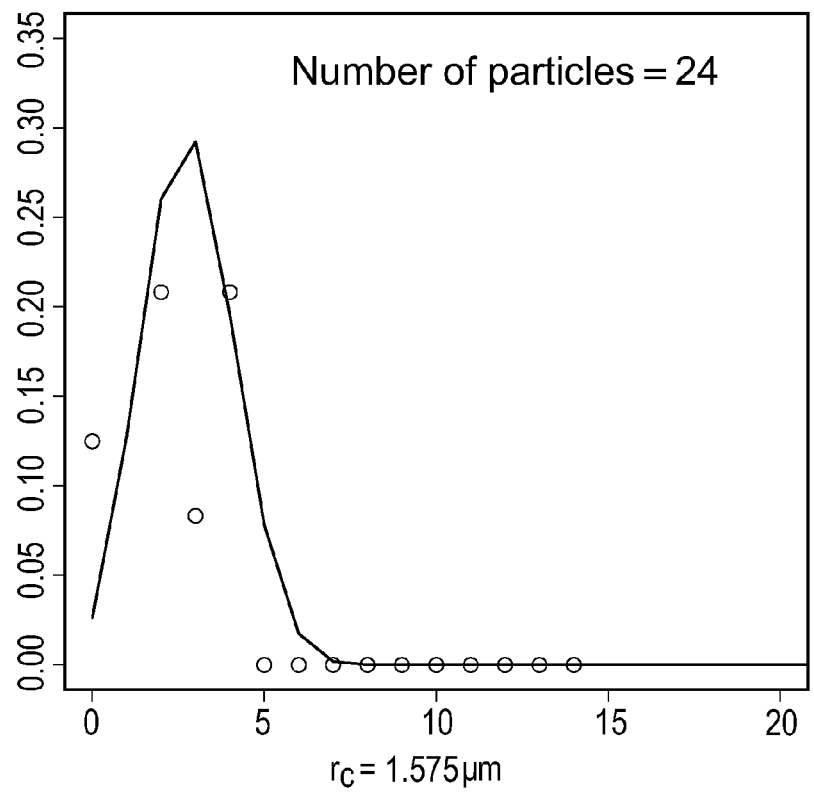
Figure 9B:
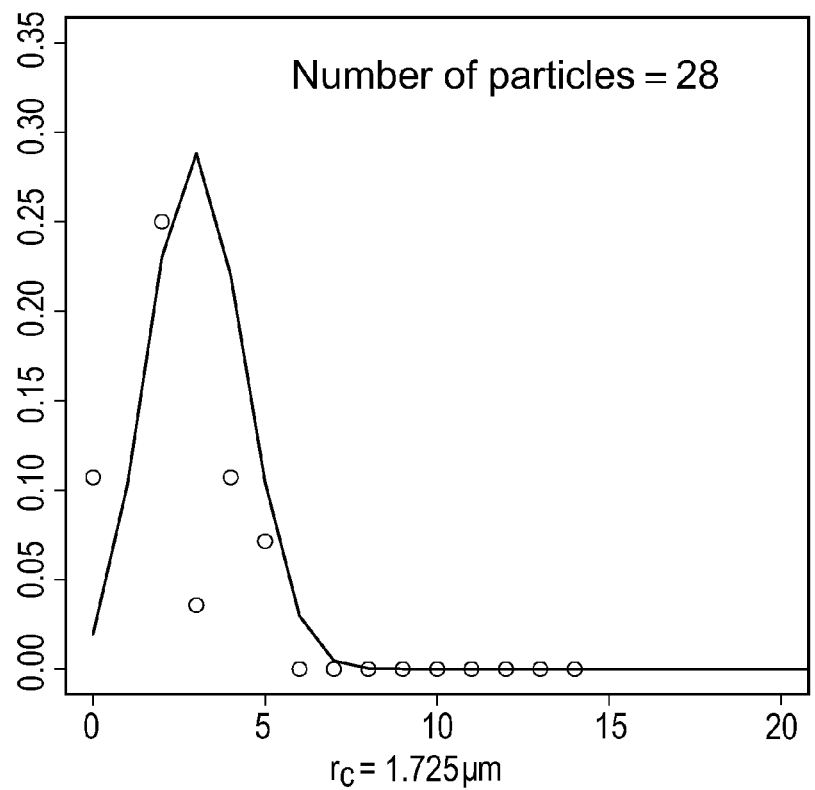
Figure 9C:
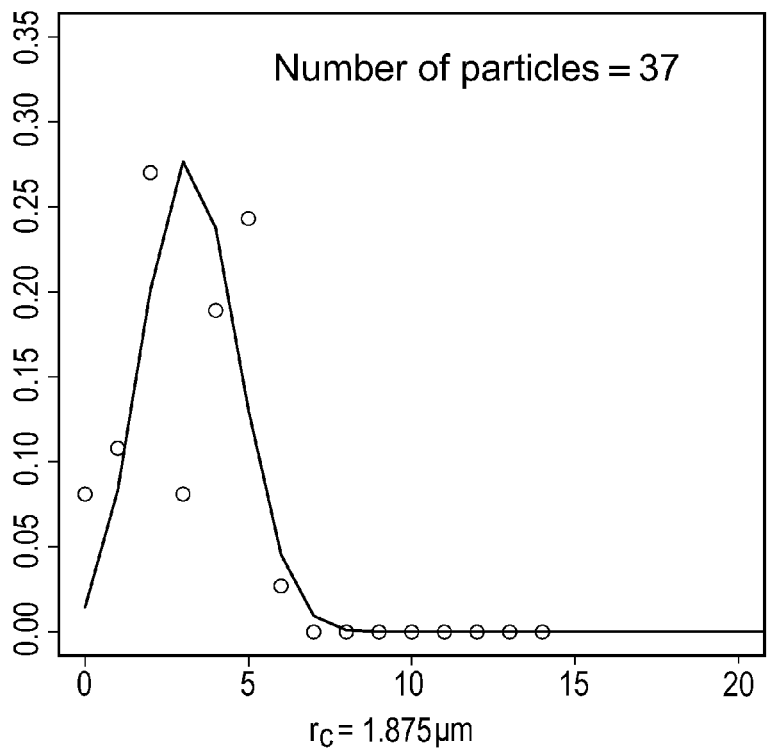
Figure 9D:
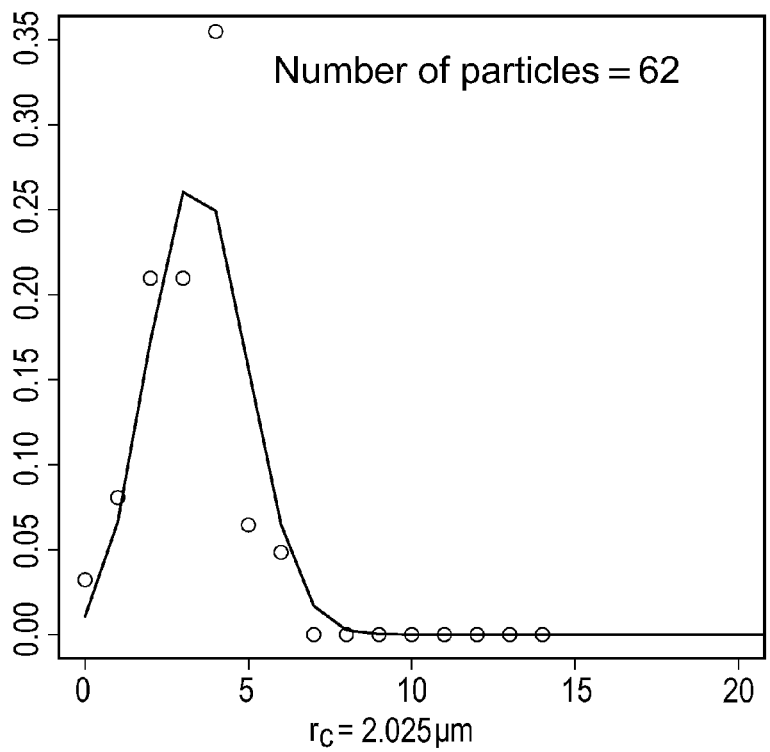
Figure 9E:
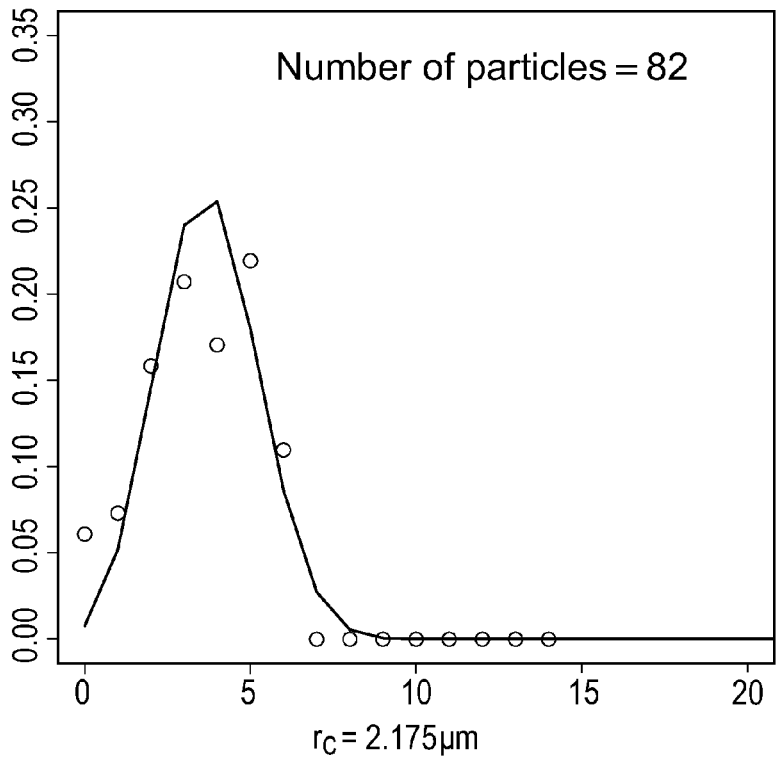
Figure 9F:
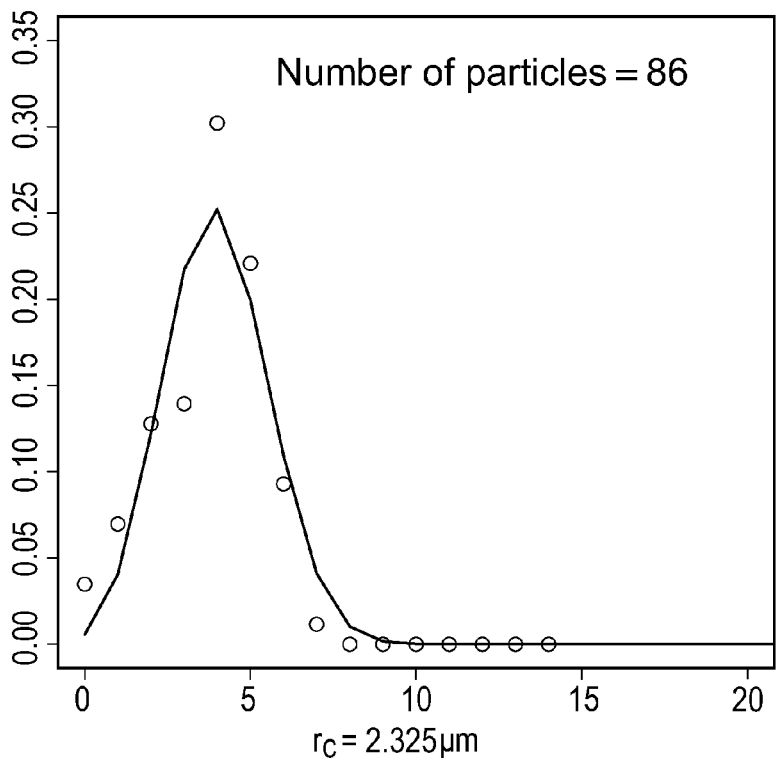
Figure 9G:
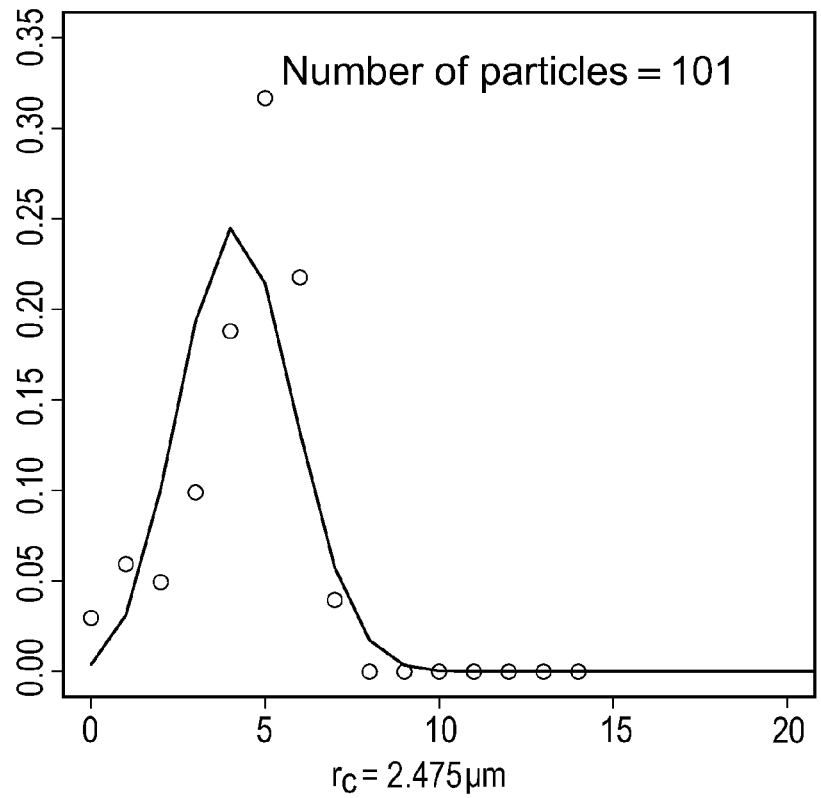
Figure 9H:
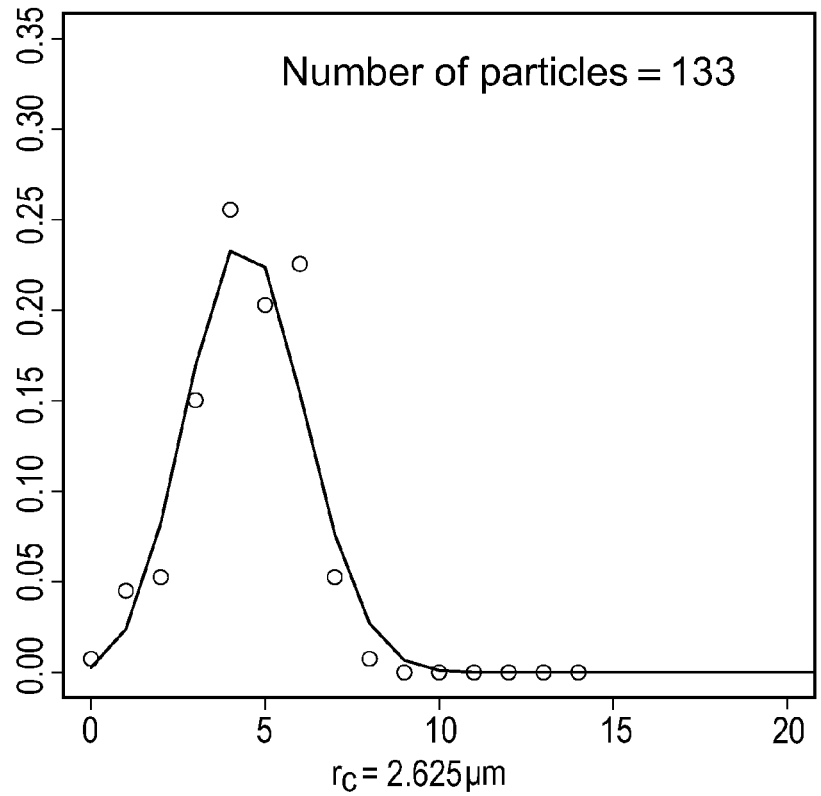
Figure 9I:
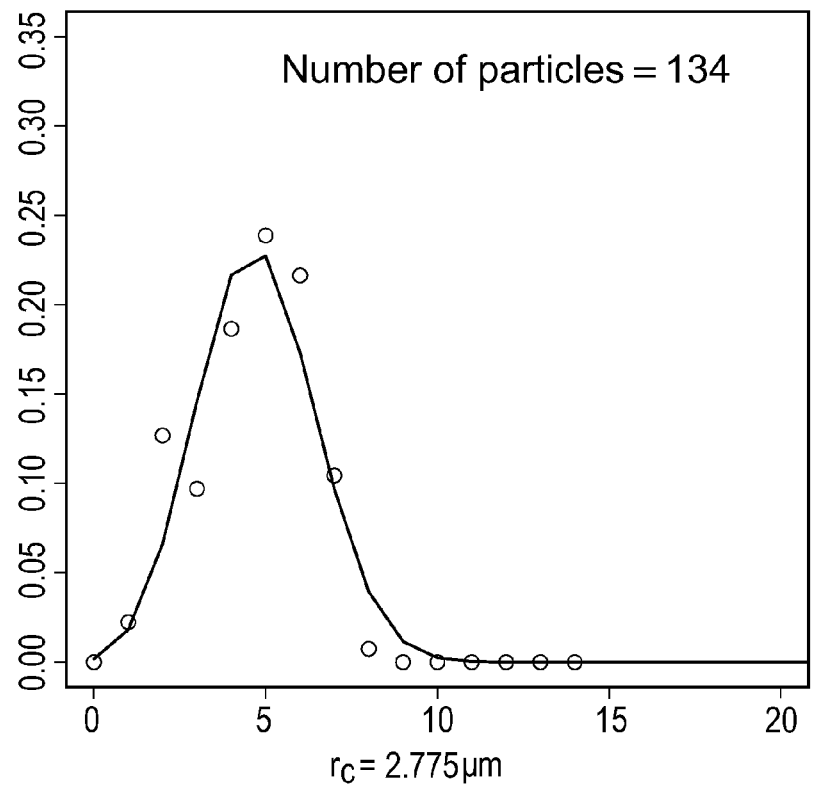
Figure 9J:
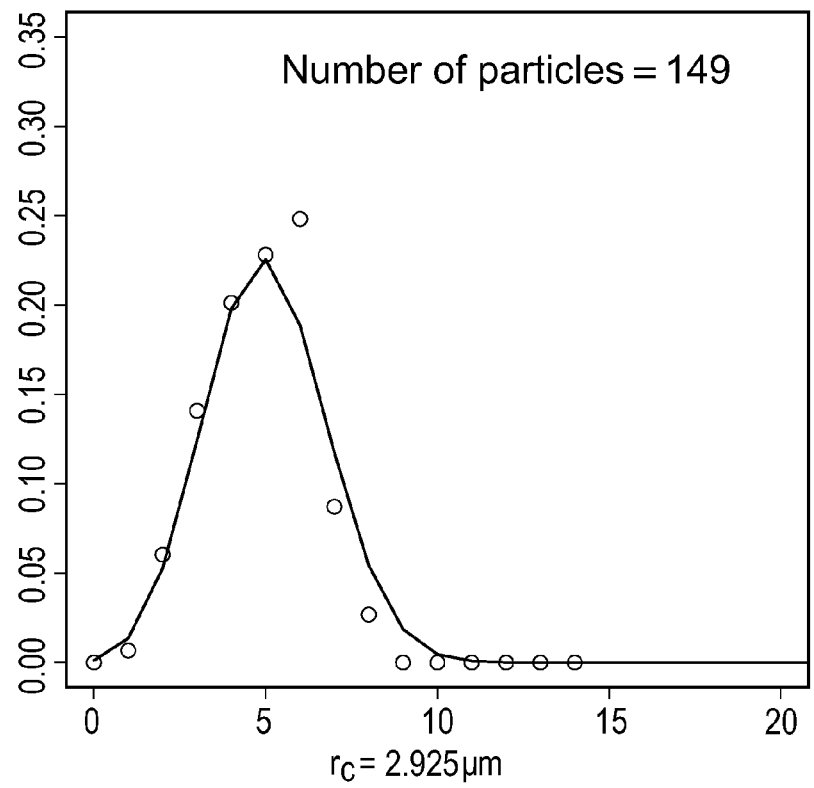
Figure 9K:
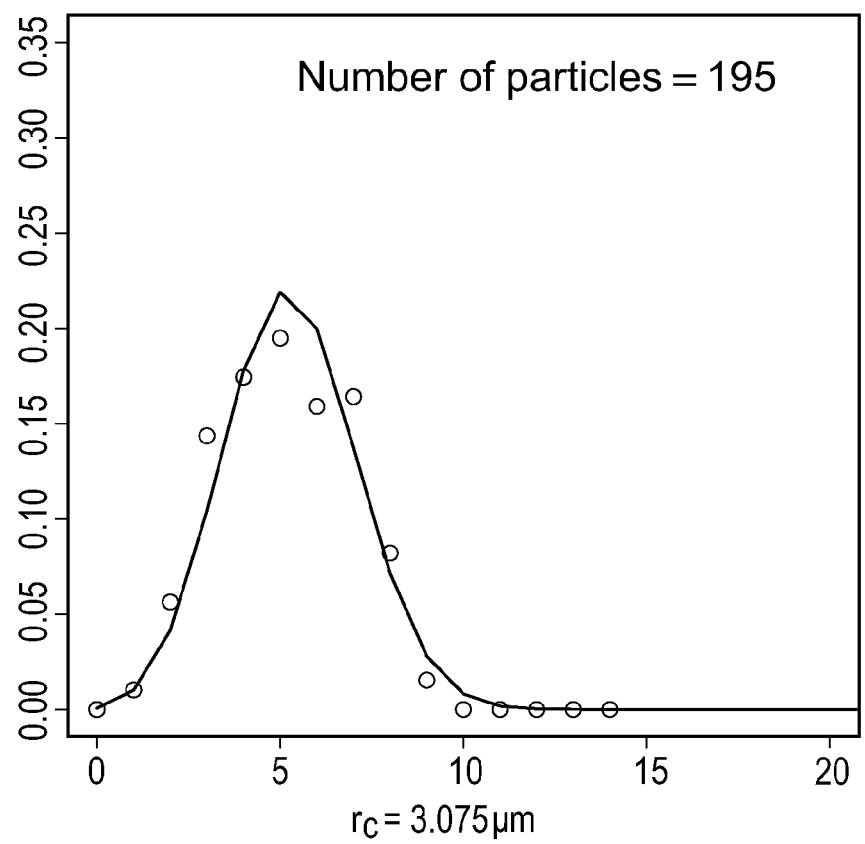
Figure 9L:
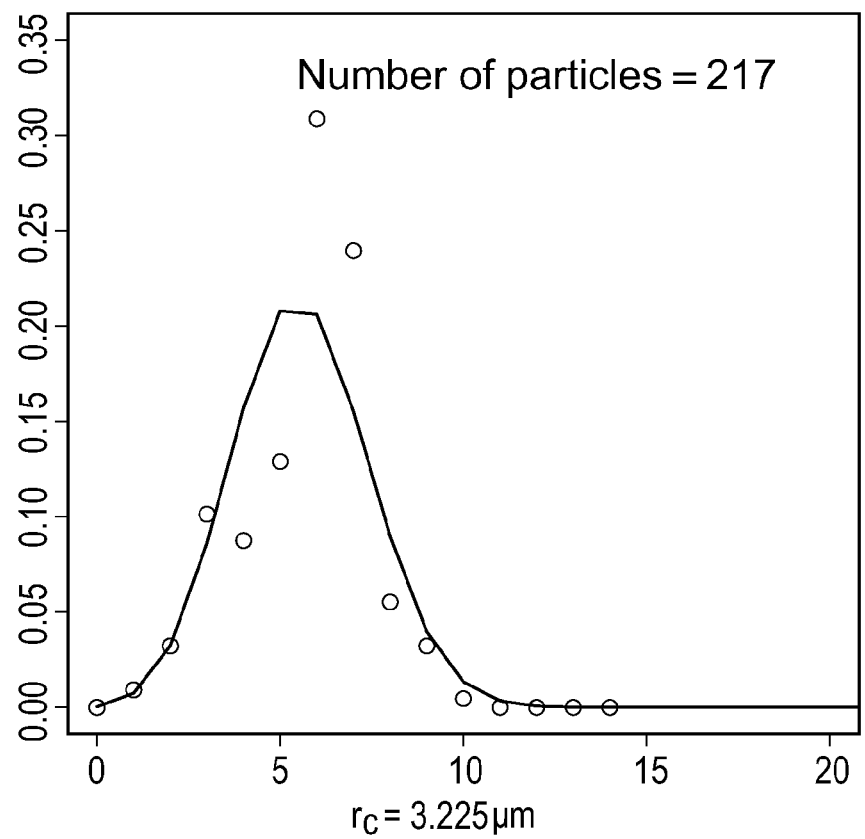
Figure 9M:
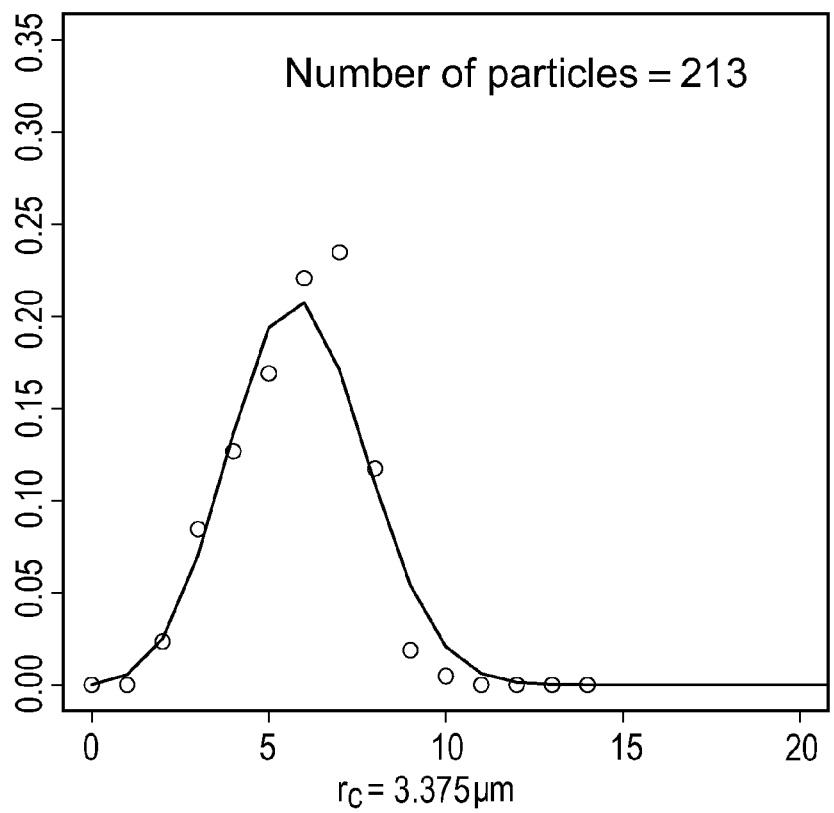
Figure 9N:
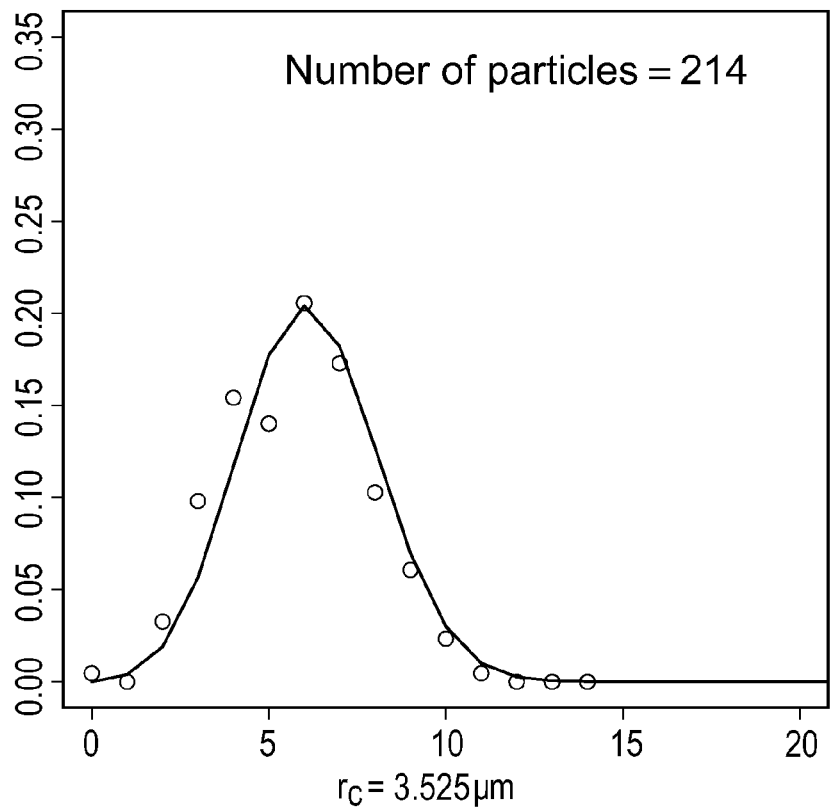
Figure 9O:
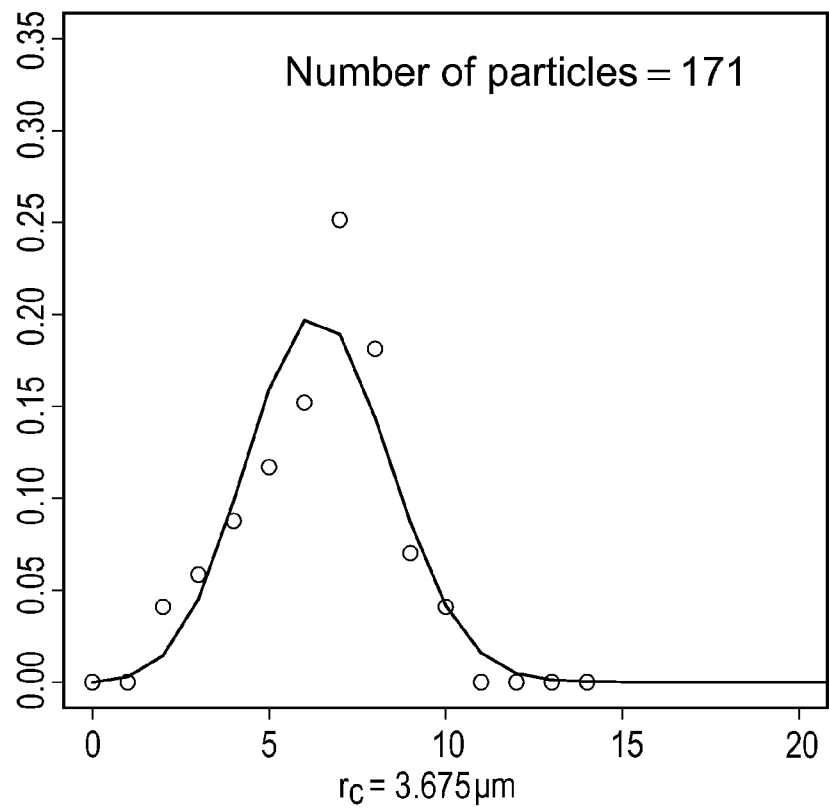
Figure 9P:
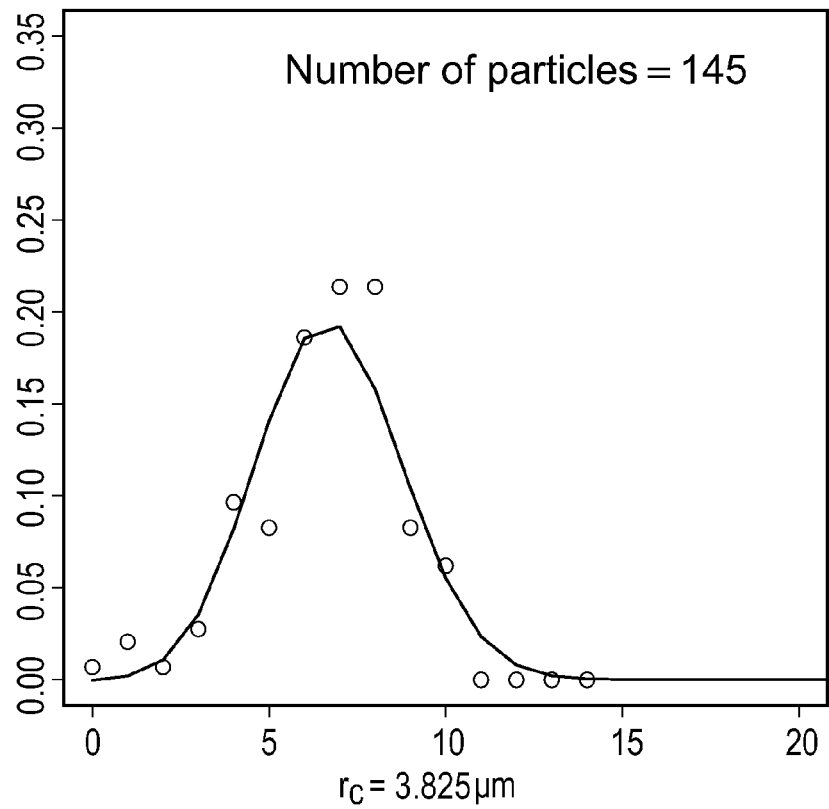
Figure 9Q:
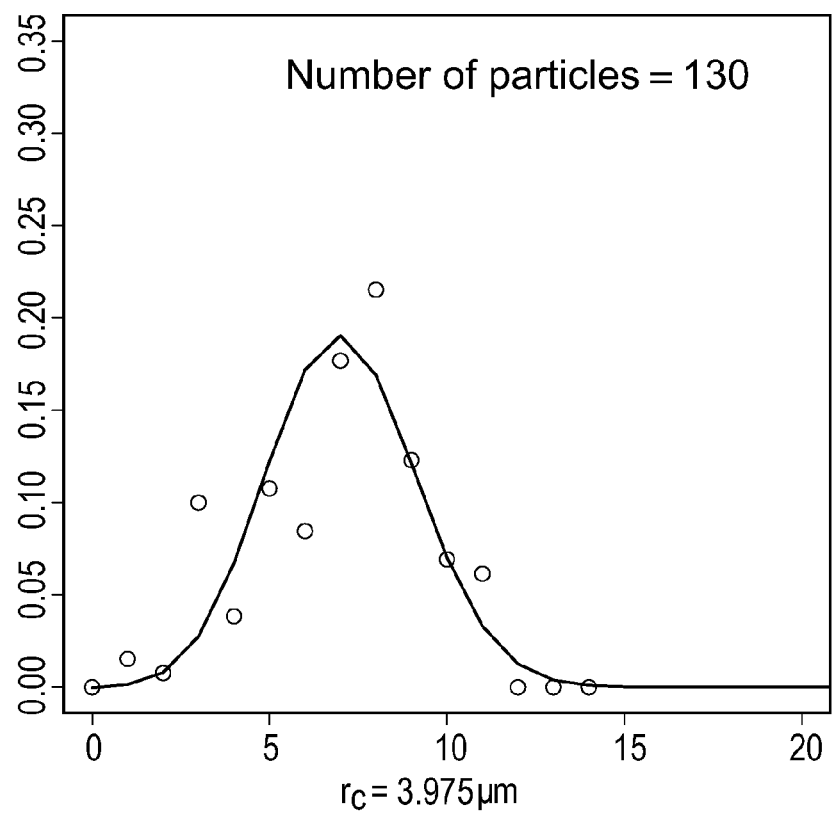
Figure 9R:
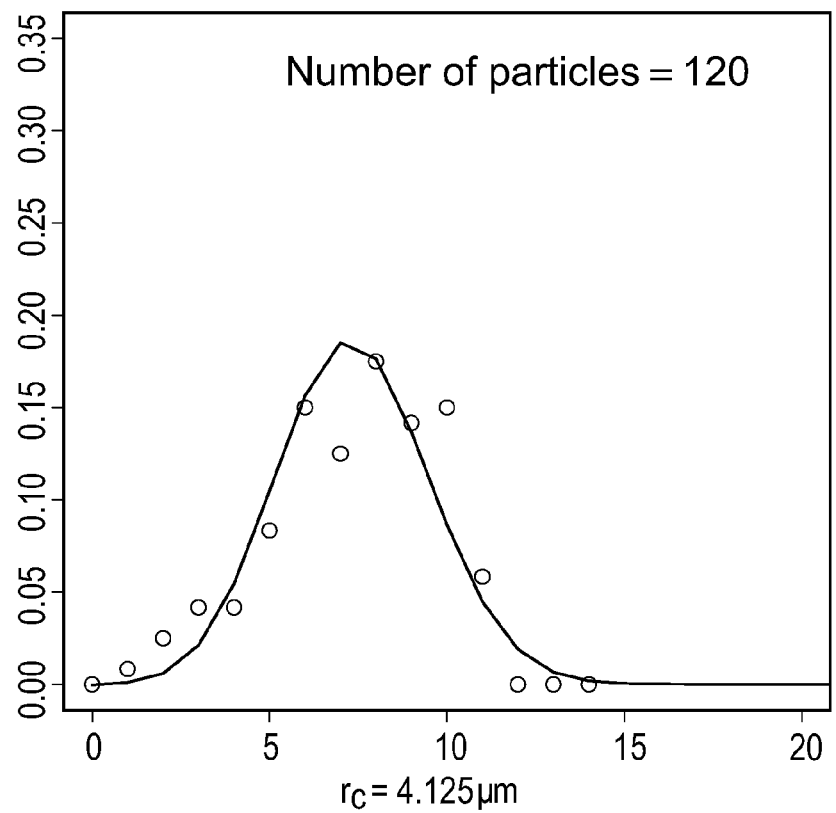
Figure 9S:
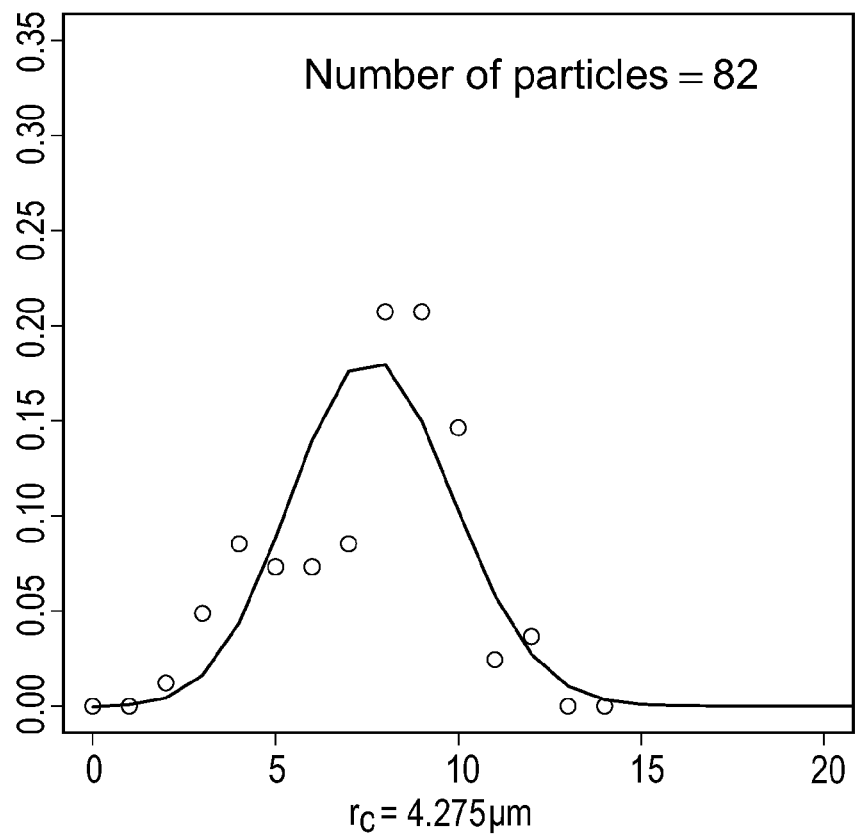
Figure 9T:
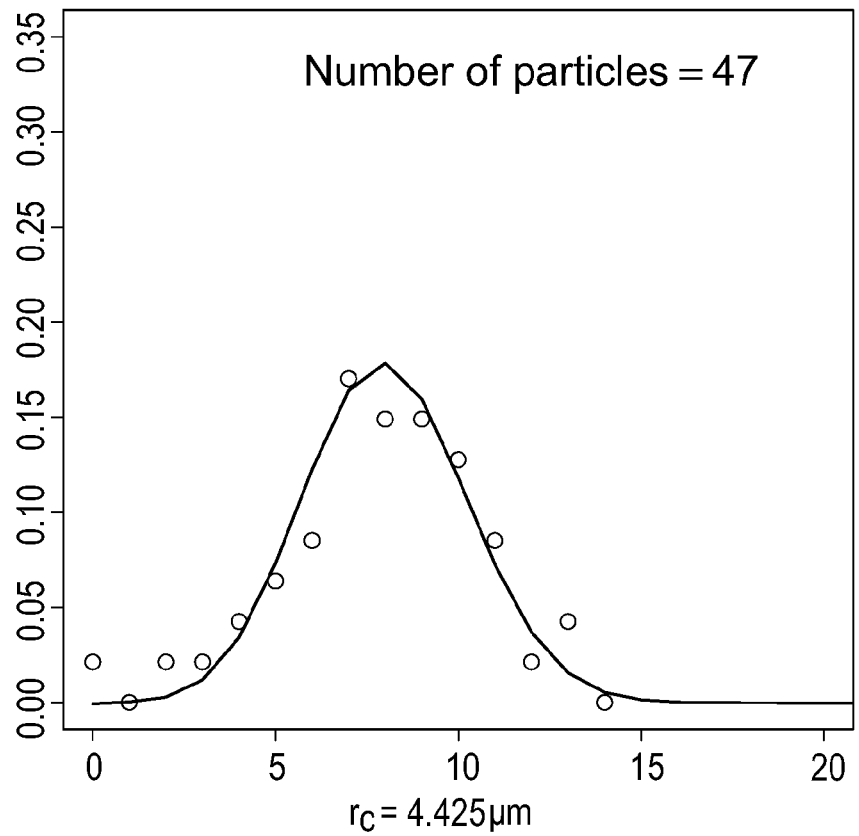
Figure 9U:
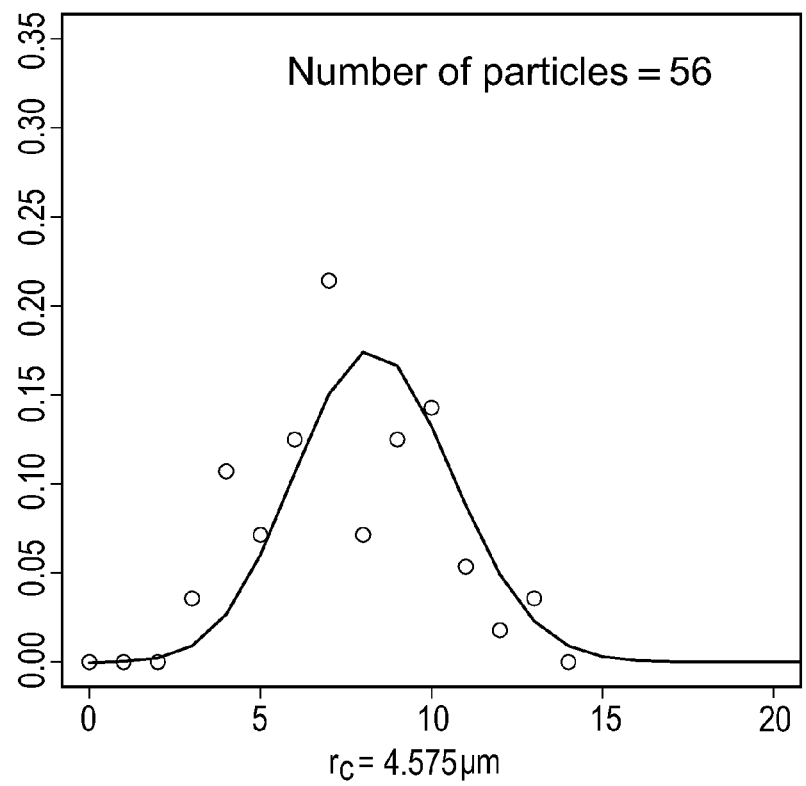
Figure 9V:
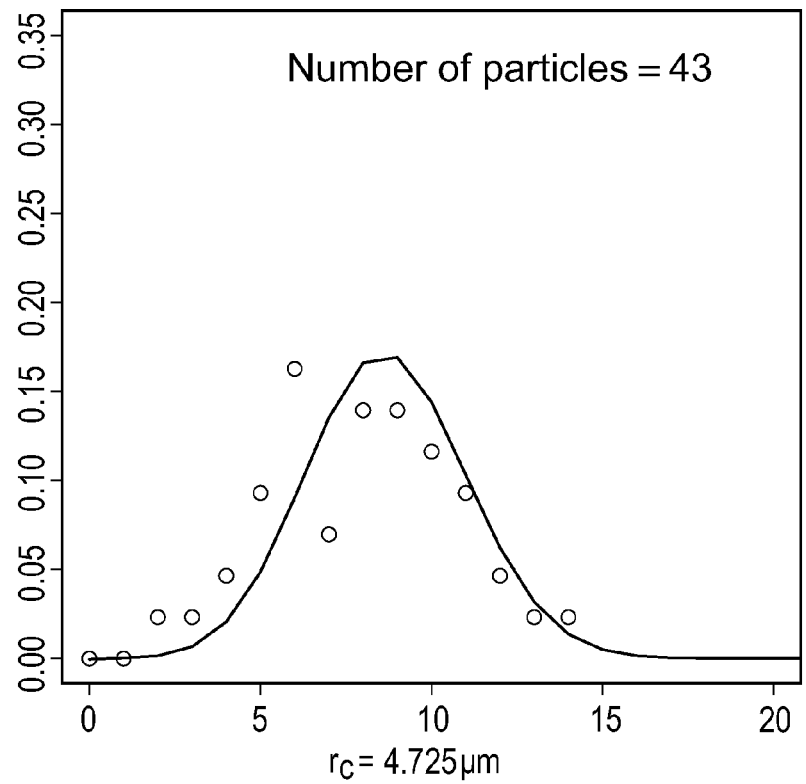
Figure 9W:
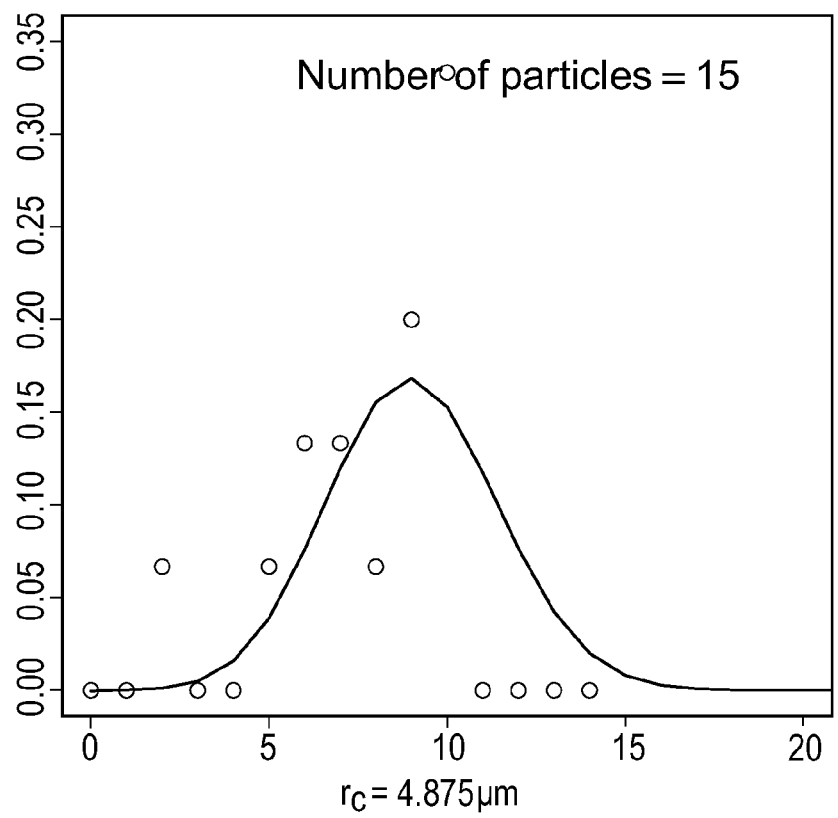
Figure 9X:
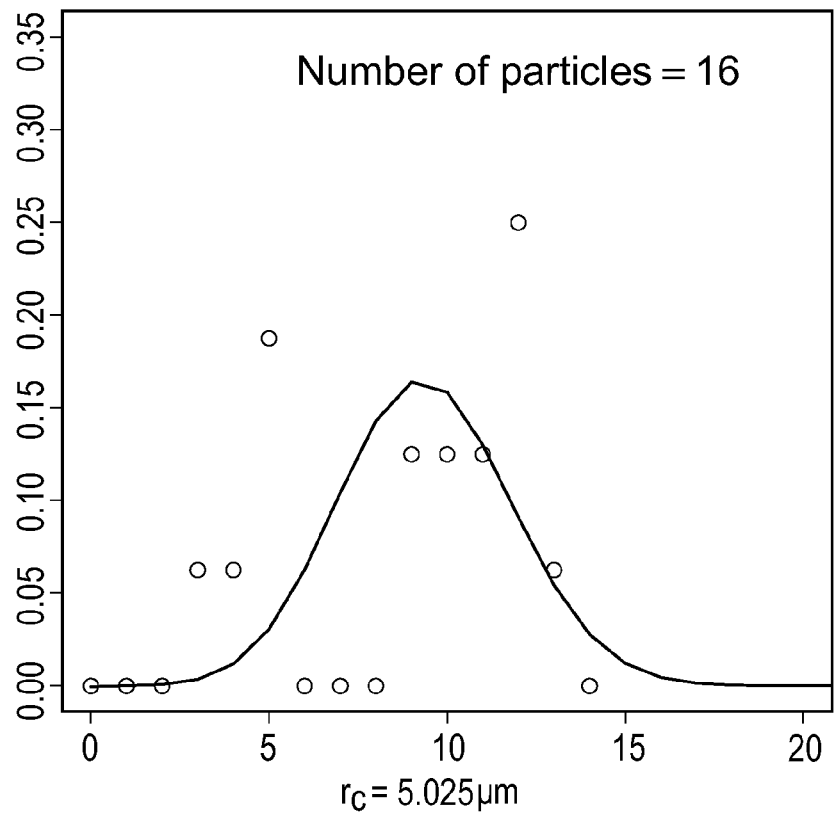
Figure 9Y:
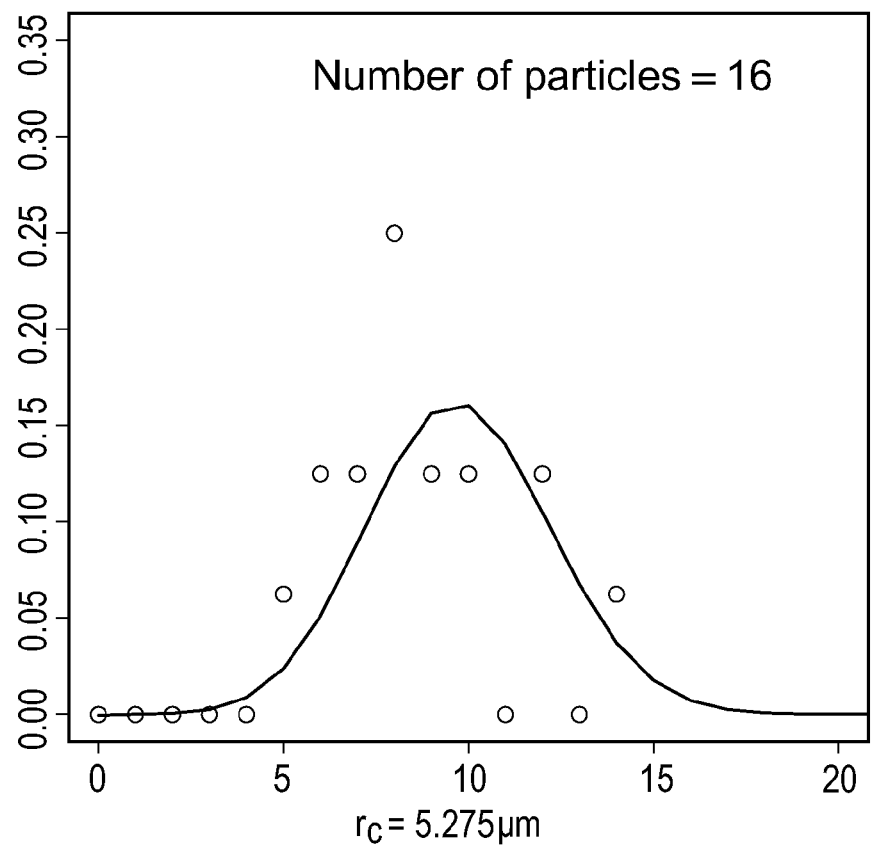
Figure 10A:
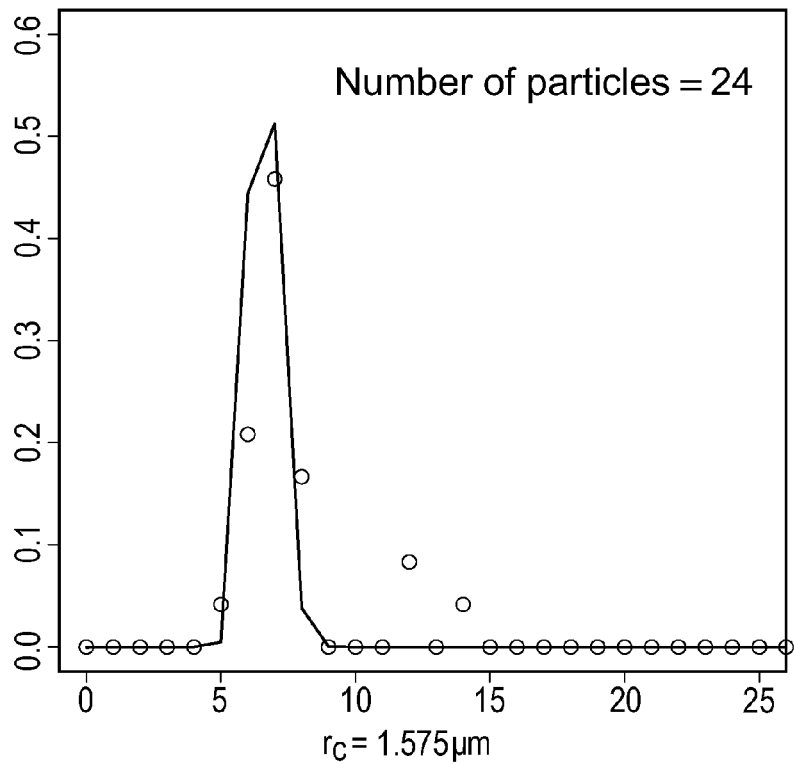
Figure 10B:
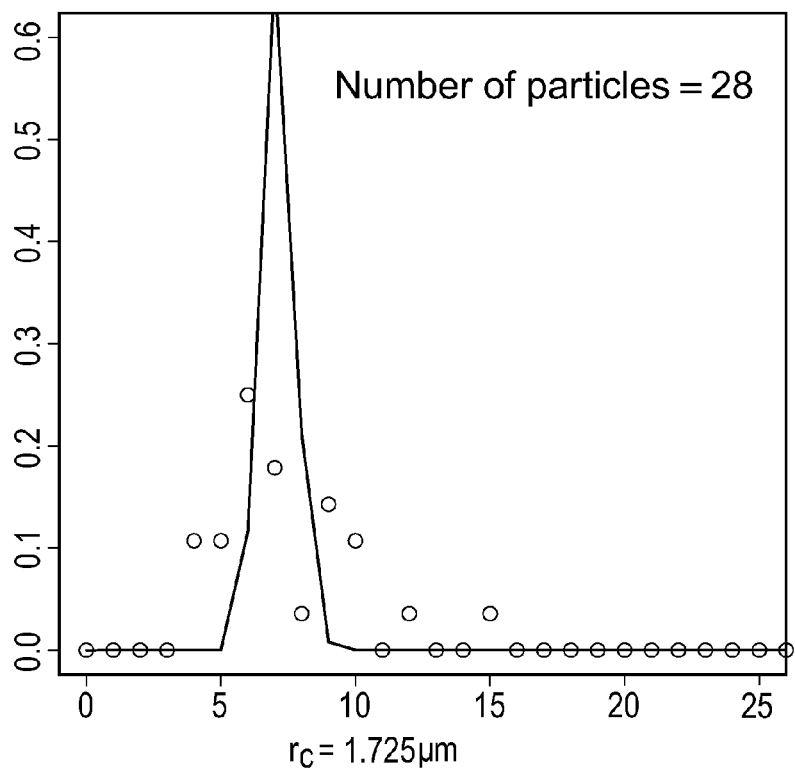
Figure 10C:
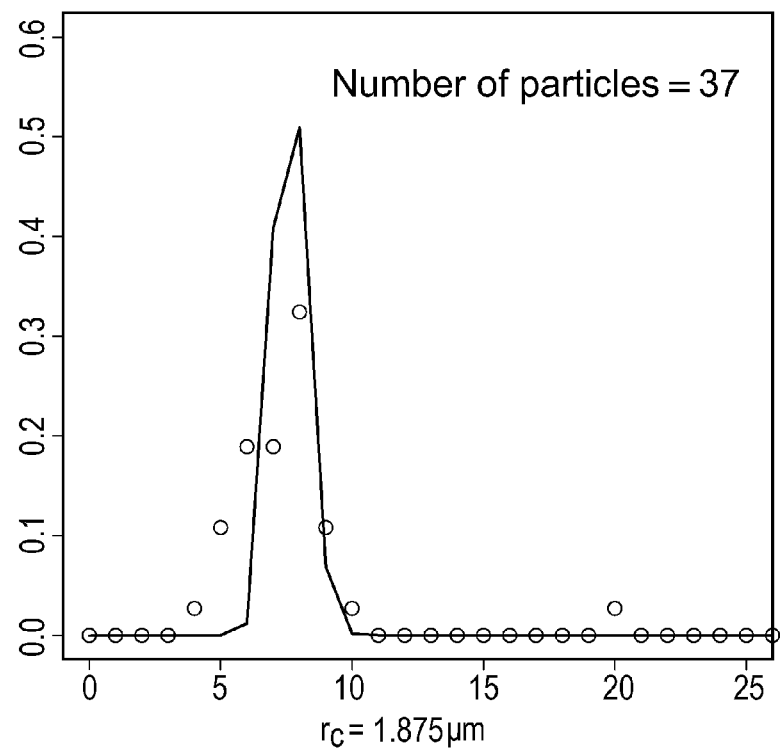
Figure 10D:
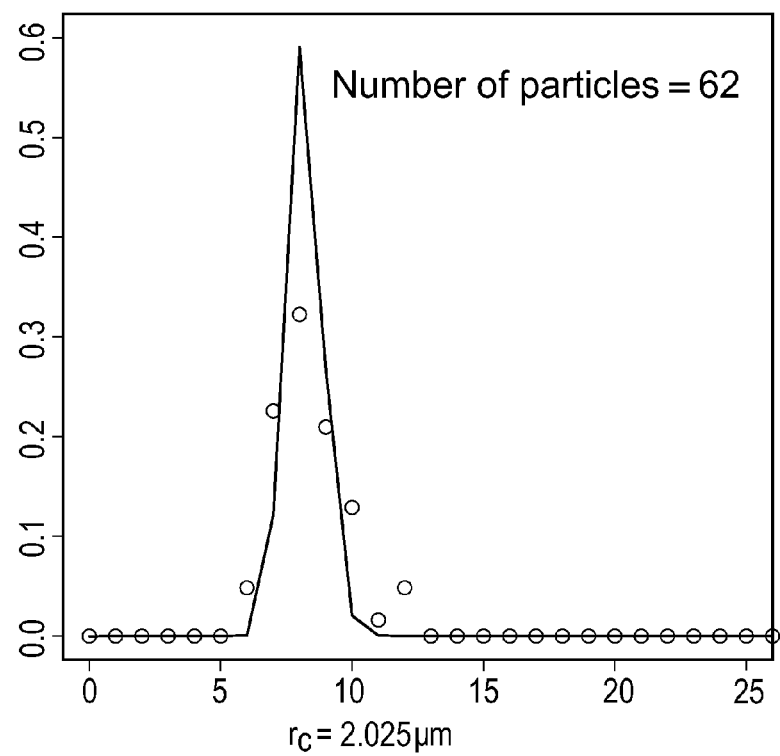
Figure 10E:
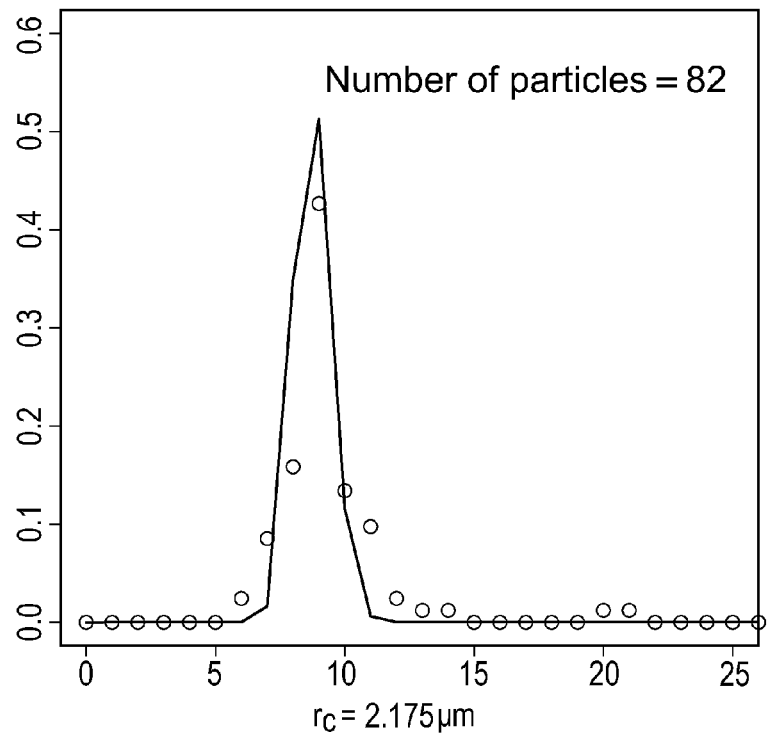
Figure 10F:
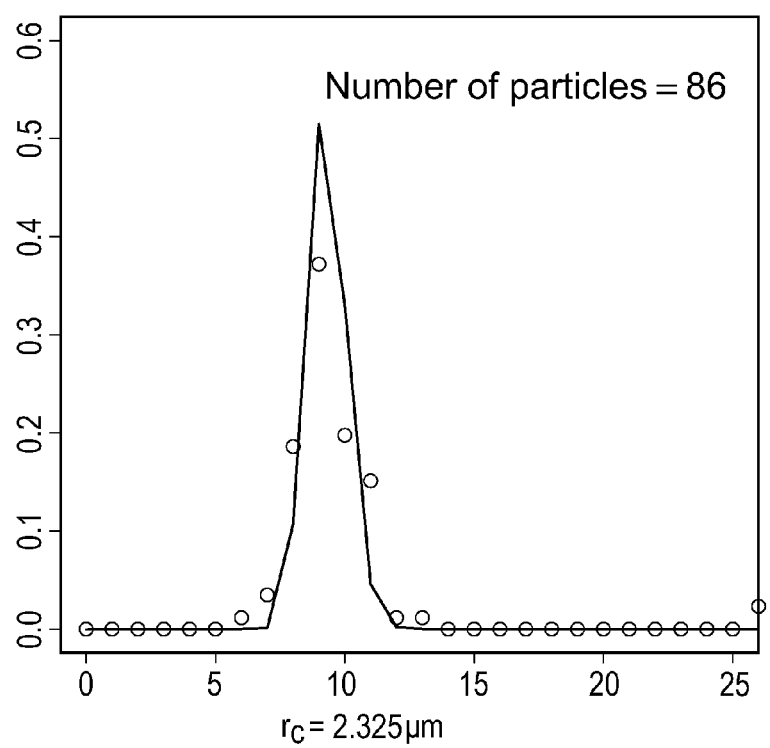
Figure 10G:
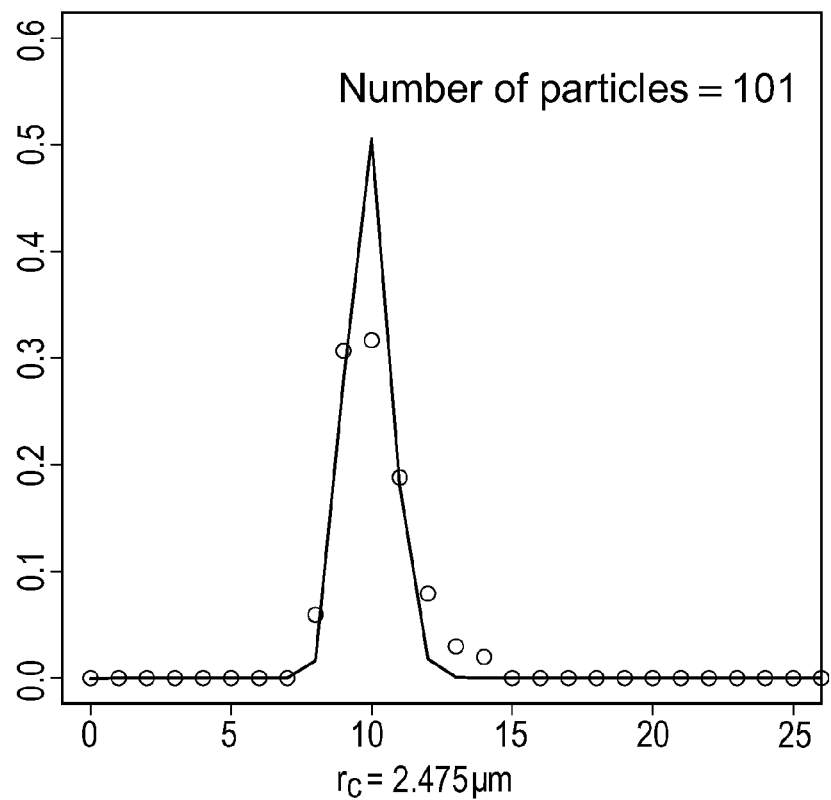
Figure 10H:
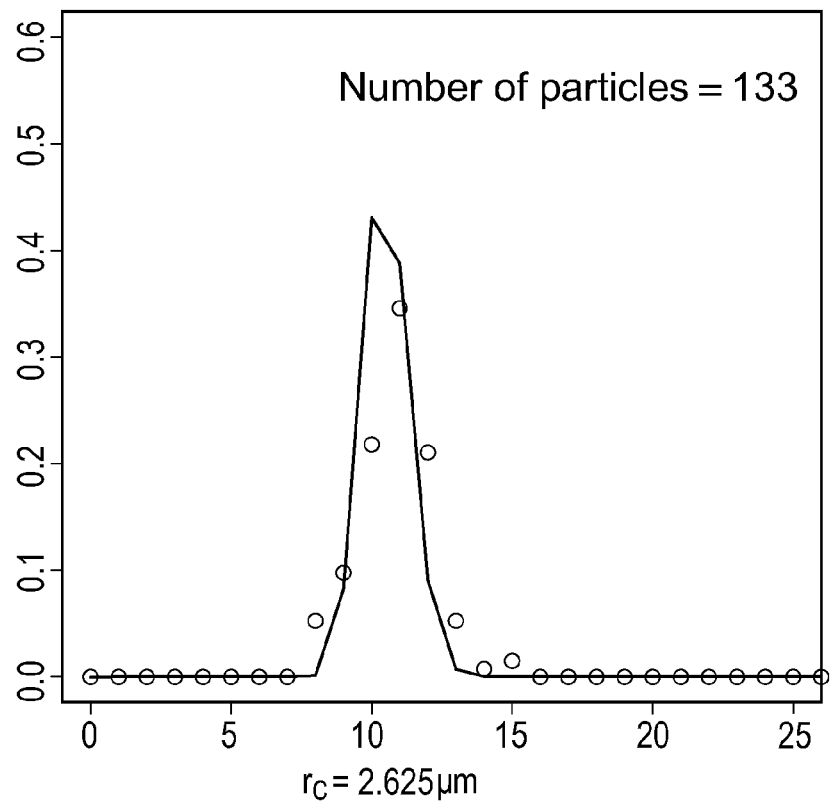
Figure 10I:
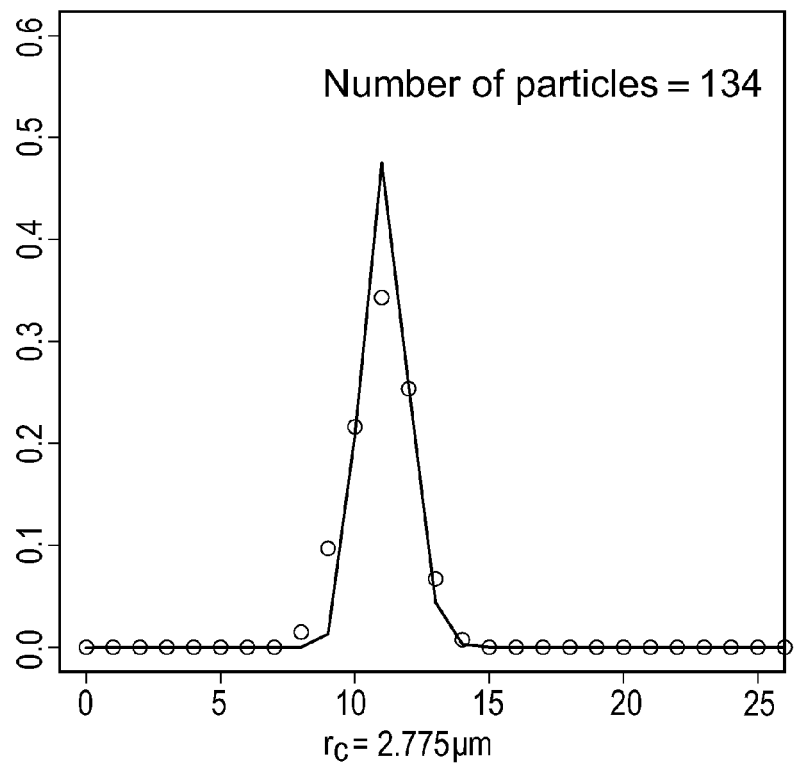
Figure 10J:
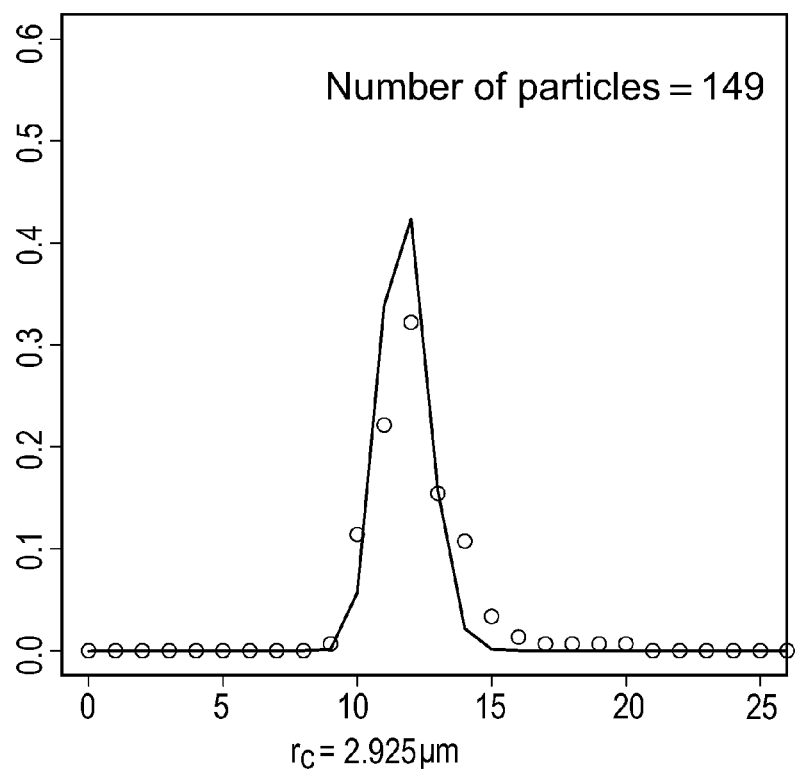
Figure 10K:
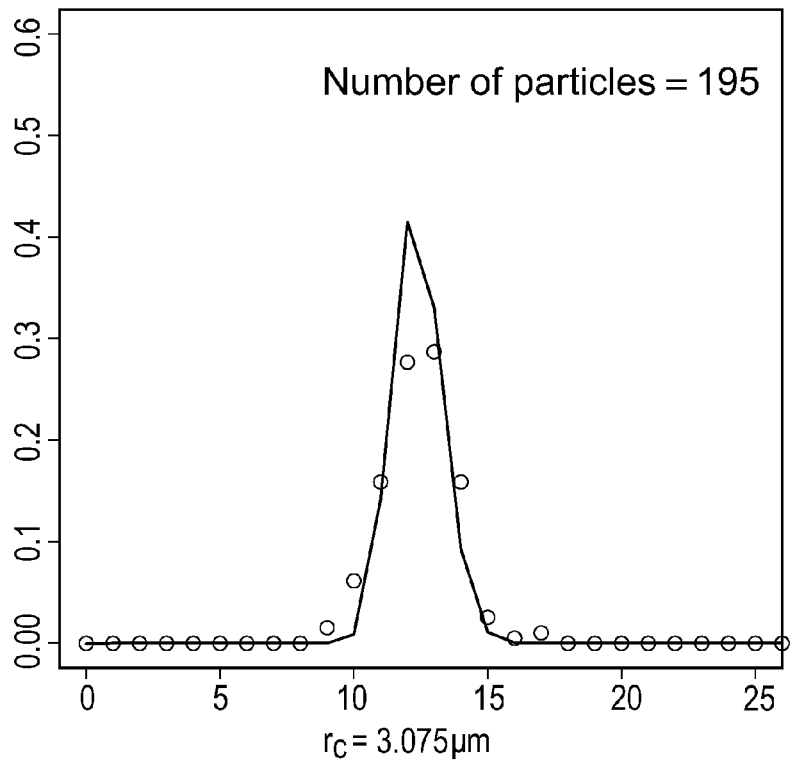
Figure 10L:
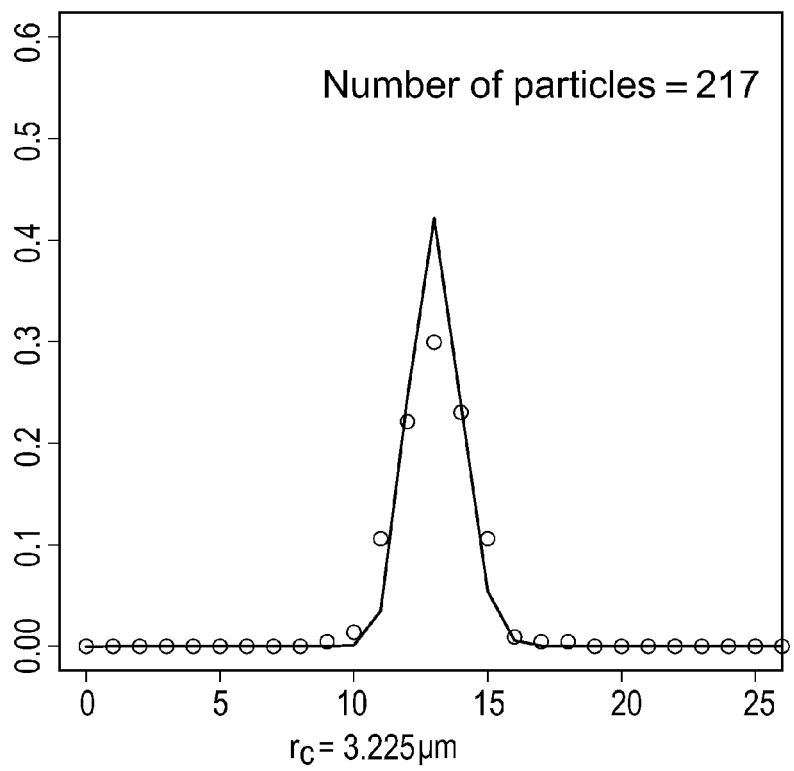
Figure 10M:
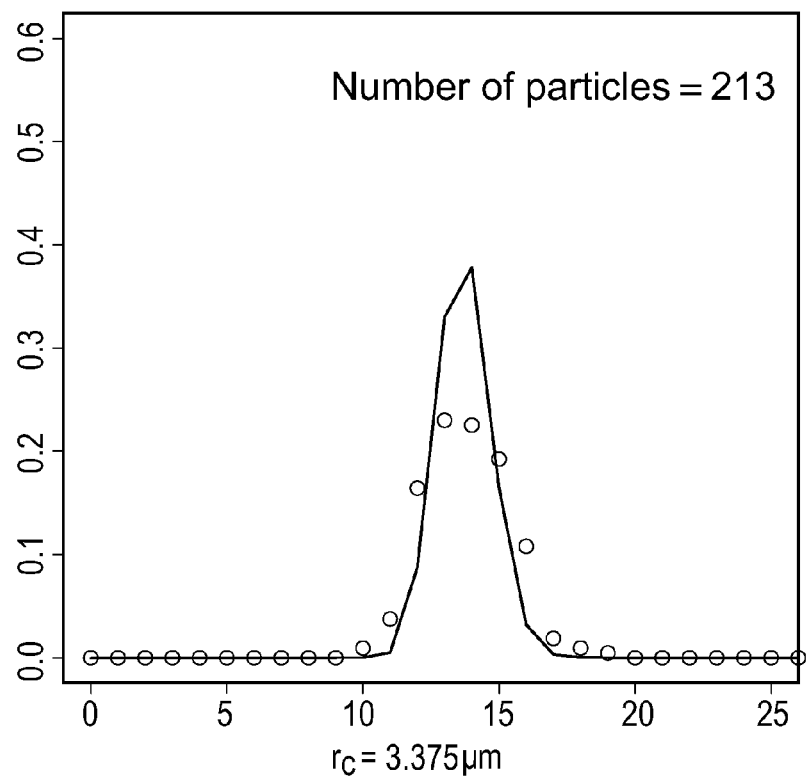
Figure 10N:
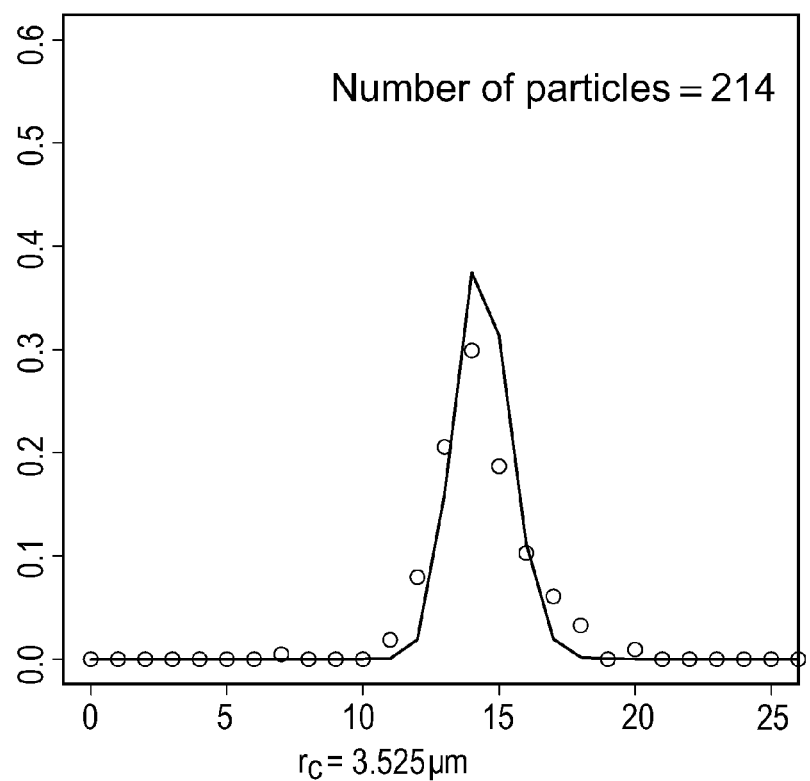
Figure 10O:
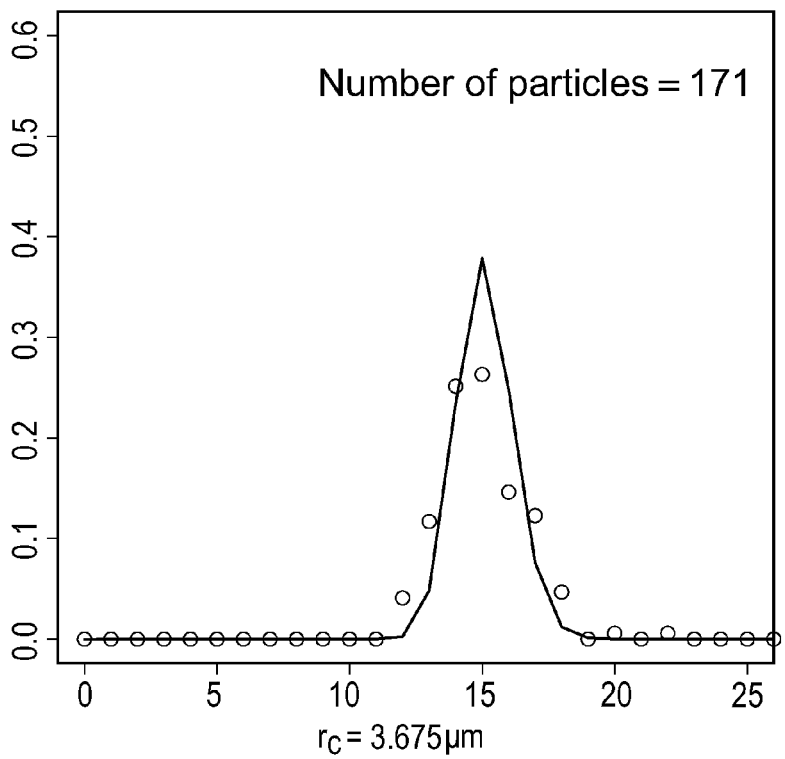
Figure 10P:
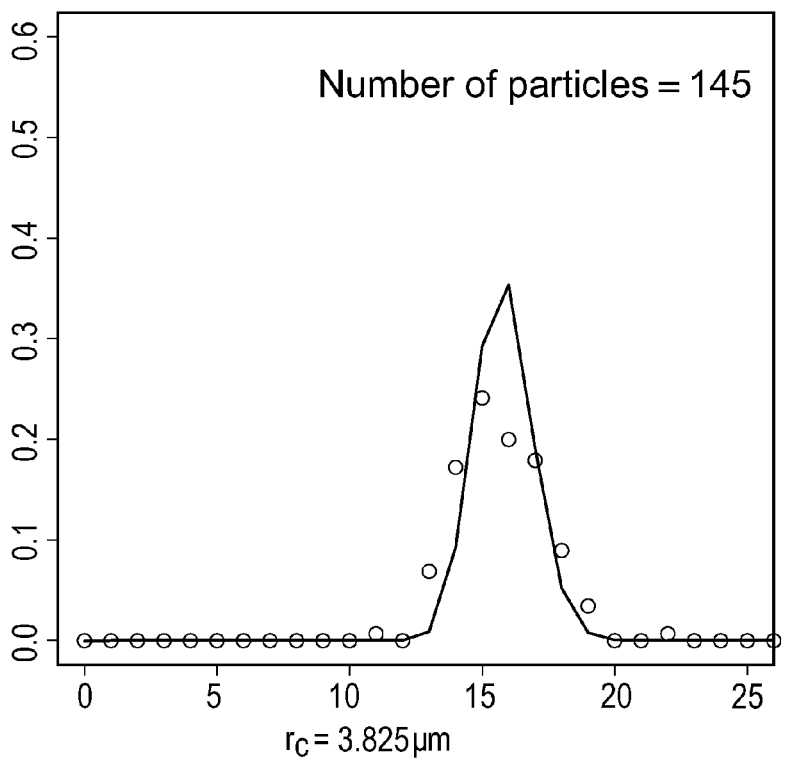
Figure 10Q:
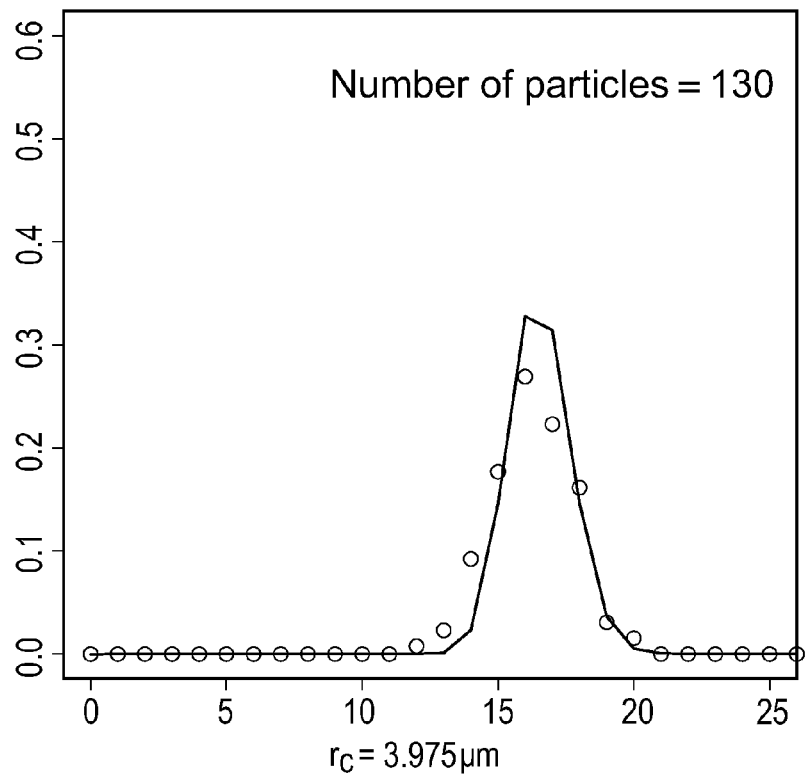
Figure 10R:
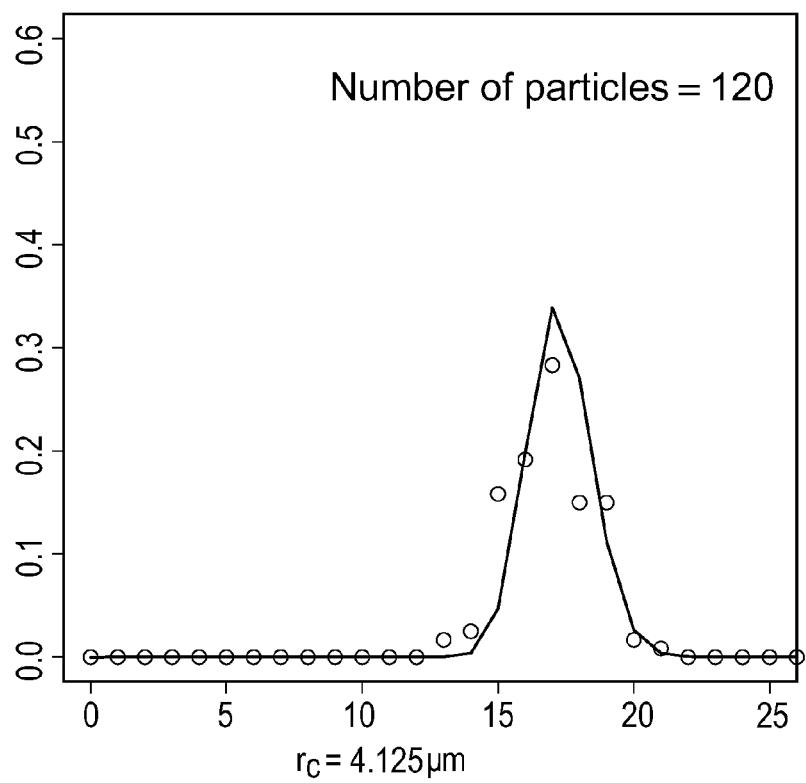
Figure 10S:
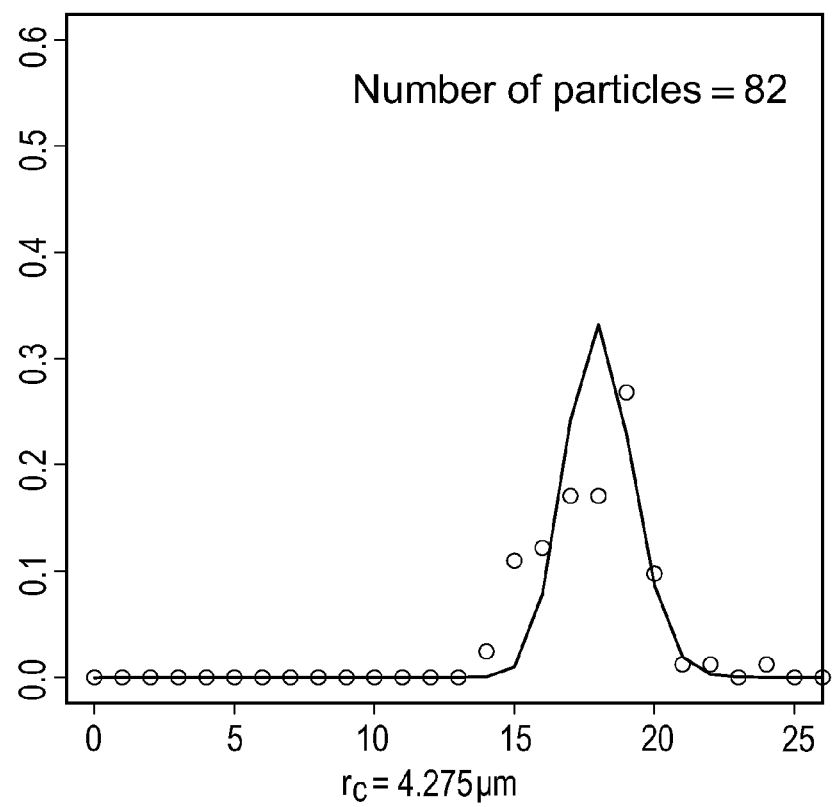
Figure 10T:
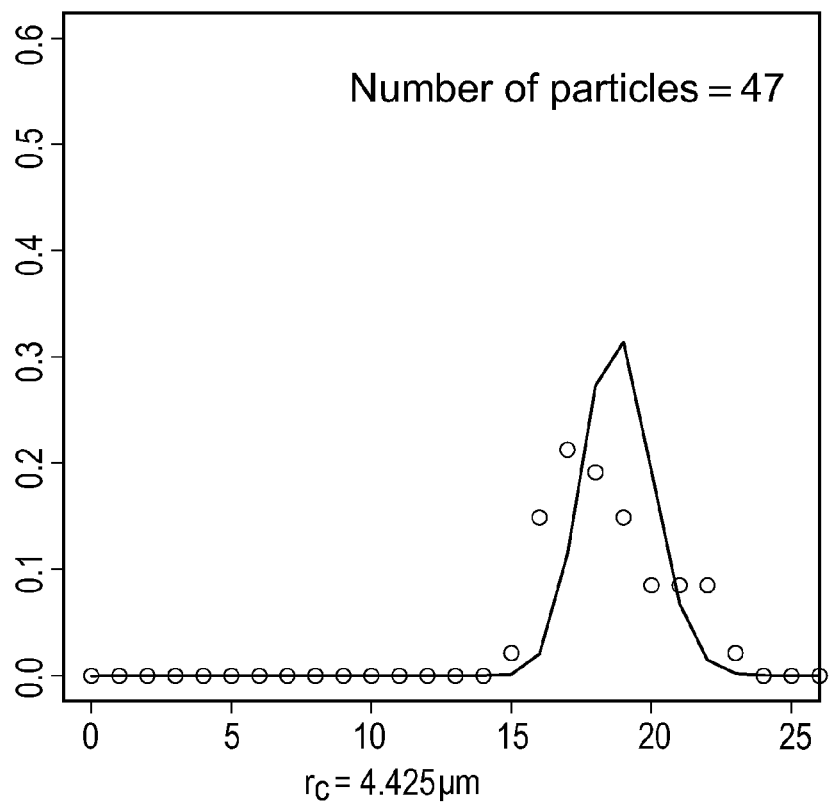
Figure 10U:
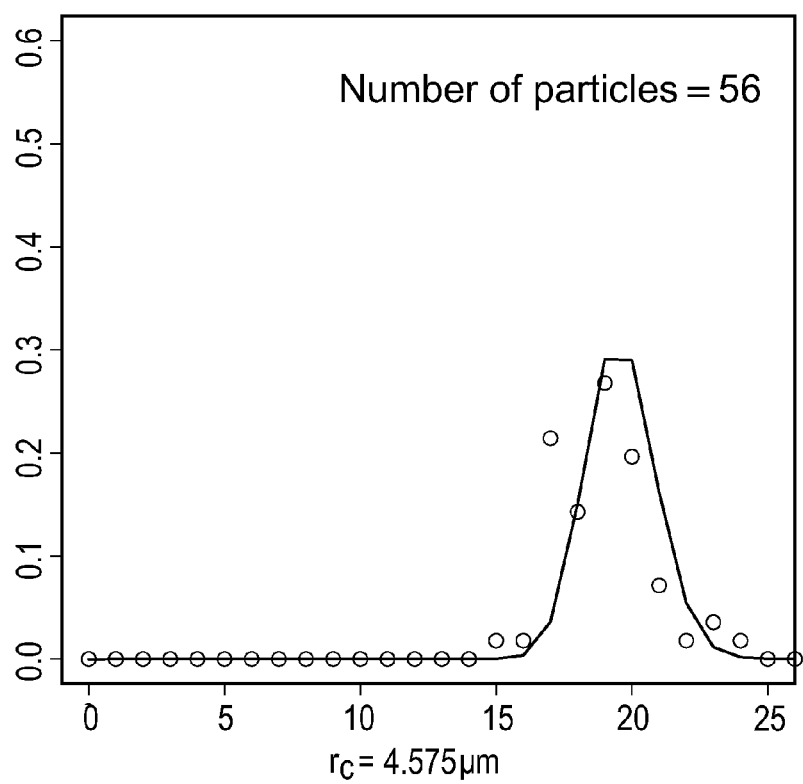
Figure 10V:
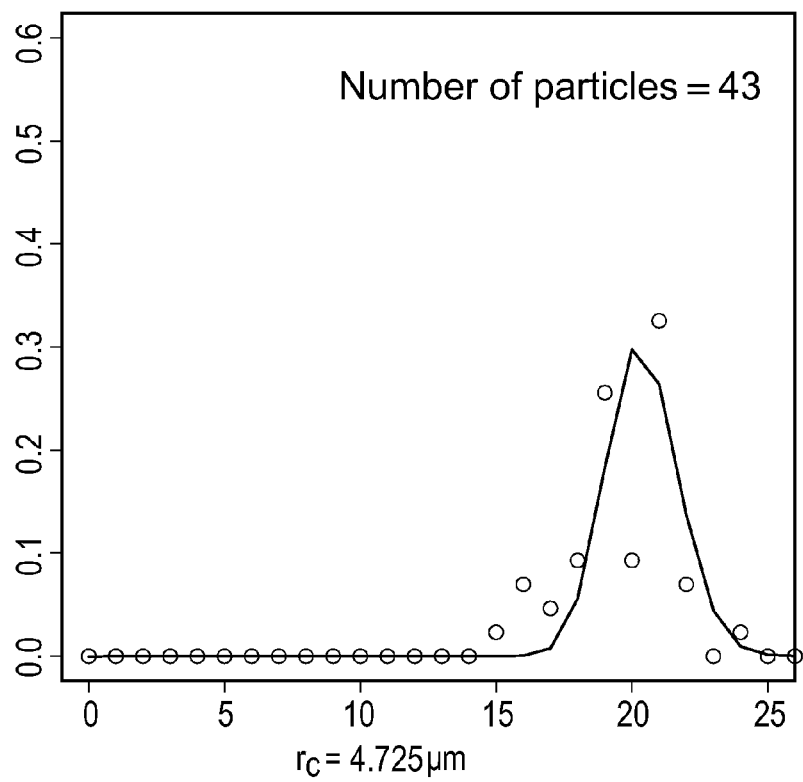
Figure 10W:
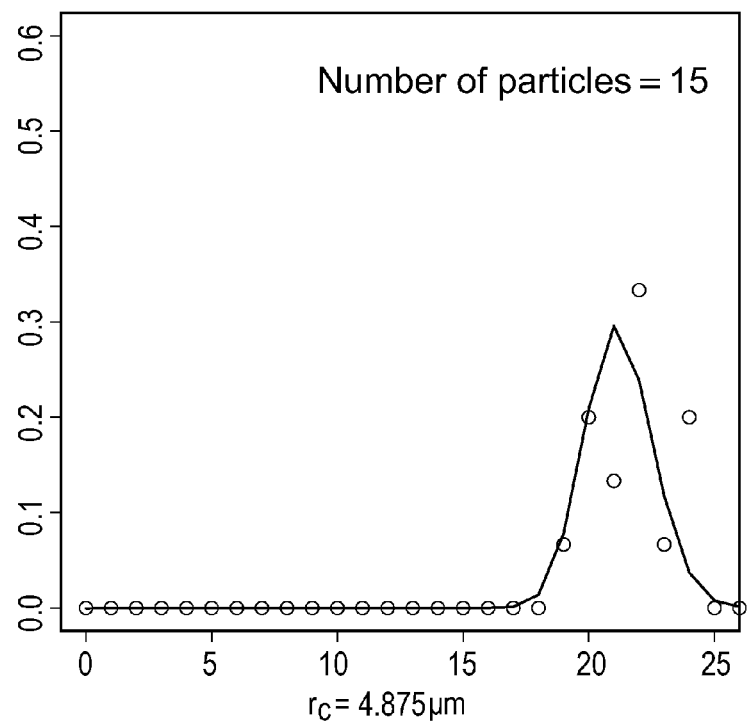
Figure 10X:
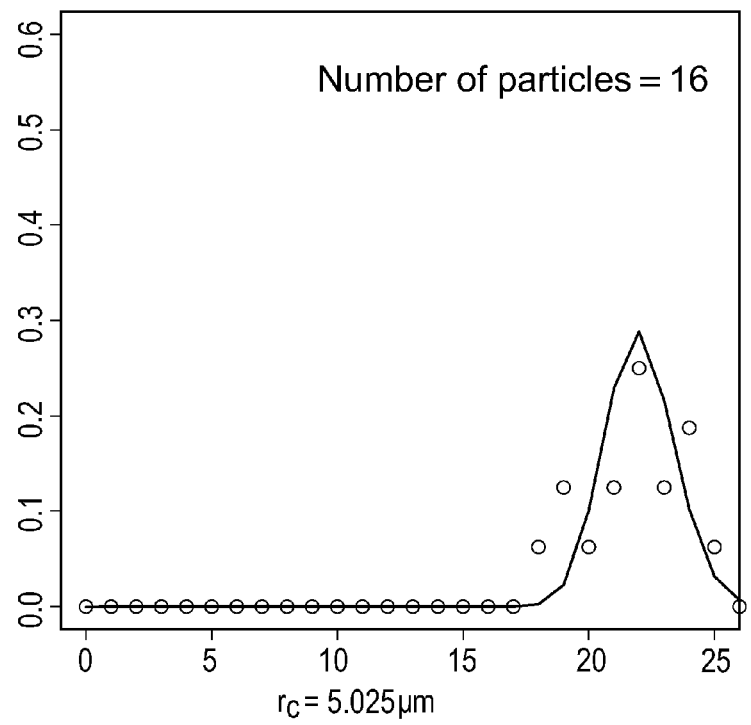
Figure 10Y:
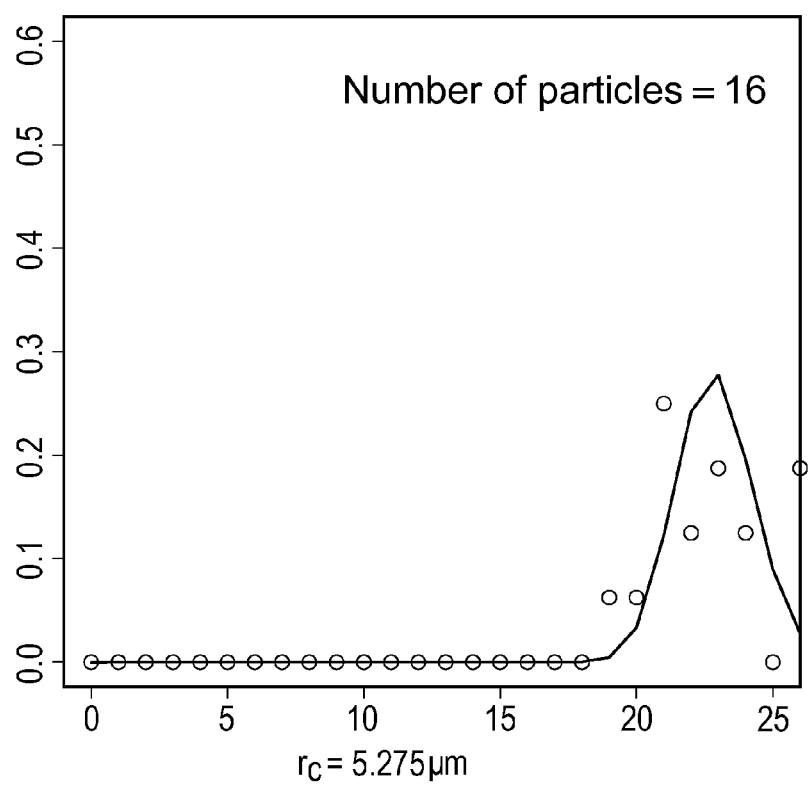
Figure 11A:
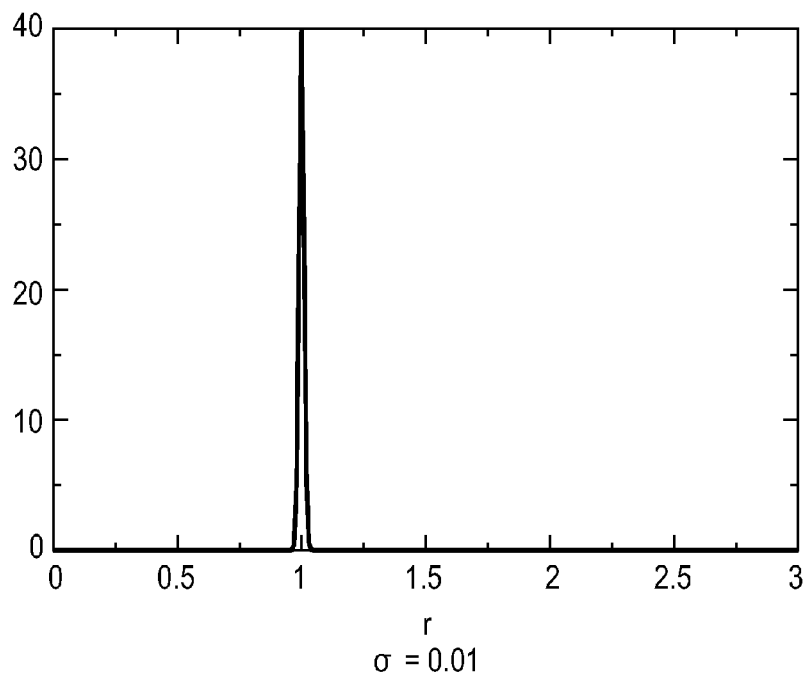
Figure 11B:
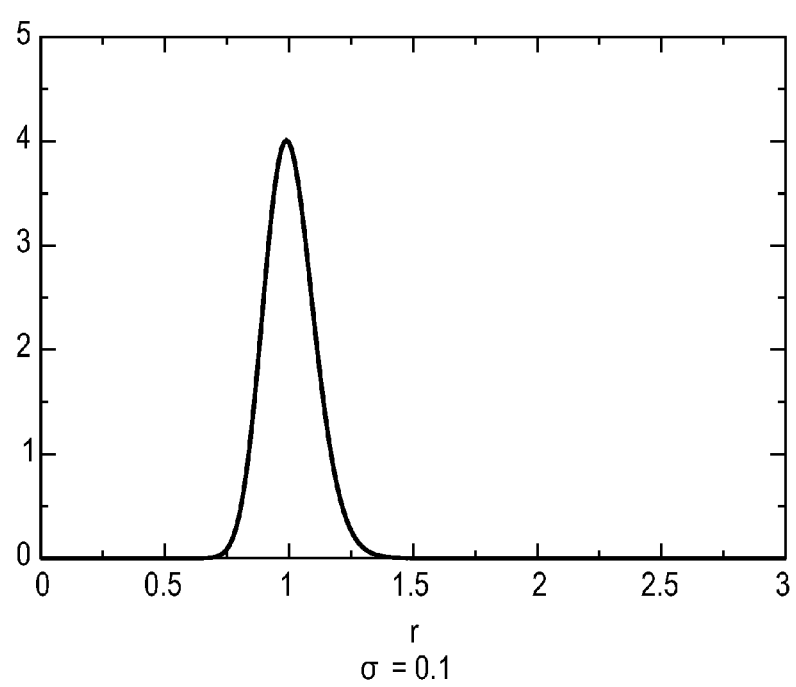
Figure 11E:
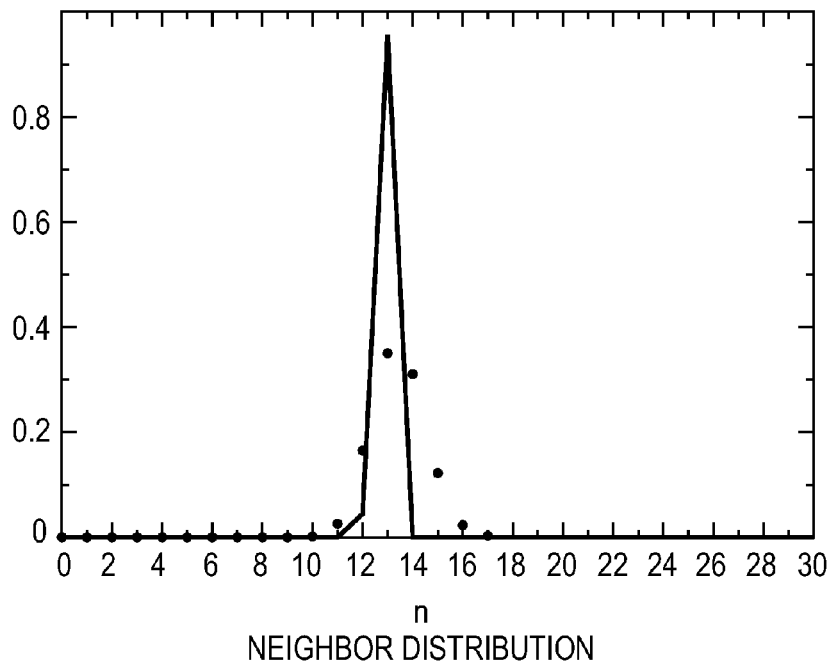
Figure 11F:
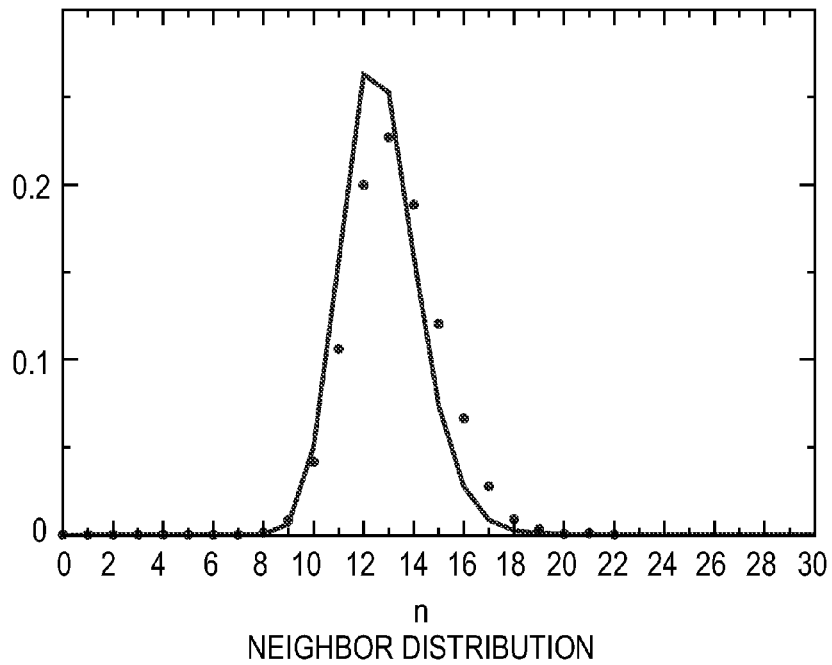
Figure 11G:
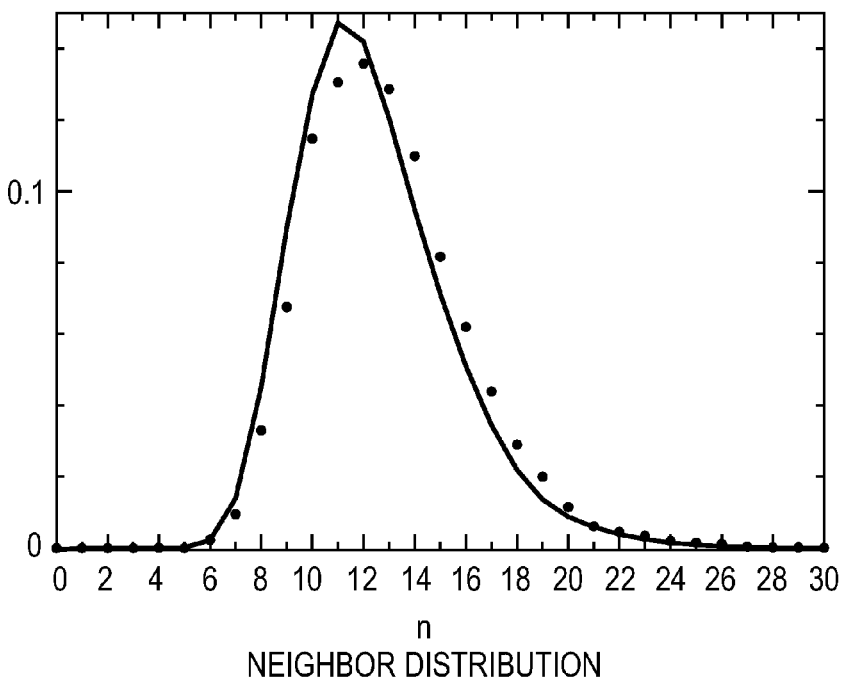
Figure 11H:
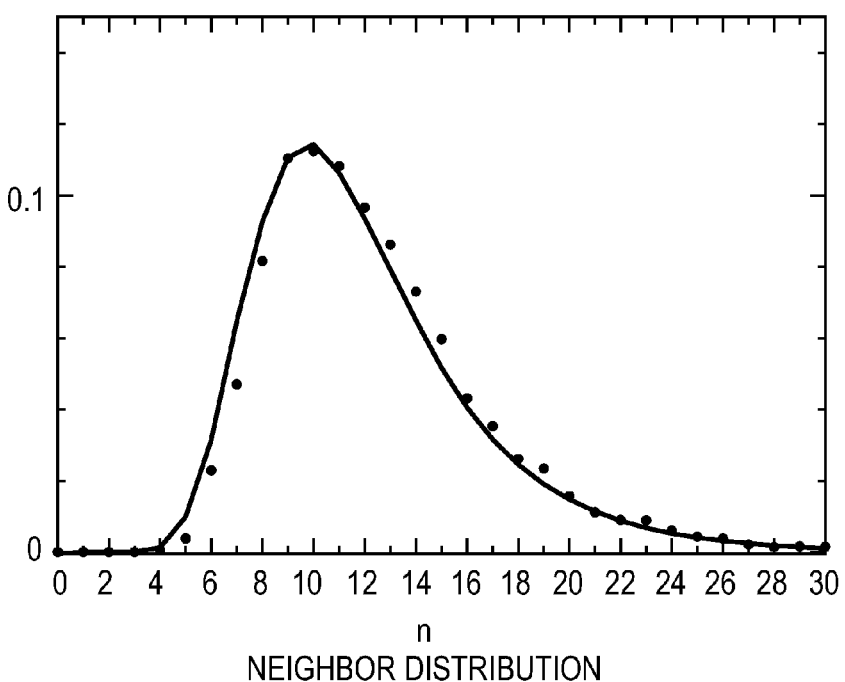
Figure 11K:
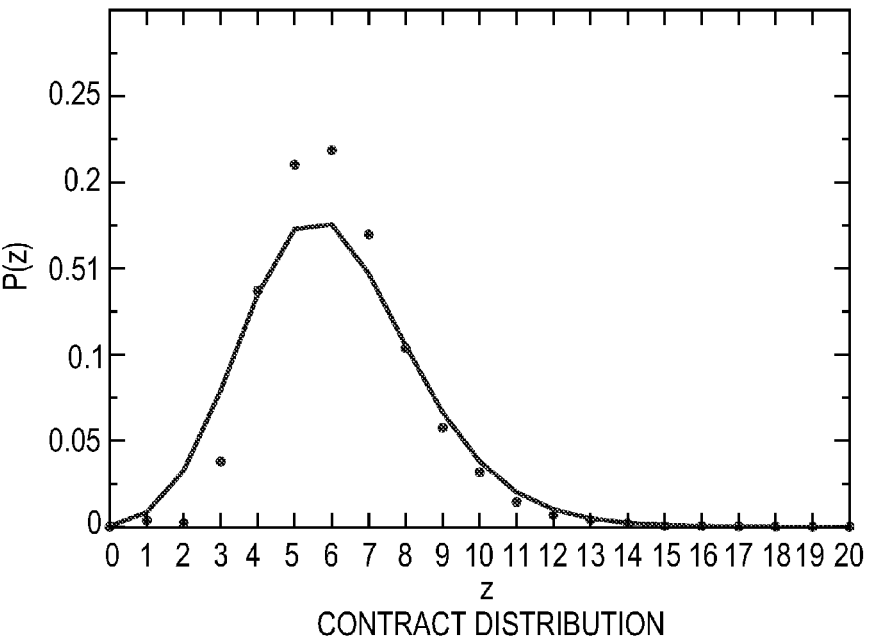
Figure 11L:
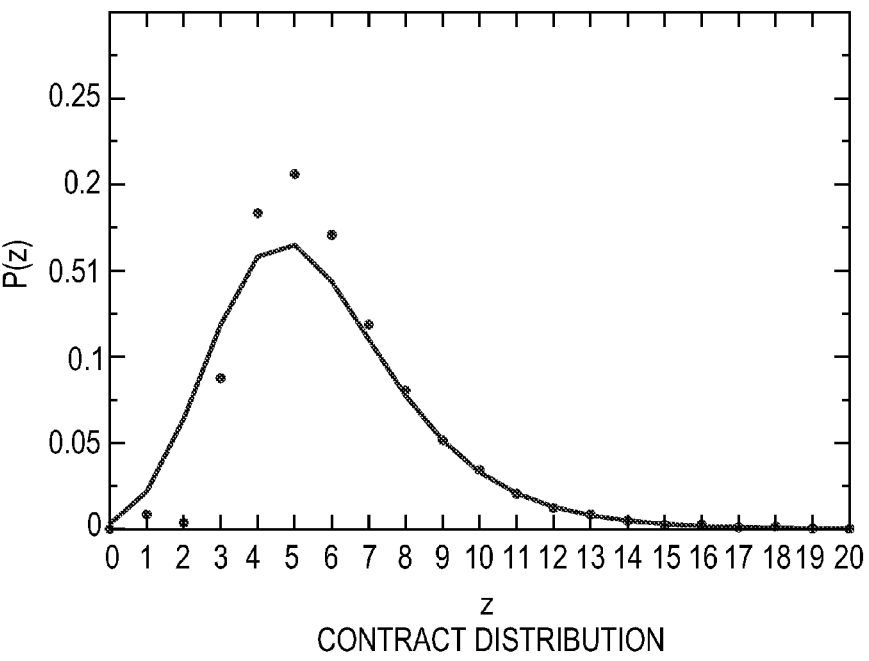
Figure 13B:
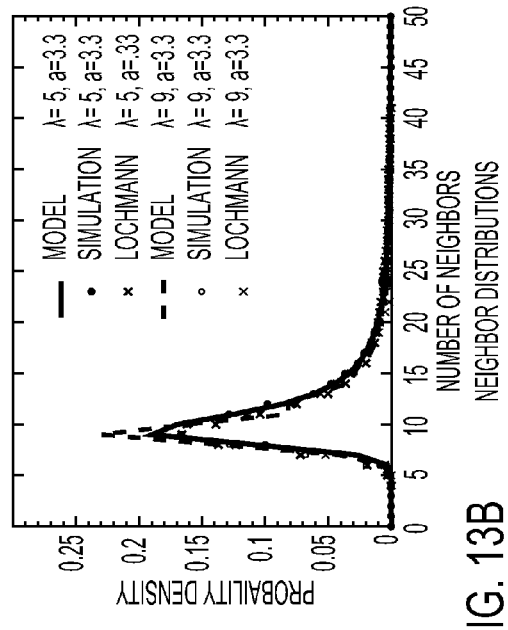
Figure 13D:
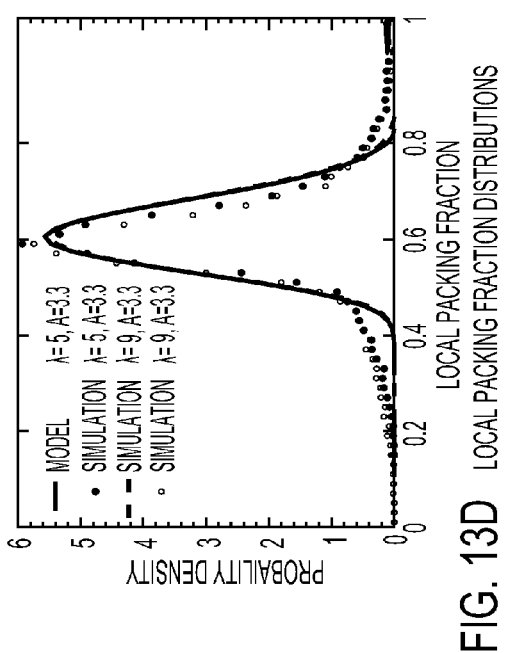
Figure 13A:
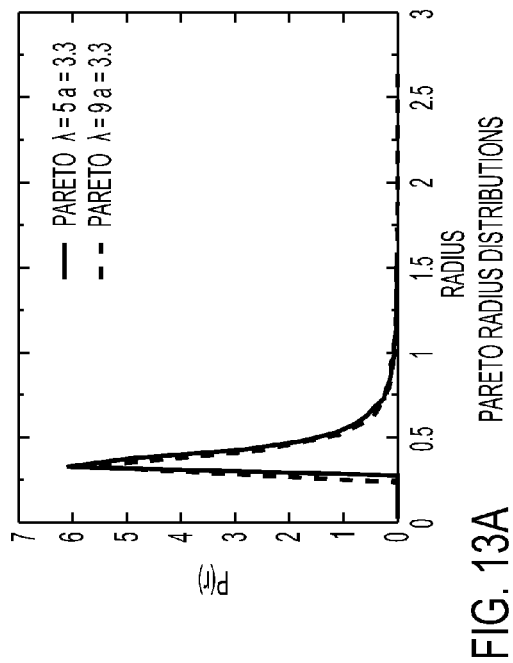
Figure 13C:
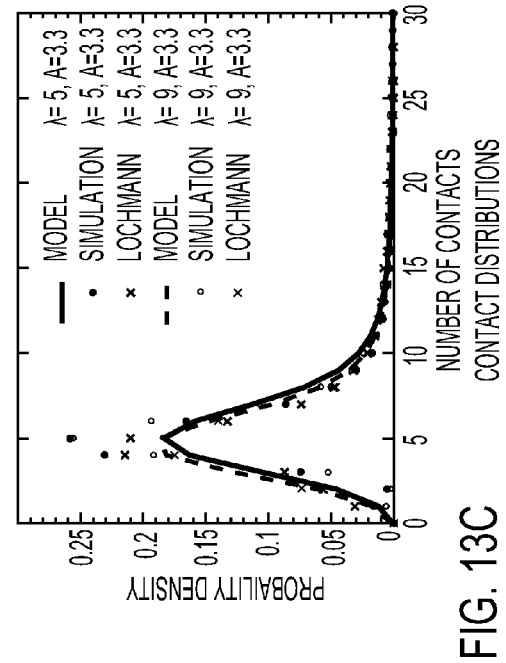

plain line: model. Dots: experiments; the $r_c$ value for each figure is indicated below each figure;

FIGS. 9A-9Y show the evolution of the contact number $r_c$, P(z|$r_c$) for different; $r_c$. plain line: model. Dots: experiments; the $r_c$ value for each figure is indicated below each figure;

FIGS. 10A-10Y show the evolution of the Neighbour number distribution for a given $r_c$, P(n|$r_c$) for different plain line: model. Dots: experiments; the $r_c$ value for each figure is indicated below each figure;

FIGS. 11A-11L shows the comparison between model estimations (plain lines and simulations (dots);

FIGS. 12A-12D show simulated radius distributions (a) and the corresponding probability densities for (b) the number of neighbours, (c) contracts, and (d) the local packing fraction; model (plain line), numerical simulations (dots) and Lochmann et al. data (crosses);

FIGS. 13A-13D show simulated radius distributions with 13A and the corresponding probability densities for 13B the number of neighbours, 13C contacts, and 13D the local packing fraction; model (plain line), numerical simulations (dots) and prior art Lochmann et al. data (crosses).

DETAILED DESCRIPTION OF PREFERRED EMBODIMENTS

Previous studies on the jammed packing state of particulate compositions include the characterization of the network of forces, the microstructure, and effects of particle composition and packing history. In the following we visualize three-dimensional random packings of frictionless emulsion droplets using confocal microscopy to characterize the geometry and connectivity of the packing. FIG. 1A presents an image of a fluorescently labeled oil-in-water emulsion, creamed under gravity to form the mechanically stable random pack, as described in the methods section. The confocal data are preferably analyzed using a deconvolution technique to extract the radius and position of each droplet with subvoxel accuracy of about 1% of the average particle size. We calculate the probability distribution of radii, P(r), shown in FIG. 1B, exhibits a width of 23% of the mean radius. In order to characterize the local neighborhood of each particle, we tessellate the packing using the navigation map, an extension of the Voronoi map to polydisperse systems, with each point in free space allocated to the particle whose surface is closest to it, as shown in FIG. 1C. Two particles are said to be neighbors if their corresponding cells share a common interface in the navigation map. Each cell is gray scale according to the number of neighbors (n) around the central particle, ranging from 4-30. This wide range arises from the polydispersity of the sample and stands in contrast to the narrow range of interest neighbors, typically from 12-17.

A subset of the neighbors is in contact with the central particle and therefore capable of transmitting forces. The resulting force network gives rise to the mechanical stability of the packing. In the confocal images as seen in FIG. 1A, the points of contact between particles are self-consistently determined by the geometric overlap of spheres that reconstruct the particles and an intensity enhancement owing to the fluorescence of Nile Red dye. (FIG. 1A) We measure the mean number of contacts, also known as the coordination number, to be $\langle z \rangle = 6.3 \pm 0.3$, in good agreement with $\langle z_{iso} \rangle = 6$, required for required for isostatic mechanical equilibrium. A slight discrepancy may be expected owing to the small deformation of the droplets.

Figure 1D:
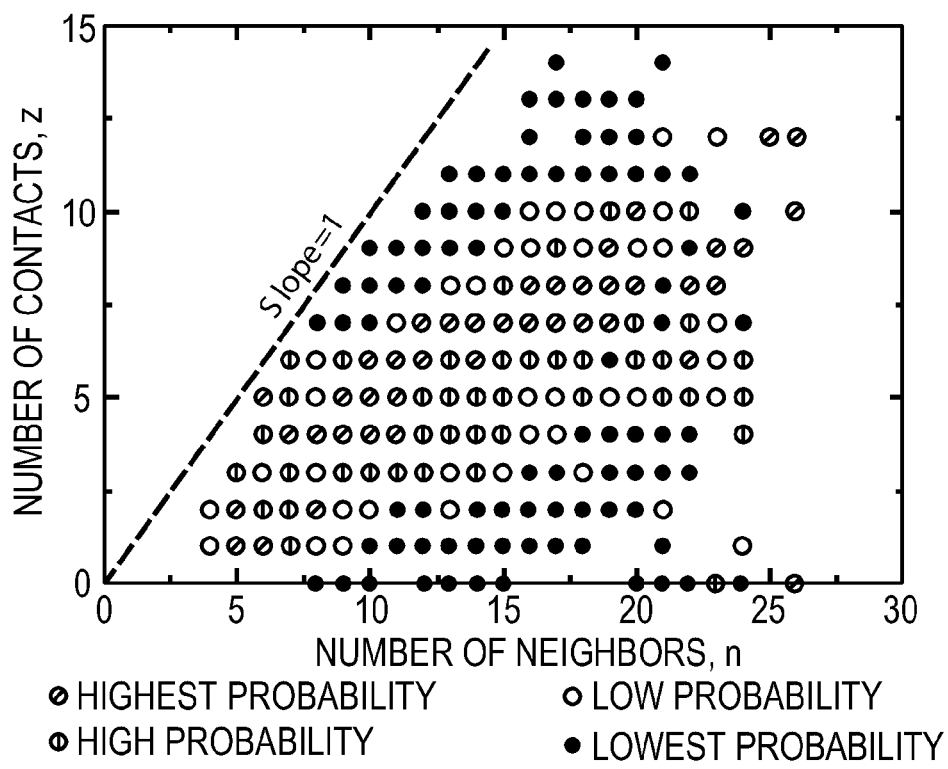
FIG. 1D shows for a given "n" value the number of contacting neighbors z shown as a scatter plot with the range from black to open circle indicating an increasing probability of finding a particle with z contacts.
Figure 1E:
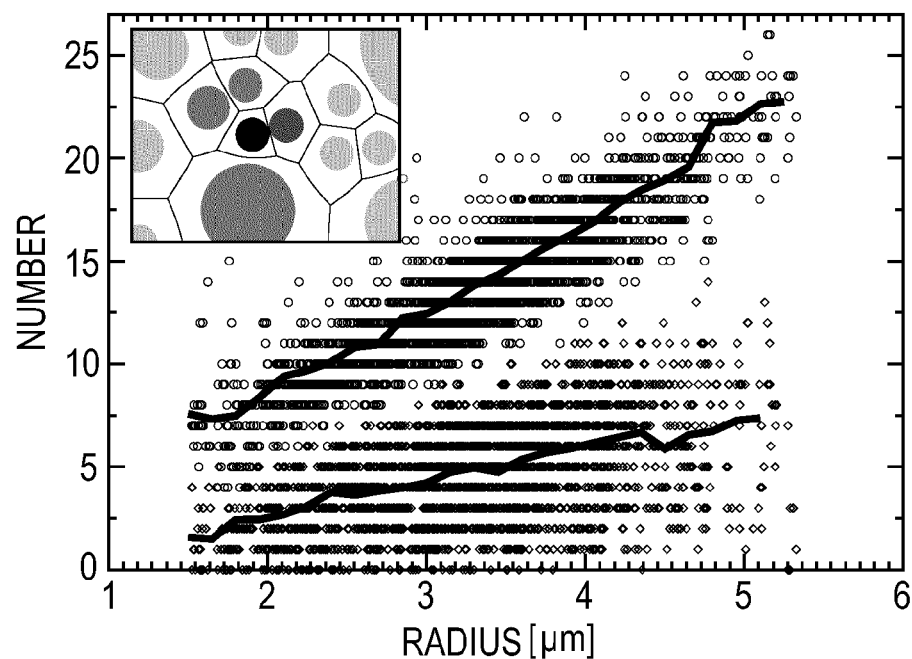
FIG. 1E indicates a schematic inset plot showing that neighbors of a droplet (black) can be in contact or just share an interface (gray) the main scatter plot of FIG. 1E shows fluctuations in number of contacts z and neighbors n with droplet size while average values increase monotonically (black lines).

While the global constraint of isostaticity is satisfied, the number of neighbours n and contacts z around each particle fluctuates significantly within the packing. FIG. 1D shows that for each n, the number of contacts z can take any value between 0 and n, which suggests that z is randomly distributed. In addition, for particles with more neighbours the most likely number of contacts increases, indicated by the coded probability map in FIG. 1D. Moreover, both n and z increase with the radius r of the central particle, as shown in the scatter plot in FIG. 1E. This makes sense, as larger articles have more surface area available on which to fit neighbours.

To understand these observations, we consider the packing problem from the granocentric point of view of a single article in the bulk, exemplified by the particle marked by a star in the confocal image in FIG. 1A. We propose a granocentric model for random packing, initially achieved by the formation of a set of neighbours, followed by the creation of contacts. This model allows for a definition of a local cell, giving access to the local packing fraction.

Figure 2A:
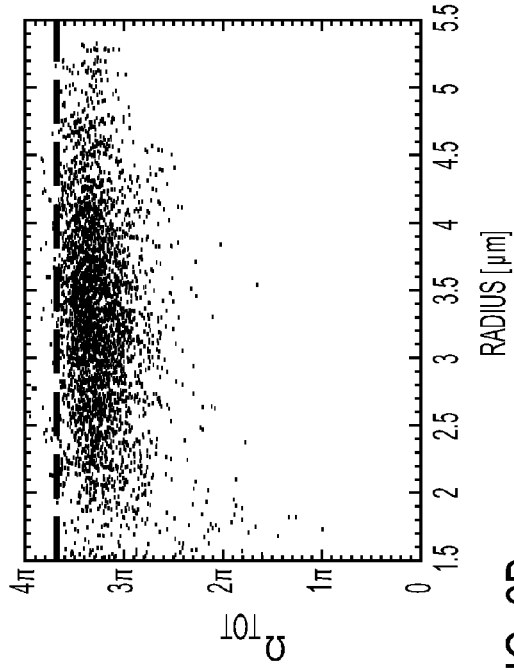
FIG. 2A illustrates a granocentric view of random packing wherein neighbors of the test particle shown in FIG. 1A are shown to screen a central particle from view in the inset arrangement, each neighbor occupying a solid angle $\omega$ shown by the gray scale coordinated staircase summary to $\Omega_{tot}$.
Figure 2B:
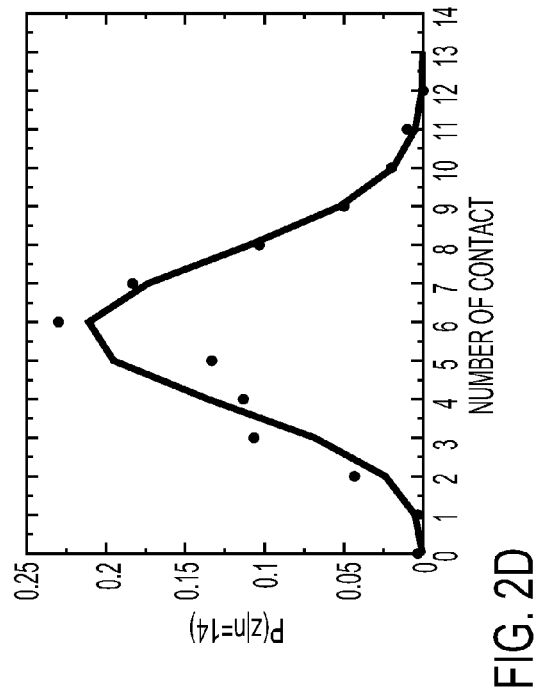
FIG. 2B shows a scatter plot of $\Omega_{tot}$ for each particle in the packing arrangement and shows weak dependence on $r_c$ and nearly all points lie below the predicted maximal solid angle $\Omega_{max}=3.68\pi$ (see dashed line)

The starred particle in FIG. 1A is surrounded by 13 nearest neighbours. The space that each neighbour occupies depends on its size relative to the central particle. The space occupied by each neighbour around a central particle is characterized by the solid angle v it subtends (FIG. 2A). Using this geometric description, we remove a trivial dependence of local packing on the central particle radius, which represents an important simplification. As shown in FIG. 2B, the packing of the neighbours precludes the addition of another neighbouring particle because there is a limited amount of available solid angle around the central particle, of radius $r_c$. This suggests an upper limit $\Omega_{max}(r_c)$ on the available solid angle.

Figure 2C:
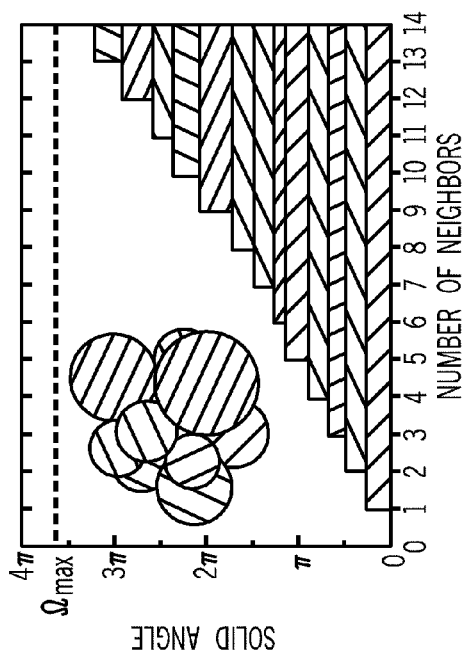
FIG. 2C shows a plot of mean ratio of number of contacts to neighbors ($p=\langle z\rangle/\langle n\rangle$) and is independent of $r_c$ with a value of p=0.41.

We therefore model the formation of a set of n nearest neighbours around a central particle of radius $r_c$ as a random selection of neighbours and a summation of their respective solid angles up to a threshold $\Omega_{max}(r_c)$. It follows that n is the number of particles needed to reach, without exceeding, $\Omega_{max}(r_c)$. Following ref 14, we ignore all neighbour-neighbour correlations by neglecting relative positions of neighbours on the surface of the central particle. The sizes of each successive neighbour are therefore statistically independent and identically distributed. The formation of a set of neighbours thus corresponds to the first passage of a directed one-dimensional random walk, with steps given by the solid angles of the nearest neighbours (FIG. 2C).

In order to describe all the properties of a packing, knowledge of nearest neighbours must be supplemented by knowledge of the contact network responsible for mechanical stability. As noted in FIG. 1D, only a fraction of the n nearest neighbours are in contact with the central particle. The fluctuations in z shown in FIG. 1E suggest that contacts are randomly chosen among neighbours. We model the selection of contacts by Bernoulli trials with success rate p($r_c$), thereby neglecting all possible collective behaviour. Thus the distribution of the number of contacts z for a given number of neighbours n, P(z|n), is a binomial distribution.

We have introduced two processes determining the connectivity of experimental packings. They are further characterized by fluctuations in the local packing fraction, which is relevant to global properties such as permeability and yield stress. The local packing fraction $\phi_{local}$ is defined as the ratio of the particle volume $V_{particle}$ to the cell volume $V_{cell}$. As our granocentric model does not include information on neighbour positions, it is not possible to use the experimental definition of a cell in this framework. Instead, we use an effective definition for the local cell incorporating two salient physical features of the experimental cell: first, a particle with more neighbours will have a higher $\phi_{local}$; second, for a given number of neighbours a particle with more contacts will have a higher $\phi_{local}$. Therefore, we approximate the cell volume as the sum of the volume of the central particle plus the volumes contributed by a portion of space between the central particle and each of its neighbours (see FIG. 3C inset; a more complete description is given in Methods). The differing contribution to the cell volume by the neighbours and contacts is described by an effective surface-to-surface distance δ, for non-contacting neighbours.

Thus, the statistical model reduces the packing problem complexity to two independent random processes at the single-particle level: first, the formation of a set of nearest neighbours is effected by assuming that the neighbours are chosen independently; second, the selection of contacts is assumed to be independent. The local definition of a cell provides further access to local packing fraction fluctuations. Whereas previous geometric models have predicted the average coordination number and density of discrete multicomponent systems, by mapping the packing problem onto the first passage of a random walk we are able to analytically study continuous distributions of radii and their influence on the full distributions of the number of nearest neighbours, coordination number and local density. Importantly, our model exploits the previously neglected observation that not all particles touch their neighbours.

Figure 2D:
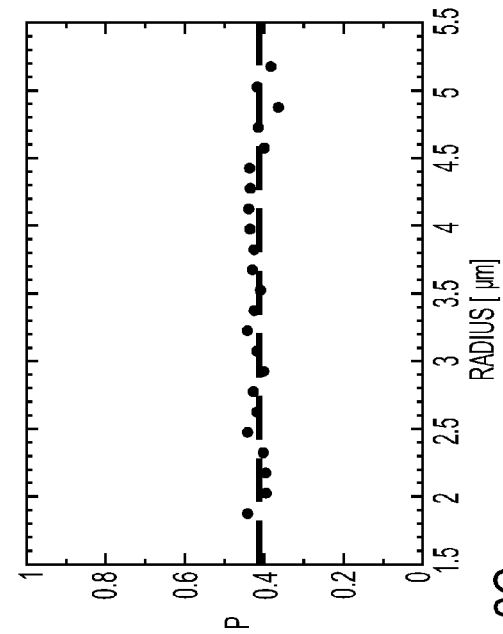
FIG. 2D shows a plot of contacts, P(z/n), versus number of contacts for all particles with a given number of neighbors, n, which is consistent with a binomial distribution with probability, p.

Overall, the model introduces three parameters, $\Omega_{max}(r_c)$, $p(r_c)$ and δ, with different physical interpretations. The central parameter of our model, $\Omega_{max}(r_c)$, is the available solid angle around a particle of radius $r_c$. It is an effective parameter whose value encompasses the details of the packing structure, such as polydispersity, steric effects, and long range correlations. For example, the available solid angle of a face-centred-cubic crystal is $3.2\pi$ owing to the space between neighbours, whereas the total solid angle around a sphere is $4\pi$. As described hereinafter, the tools of random walks yield a functional relationship between the average number of neighbours around particles of radius $r_c$ and the threshold $\Omega_{max}(r_c)$. Using the experimental average value of n for each radius $r_c$ presented in FIG. 1e, the model estimates $\Omega_{max}(r_c)$. Remarkably, the experimentally determined values of $\Omega_{max}(r_c)$ are independent of $r_c$ to within $\pm 0.15\pi$ around a value of $\sim 3.68\pi$. Thus, the ratio of the occupied surface area to the total surface area of the central particle does not depend on the size of the central particle in this polydisperse sample. The value of $3.68\pi$ is reasonable because it implies that there are unfilled spaces between the neighbours, observed in the example of FIG. 2B. The interpretation of $\Omega_{max}$ as an upper limit is tested by directly measuring whether the total solid angle $\Omega_{tot}$ around each particle lies below $\Omega_{max}$. FIG. 2D shows that 98% of the measured values are bounded by the estimated value of $\Omega_{max}$, consistent with the proposed model assumptions.

To select contacts among neighbours, we introduced the success rate $p(r_c) = \langle z|r_c\rangle/\langle n|r_c\rangle$. There is no reason to suspect that this probability $p(r_c)$ should be independent of particle size. However, our measurements in FIG. 2E reveal that this average fraction of neighbours in contact is always $p(r_c) \approx 0.41$. This independence represents an important simplification and enhances the appeal of the model. We test the assumption that contacts are chosen independently by examining the experimental distribution of z for a given n. As seen in FIG. 2F for n=13, this distribution is captured by a binomial distribution with p=0.41.

The final parameter in our model characterizes the local cell definition. The mean radius is a natural length scale in our system, which we use to quantify the effective distance δ. We introduce a dimensionless parameter α such that $\delta = \alpha\langle r\rangle$, assumed to be the same for every non-contacting particle. We choose α=0.30 to match the experimentally measured mean local packing fraction. Thus, gaps between the neighbours are significantly smaller than the average particle size, consistent with the notion that one cannot fit further particles between a particle and its neighbour.

Figure 3A:
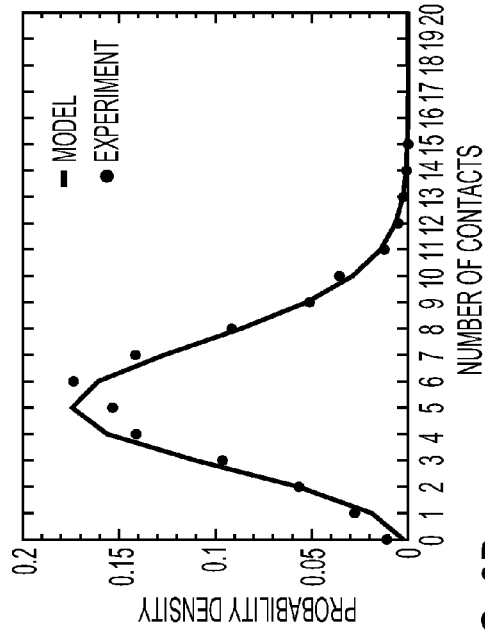
FIG. 3A is a plot of neighbors directly obtained from a statistical model versus experimental data.
Figure 3B:
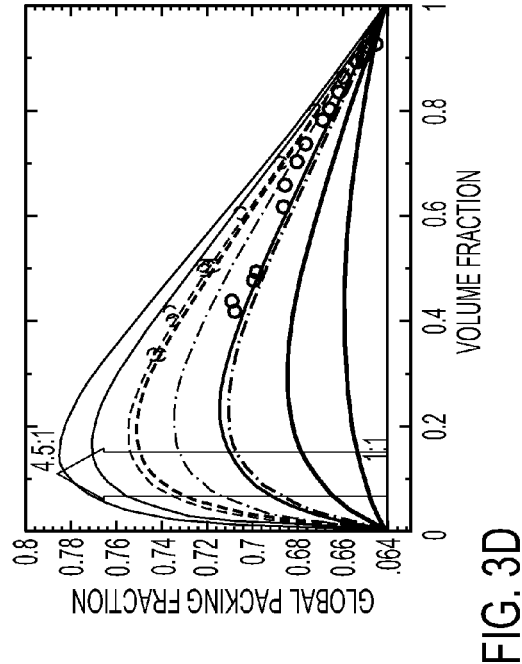
FIG. 3B illustrates a plot of probability densities of contacts obtained from a statistical model versus experimental data.
Figure 3C:
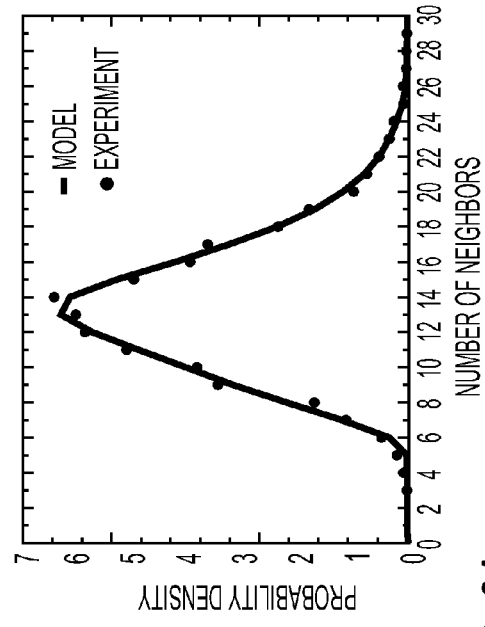
FIG. 3C in the inset portion shows volume contributions to a cell in the model and the probability density of the local packing factors obtained from the model compared to experimental data which can be compared to the navigation map of FIG. 1C.

Using this framework, we calculate distributions of n, z and $\phi_{local}$, and compare them with experimental results to test our model. Using the equations presented herein, we demonstrate in FIG. 3C that the predicted distributions are in excellent agreement with the experimental data. Furthermore, the full distributions as a function of the radius of the central particle are also shown to be in agreement (See FIGS. 5 to 10Y). These results validate the model as a tool to predict the effects of polydispersity on random packings. As shown in FIG. 3B, both the experiments and the model show that 18% of particles are mechanically unstable, with fewer than four contacts. These particles, known as 'rattlers', arise naturally from the random packing processes of our model, in contrast to existing models that exclude rattlers and only focus on the network of contacts. The agreement between model and experiment for local quantities n, z and $\phi_{local}$ shows that the model quantitatively captures the local packing structure. The applicability of the model to packings with other size distributions is presented hereinafter and FIGS. 11A to 13D. Numerical simulations show that the range of values for each parameter is narrow, but that the parameters are not universal for all polydispersities.

We can extend our local view of packing to predict the global density, a long-standing question in understanding random close packing. The influence of the particle size distribution on global density has many industrial applications, such as predicting the density of dried paint or the density of porous rocks. The global packing fraction is defined as the ratio of the total volume of matter divided by the total volume of the sample. This is translated into our local model as:

$$\phi_{global} = \frac{\langle V_{particle}\rangle}{\langle V_{cell}\rangle}$$

It is important to note that the model value for the global packing fraction is relatively insensitive to the local fluctuations and depends strongly only on α. Using the model definition of the local cell volume, we predict the global density of our packings to within 0.5% of the experimentally measured 66.4%. It is not surprising that this polydisperse packing is denser than its monodisperse counterpart ($\phi_{global} \approx 64\%$), as small particles can pack in the interstices of larger ones.

Figure 3D:
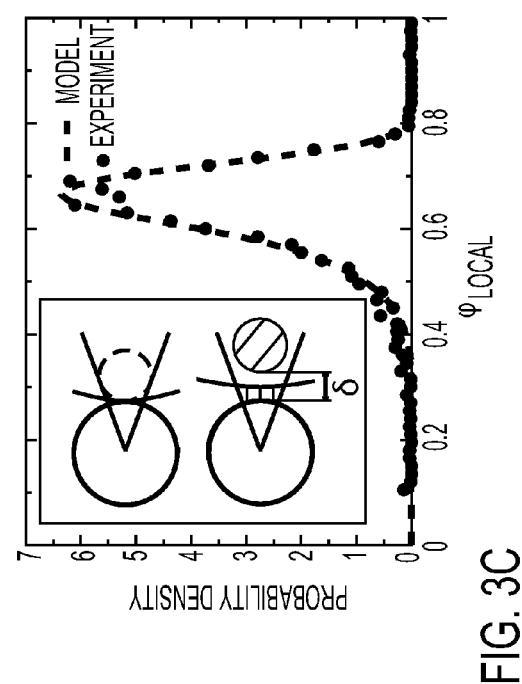
FIG. 3D shows global packing fraction versus volume fraction as determined by model predictions for bidisperse packings of different aspect ratio versus experimental data for size ratios of 2.58:1 and 3.41:1 with the lighter adjacent curves representing size ratios ranging from 1:1 to 4.5:1 in 0.5 increments.

We further probe the predictive power of our model for systems with other size distributions by considering bidisperse packings. In such packings, polydispersity is a function of the size ratio of the two species and the volume ratio of all small particles to all particles. Using the local cell definition with the same parameters as for our experimental system, the model reproduces published experimental data for different volume fractions of small particles and size ratios, even in the limit of the monodisperse case (FIG. 3D). This demonstrates that a local model based on geometric considerations alone provides an effective description of the packing as a whole.

The model accurately characterizes random, polydisperse packings in terms of numbers of nearest neighbours and contacts per particle, fluctuations in local density, and global density of the system. Our experiments reveal that the model parameters, $\Omega_{max}$ and p, are independent of the central particle size, leading to a simple physical interpretation of the mechanism of random packing. From the perspective of each particle, a stable random packing is achieved when (1) the surrounding space is filled with a set of nearest neighbours and (2) some of those neighbours touch the central particle to achieve mechanical equilibrium. This model offers a simplified view of the packing problem, and opens an analytical path to explore the industrially important effects of polydispersity on local and global properties of packings.

It is surprising that such a simple model should describe the random packing of polydisperse spheres. For monodisperse packings, the only source of disorder is positional. Such a system is an archetypal example of a complex system, where correlations between particle positions determine the physical behaviour. In our system, the polydispersity serves as a second source of randomness added to the positional disorder. Our model is able to describe a polydisperse packing because the local source of randomness coming from the distribution of radii, P(r), dominates the positional disorder.

The granocentric model can be used to count the number of equivalent local configurations in disordered packings, and thus may provide a definition for entropy. Thus, we may probe the contention that jammed packings can be described using a thermodynamic approach. Other open questions that extensions to the model could answer include the effects of spatial dimensions and particle shape on packings. We have so far considered purely random packings, but it would be interesting to examine how correlations influence the microstructure, both in the model and in the experiments. This work represents an effective medium model for random close packing, while the determination of model parameters from first principles may provide a route to a complete theory.

The assumption that successive steps in the random walk are independent leads us to use the Laplace transform L. If X and Y are two independent random variables of respective probability density $P_X$ and $P_Y$, then the probability density of the sum $P_{X+Y}$ satisfies $L[P_{X+Y}]=L[P_X]L[P_Y]$. This basic observation, combined with standard probability tools, leads to the main results herein.

Let $$\omega = 2\pi \left(1 - \frac{1}{1+r/r_c}\sqrt{1+\frac{2r}{r_c}}\right)$$

be the solid angle subtended by a particle of radius r on a given central particle of radius $r_c$, where r is drawn from the distribution P(r). We compute $fr_{c(\omega)}$, the probability density of solid angle around the central particle, by a change of variables from P(r). The mean number of neighbours $\langle n|r_c\rangle$ around the central particle of radius $r_c$ is then given by $$\langle n|r_c\rangle = L^{-1}\left[\frac{1}{s}\frac{L[fr_c](s)}{1-L[fr_c](s)}\right](\Omega_{max})$$

where $L^{-1}$ is the inverse Laplace transform with respect to s, the conjugate variable of $\Omega_{max}$. The probability density for a particle of radius rc to have n neighbours given the maximal solid angle $\Omega_{max}$, $P_{neighbour}(n; r_c, \Omega_{max})$, is given by:

$$P_{neighbour}(n; r_c, \Omega_{max}) = L^{-1}\left[\frac{1}{s}L[fr_c](s)L[fr_c](s)^n\right](\Omega_{max})$$

Likewise, the distribution of coordination number z can be computed as:

$$P_{contact}(z; r_c, \Omega_{max}) = L^{-1}\left[\frac{1-fr_c(s)}{s}\frac{(pfr_c(s))^z}{(1-(1-p)fr_c(s))^{z+1}}\right](\Omega_{max})$$

Definition of local cell. The volume of a cell, $V_{cell}$, is defined as $$V_{cell} = V_{particle} + \sum_{j=1}^{z} v_j = \sum_{j=1}^{n-z} v_j^*$$

where $v_j$ is the volume contribution of the jth contacting neighbour and $v^*_j$ is the volume contribution of the jth non-contacting neighbour. Let C be the cone subtended on the central particle by the neighbour particle in contact, and S be the surface of the central particle.

For contacting particles, let H be the surface of the hyperboloid defined by the navigation map of these two particles with surfaces in contact. The volume v is defined as the volume of a region between the central particle and the neighbour that is the portion of C between S and H.

For non-contacting particles, let H' be the surface of the hyperboloid defined by the navigation map of these two particles with surfaces separated by a distance d. The volume v* is then the portion of C between S and H'.

Figure 4:
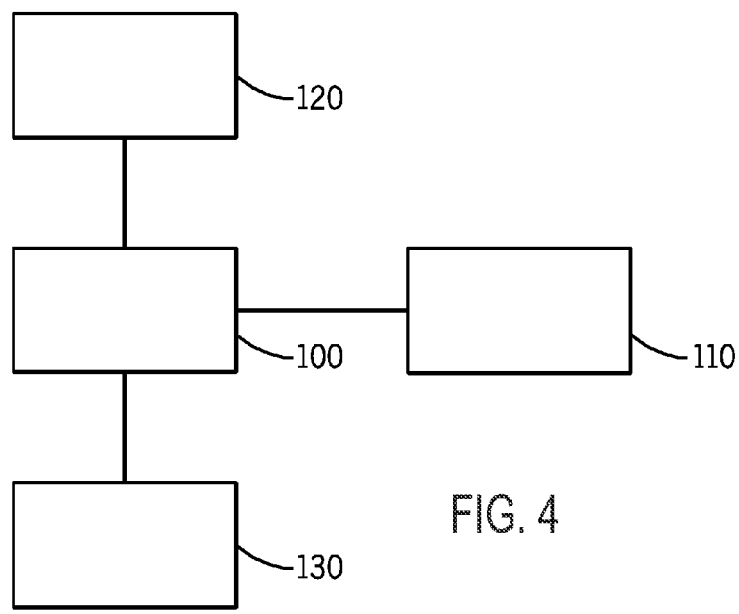
FIG. 4 is a schematic block diagram of a computer system for effectuating the method of the invention.
Figure 5:
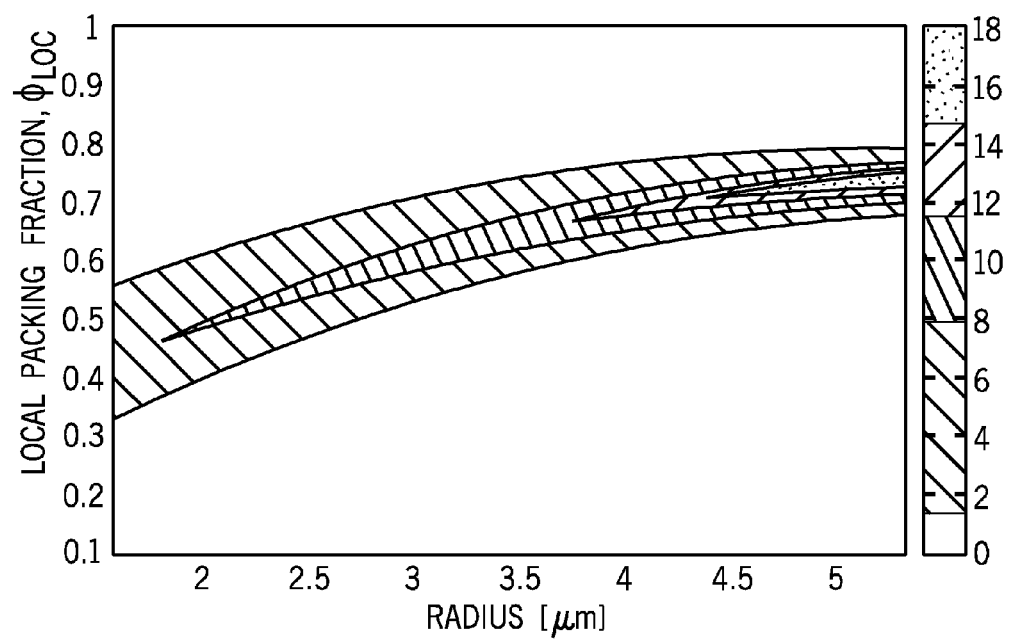
FIG. 5 is a map showing the conditional probability density $P(\phi_{loc}|r_c)$ obtained from the model using $\Omega_{max}=3.68\pi$ and p=0.41, while the circles are the experimental points obtained for the emulsion presented in FIGS. 1A-1E; their area is proportional to the number of observations.
Figure 6:
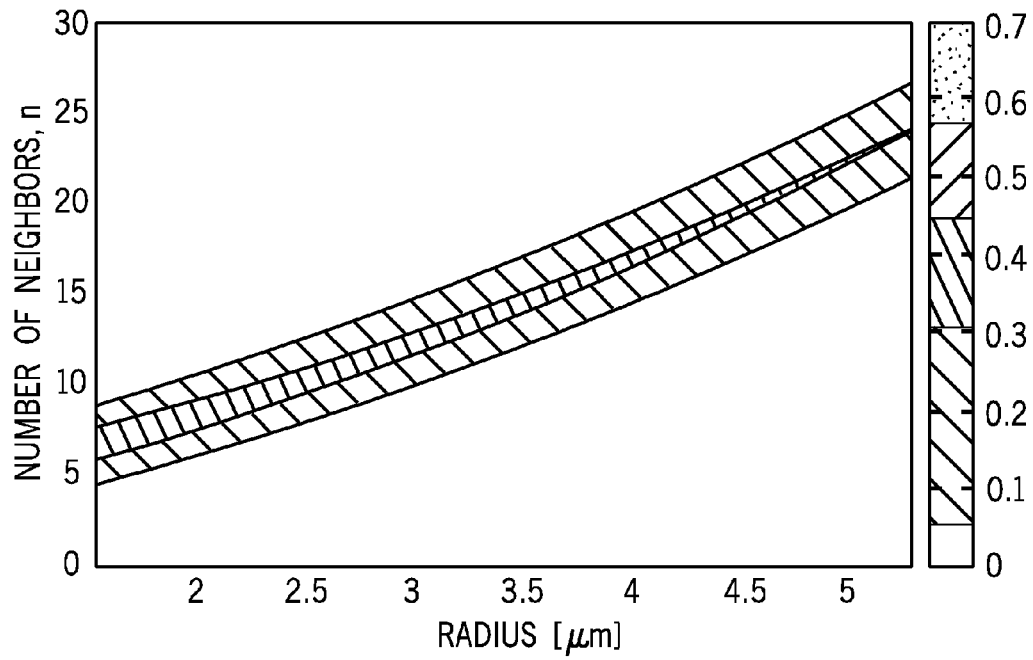
FIG. 6 is a map showing the conditional probability density $P(n|r_c)$ obtained from the model using $\Omega_{max}=3.68\pi$ and p=0.41, while the circles are the experimental points obtained for the emulsion presented in FIGS. 1A-1E' their area is proportional to the number of observations.

The method and system of the invention can be implemented by the computer system shown in FIG. 4. The system includes a computer 100 which can execute a computer readable medium including a computer program, such as computer software, module with instructions embedded in a computer addressable storage medium 110. This medium can be read/writable which enables data to be written thereto and read therefrom. This feature enables a user to perform static or dynamic data analysis; and results of that analysis allow a user to act on that information to process the particulate material by utilizing the characteristics determined, such as the packing property of the material, to carry out at least one of change the physical properties of the material, change the chemical properties of the material, display information about the material, print out for use the characteristics of the material and store for future use characteristics of the material.

In another aspect of the invention the probability densities can be related to dependence on the central particle radius. The model presented allows for the calculation of the conditional probability density of neighbours, $P(n|r_c)$, contacts $P(z|r_c)$, and local packing fraction, $P(\phi_{loc}|r_c)$, for a given central particle radius $r_c$. We integrate these densities against the radius distribution P(r) to obtain the overall distributions, for example:

$$P(z) = \int dr P(z,r) = \int dr P(r) p(z|r)$$

Figure 7:
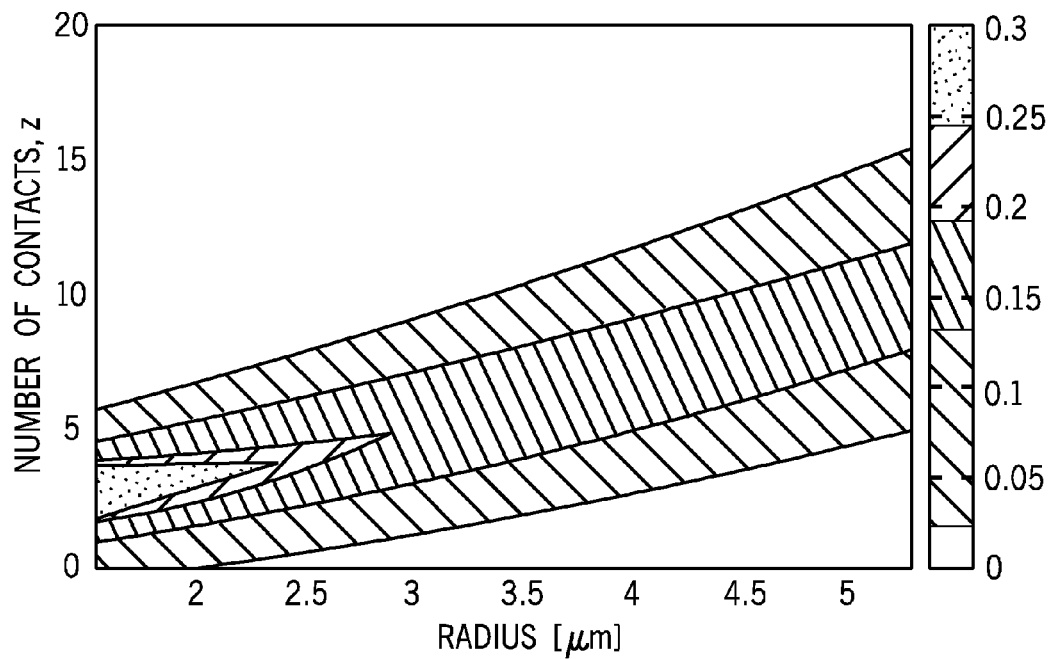
FIG. 7 is a map showing the conditional probability density $P(c|r_c)$ obtained from the model using $\Omega_{max}=3.68\pi$ and p=0.41, while the circles are the experimental points obtained for the emulsion presented in FIGS. 1A-1E; their area is proportional to the number of observations.
Figure 8A:
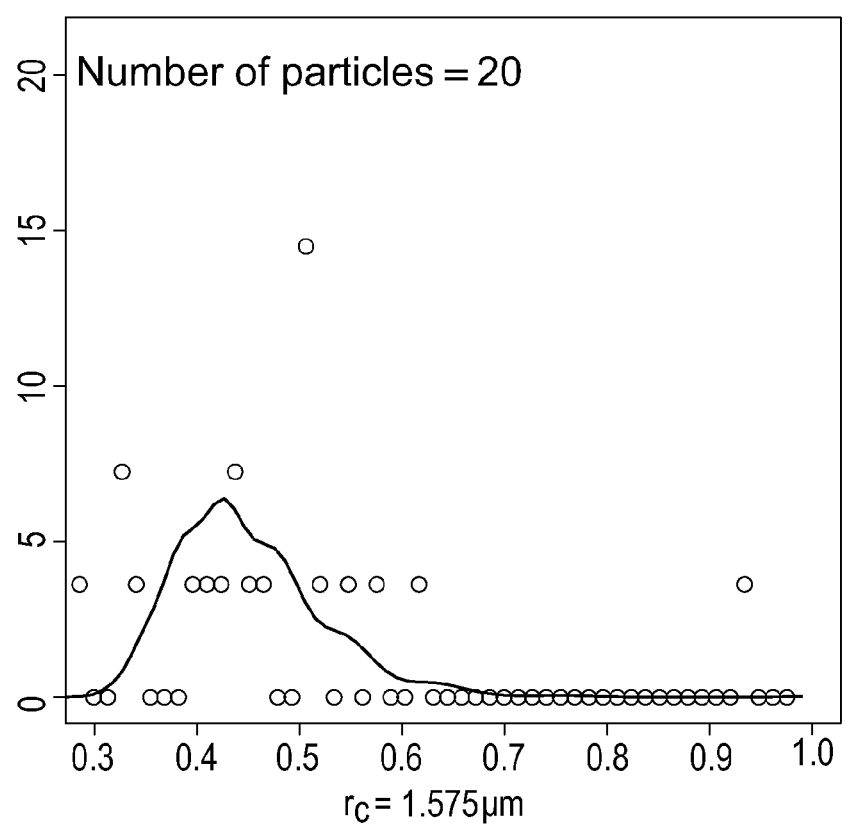
FIGS. 8A-8Y shows the evolution of the local packing fraction distribution for a given $r_c$, $P(\phi|r_c)$ for different $r_c$.
Figure 8B:
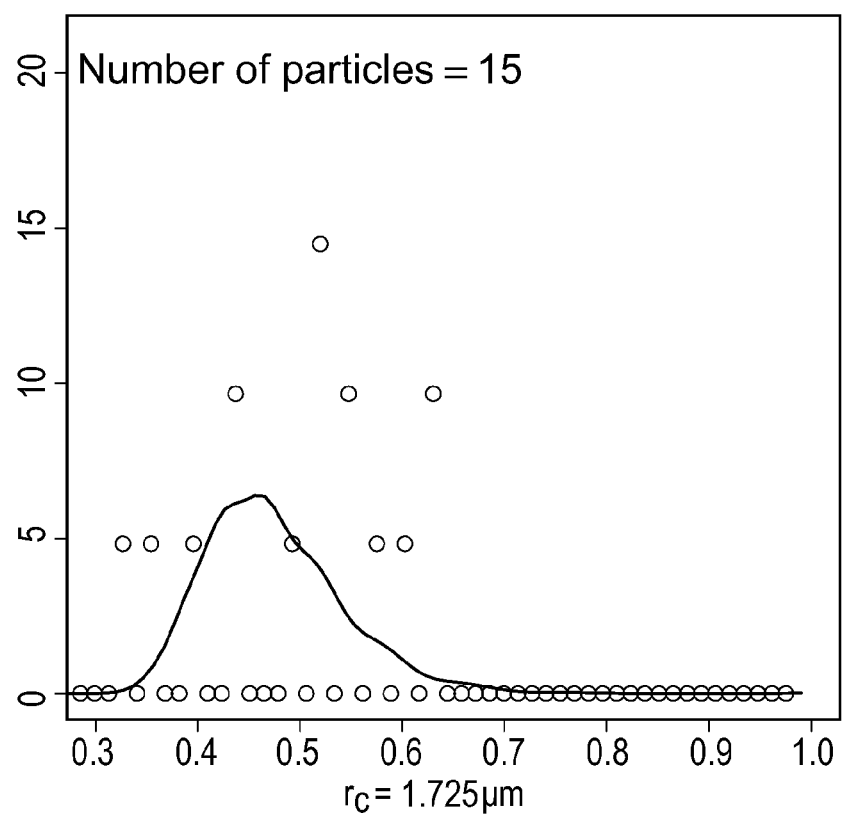
Figure 8C:
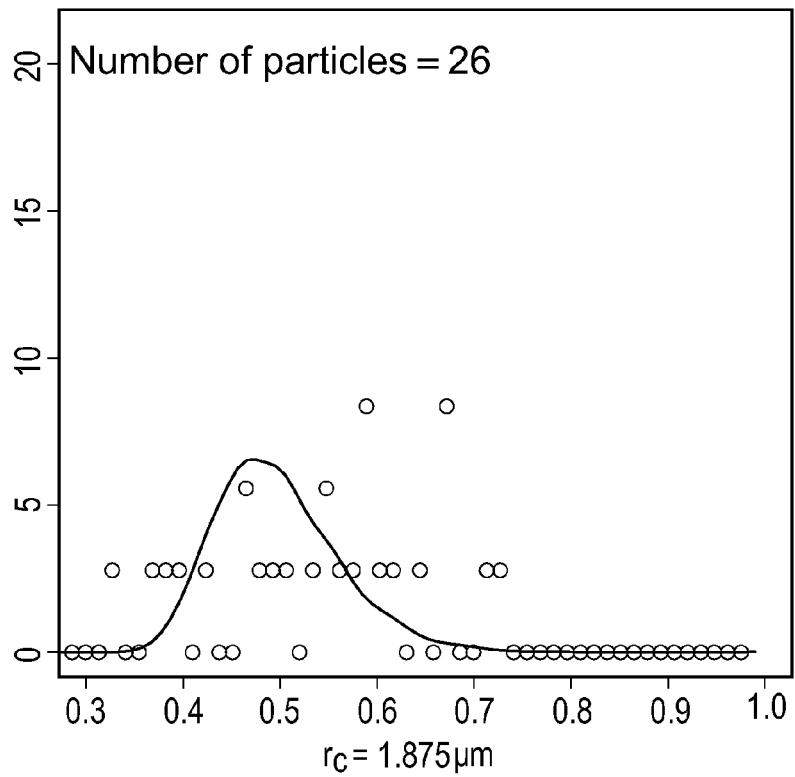
Figure 8D:
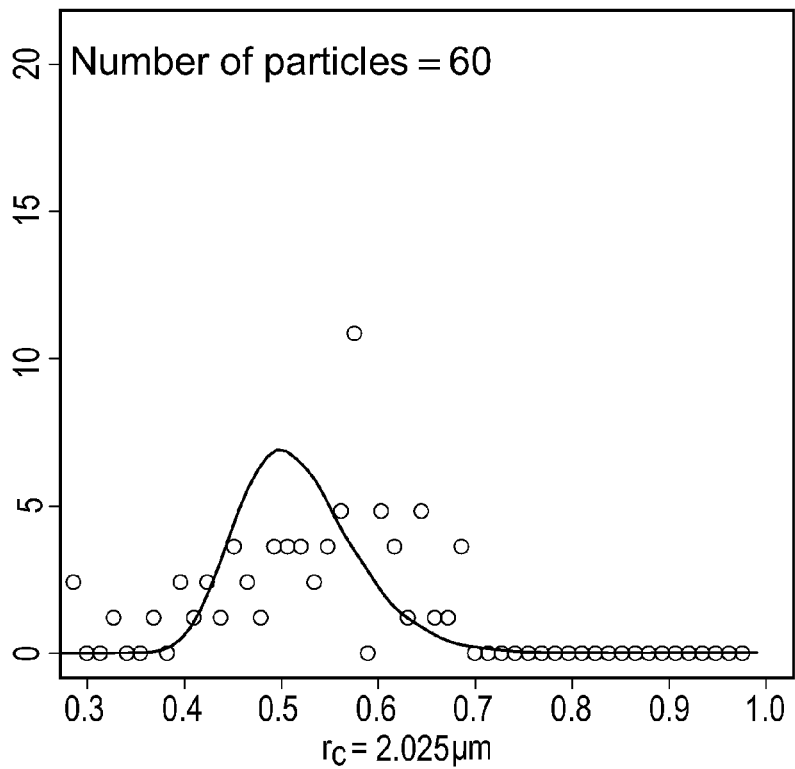
Figure 8E:
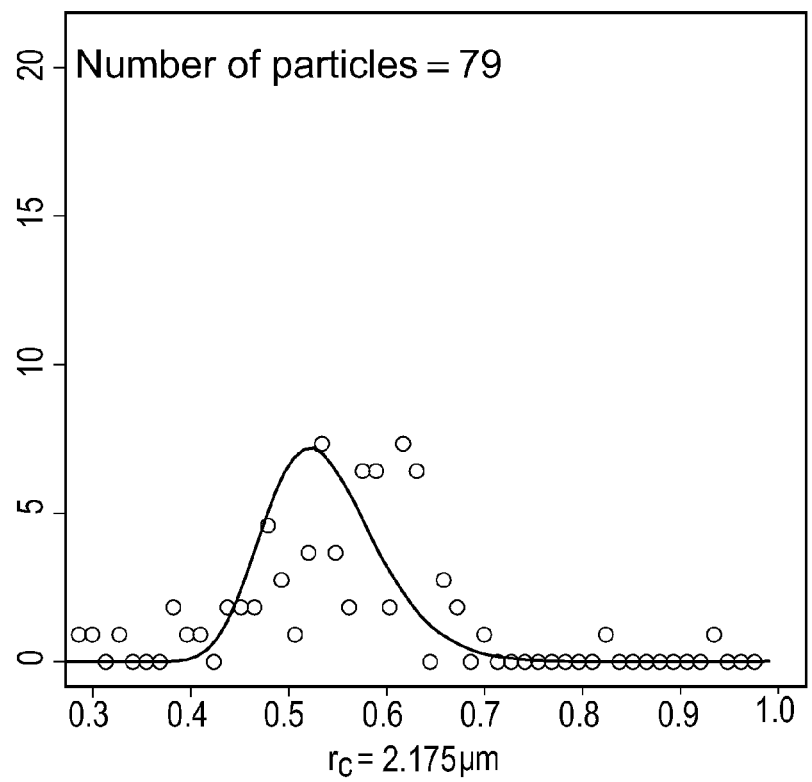
Figure 8F:
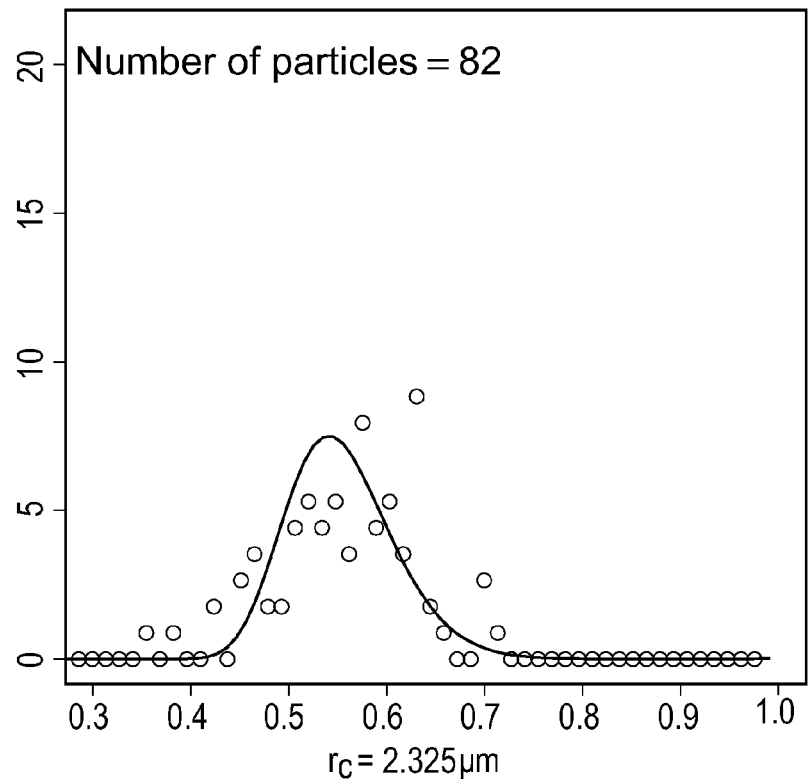
Figure 8G:
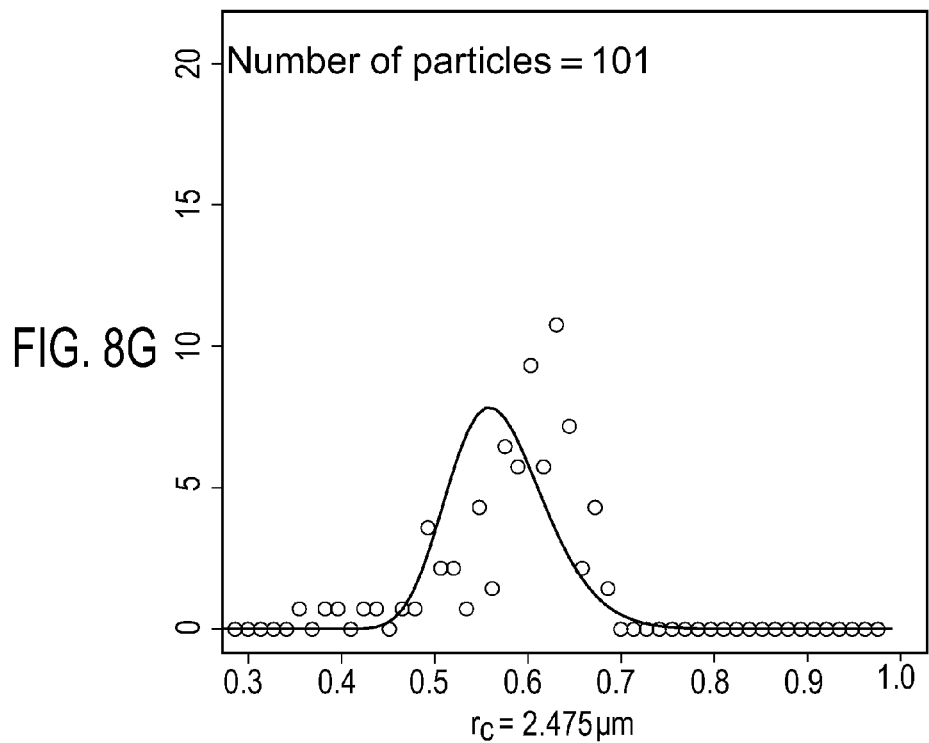
Figure 8H:
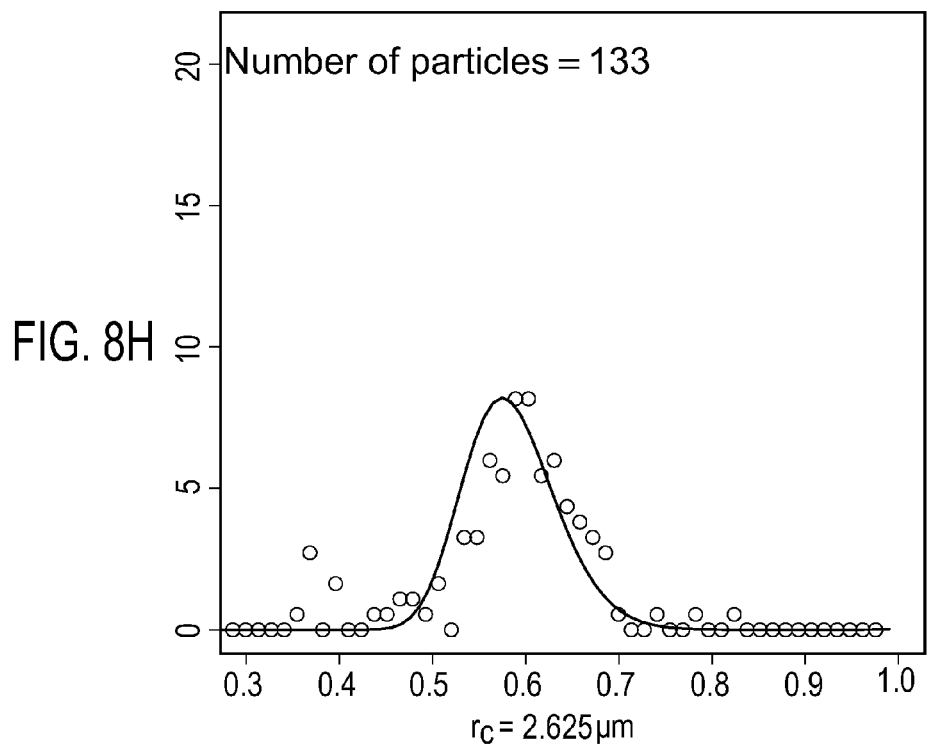
Figure 8I:
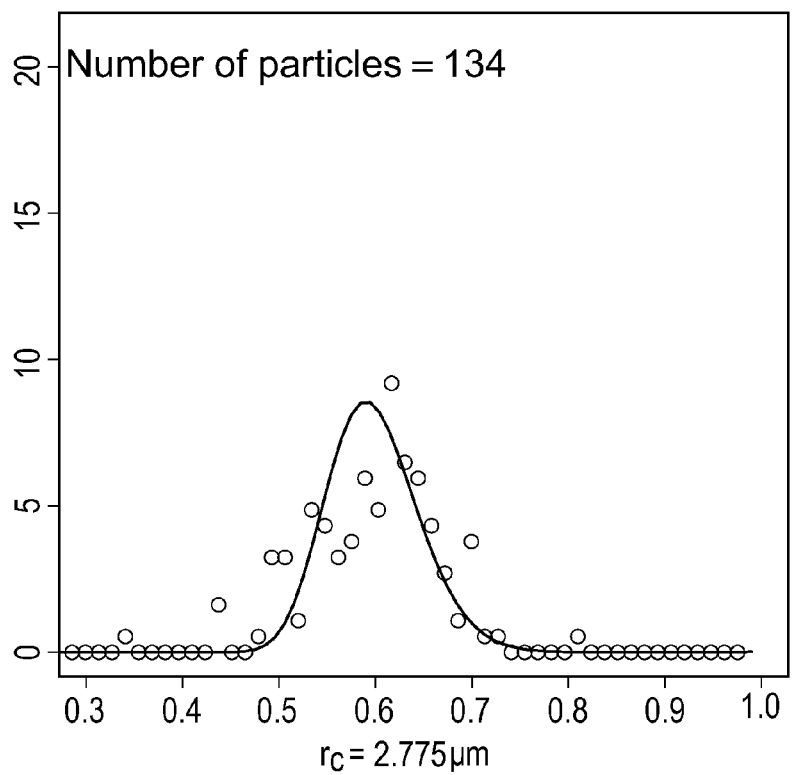
Figure 8J:
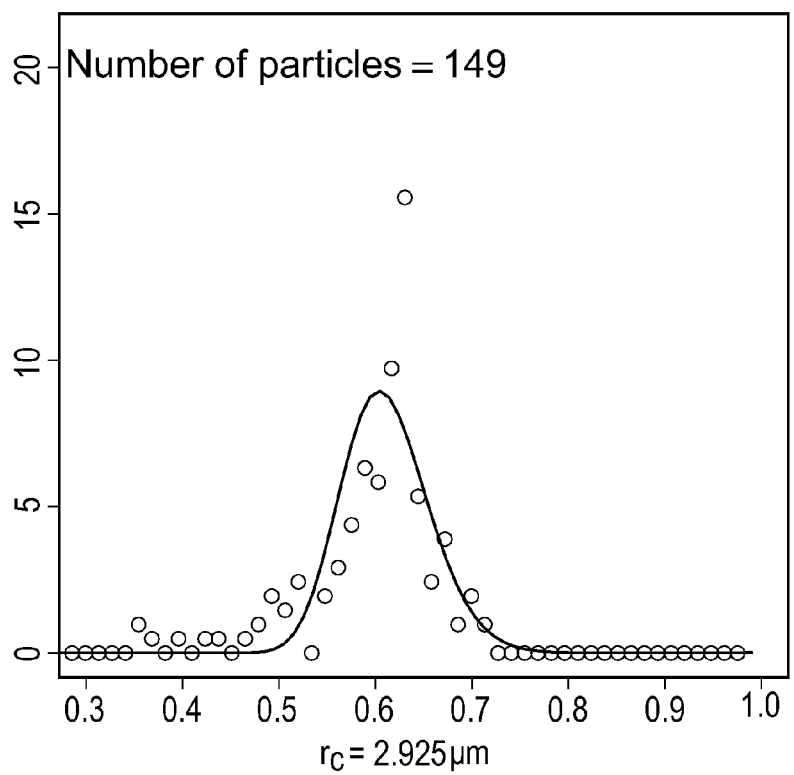
Figure 8K:
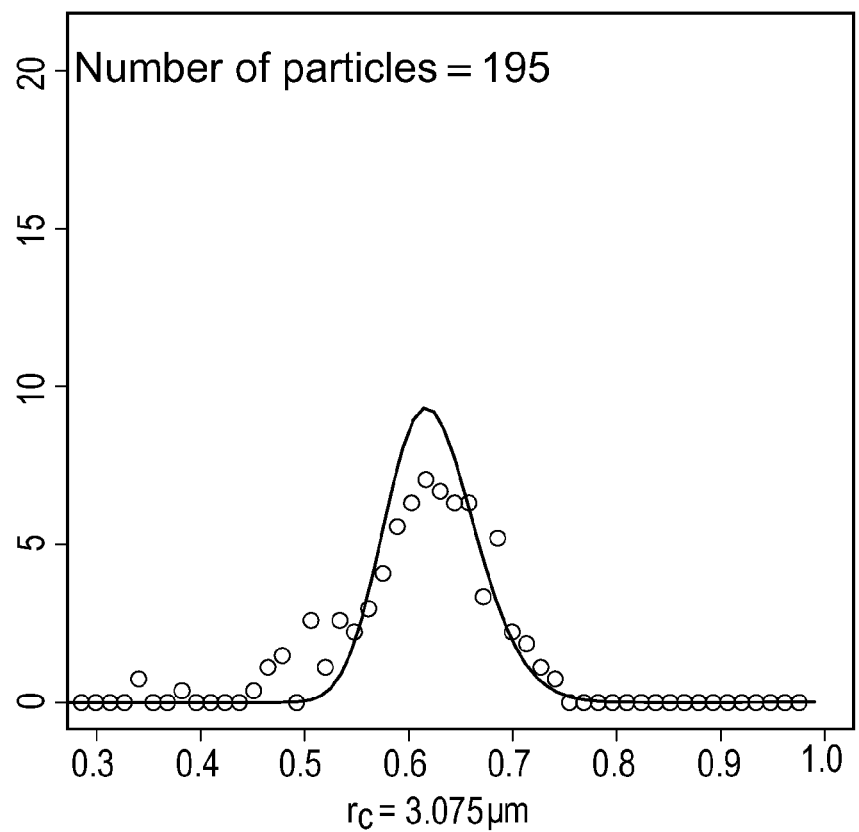
Figure 8L:
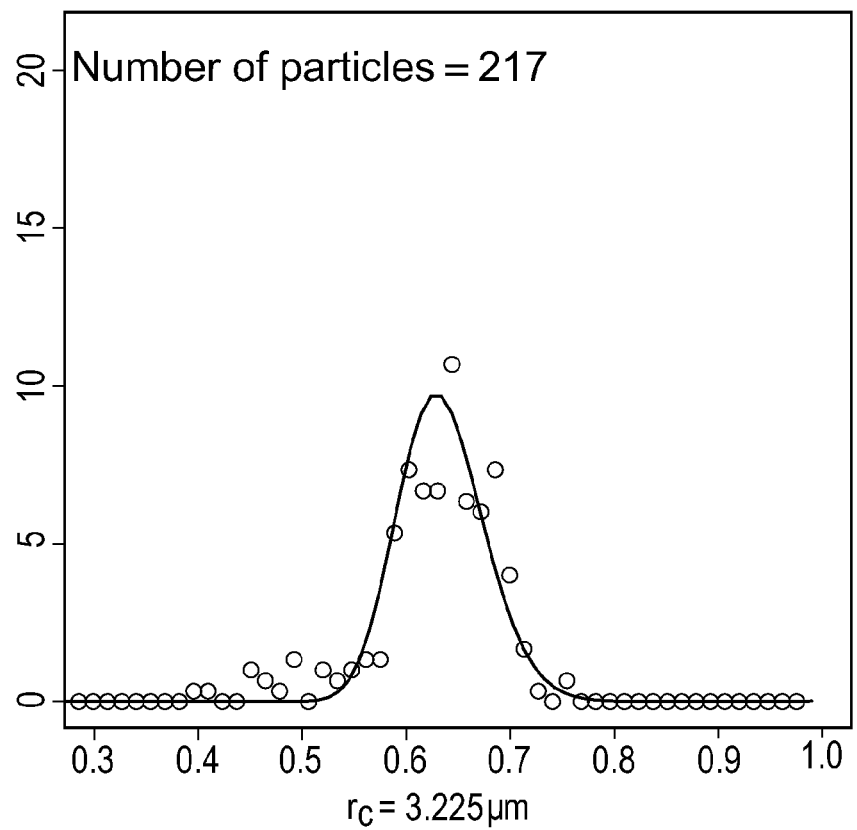
Figure 8M:
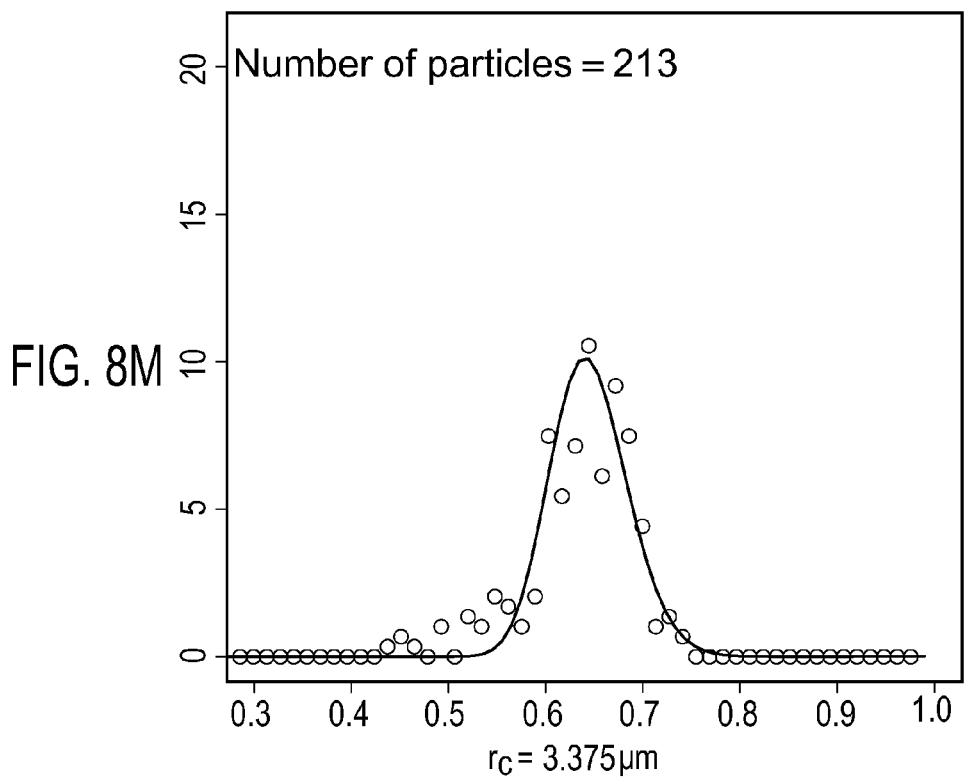
Figure 8N:
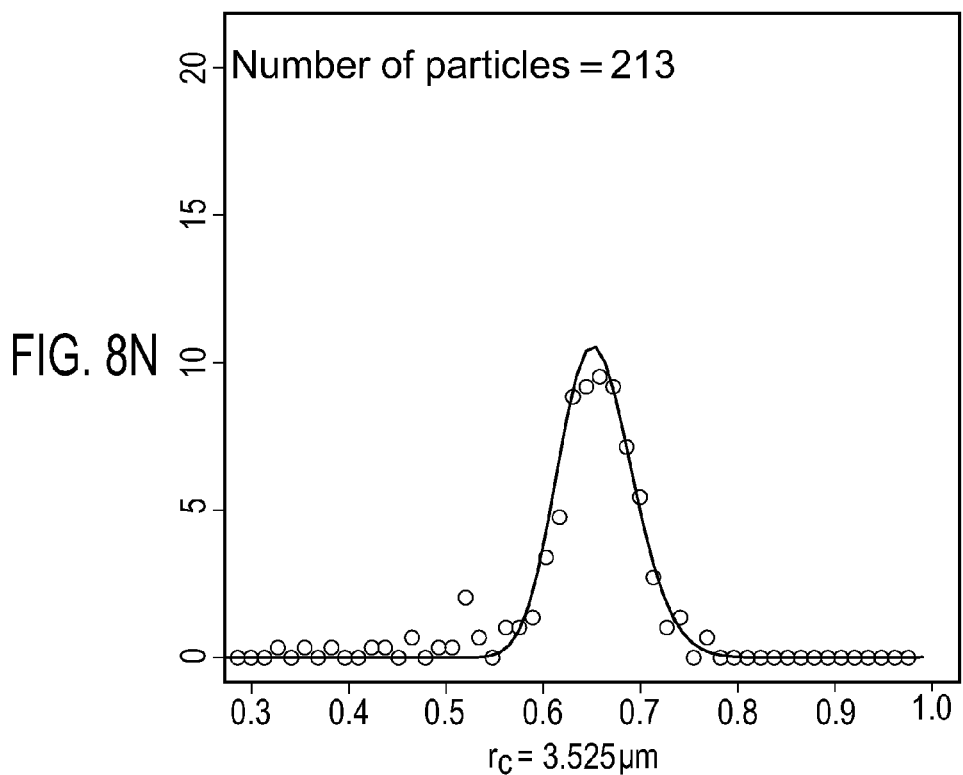
Figure 8O:
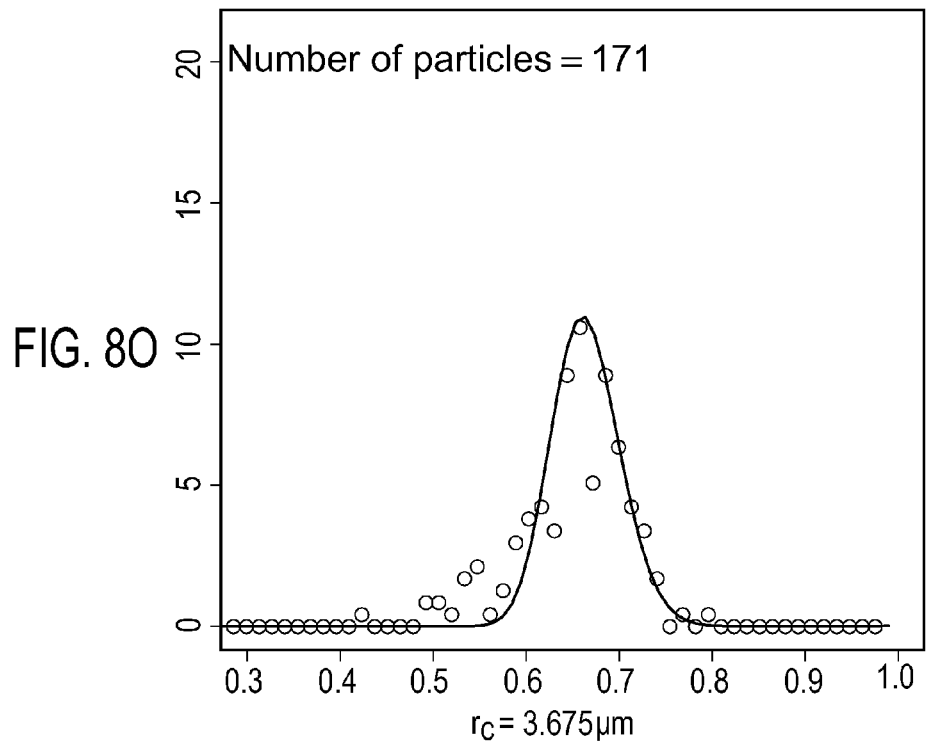
Figure 8P:
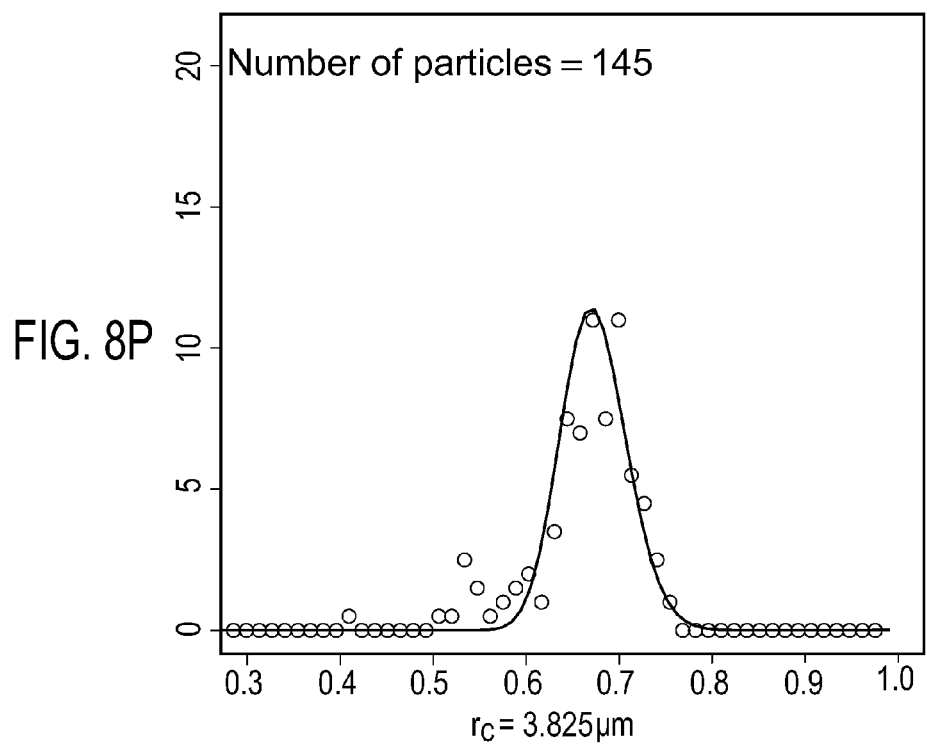
Figure 8Q:
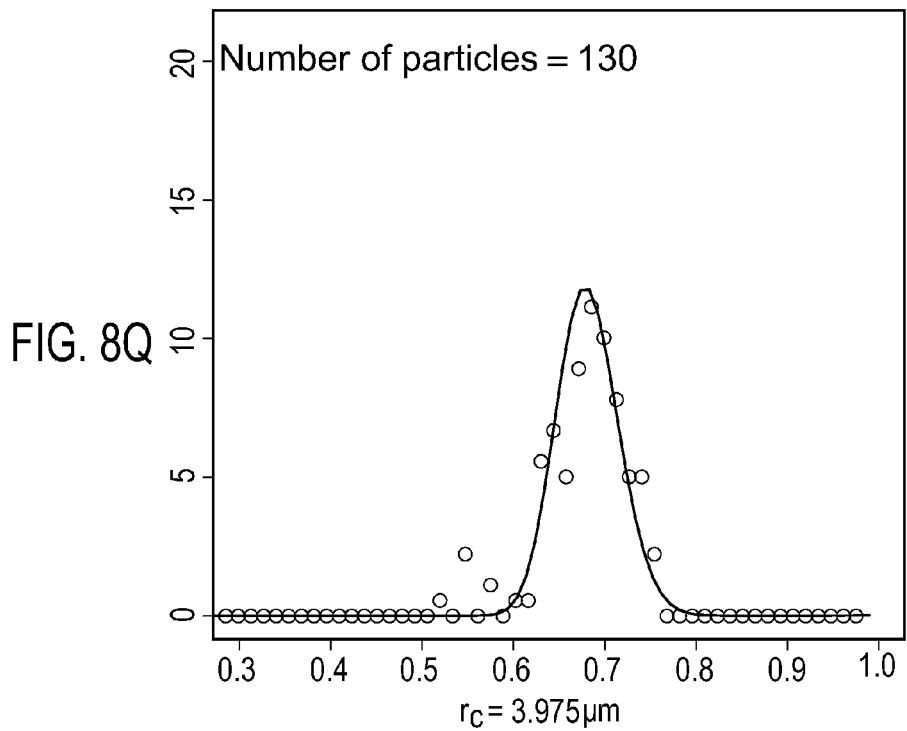
Figure 8R:
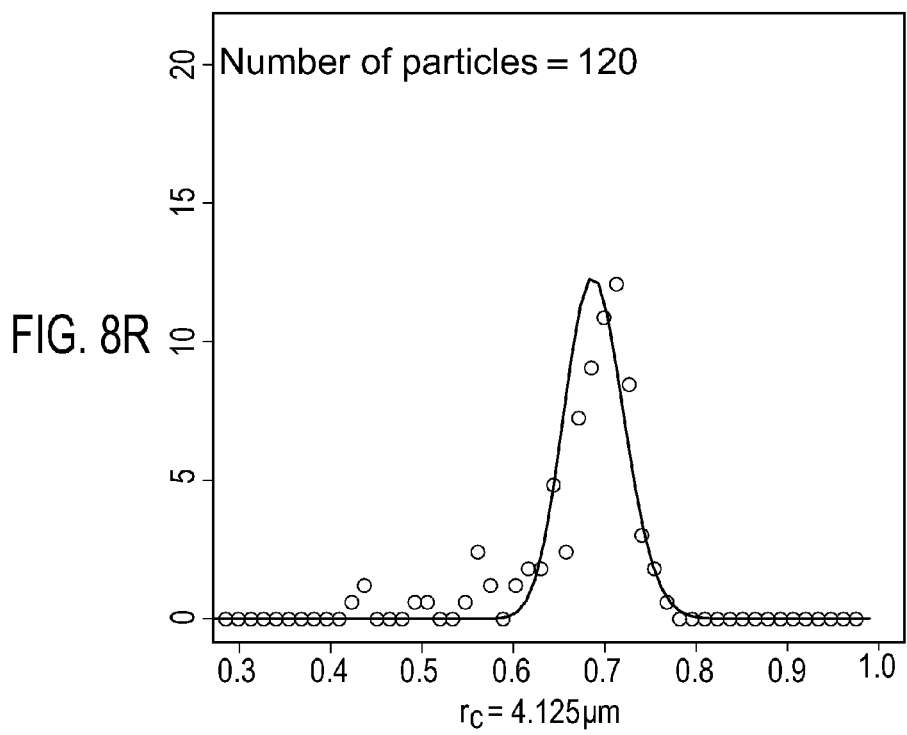
Figure 8S:
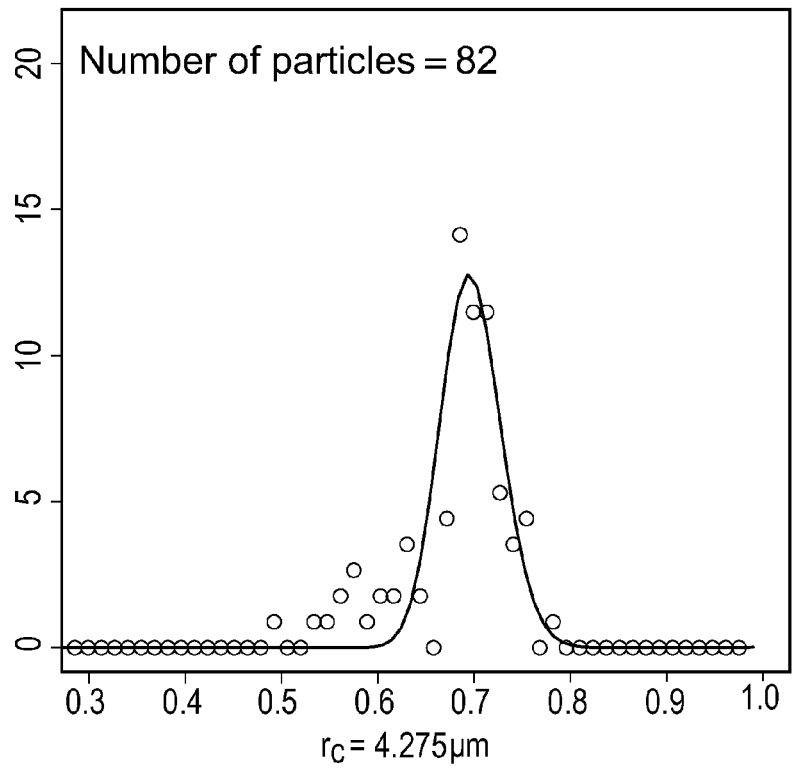
Figure 8T:
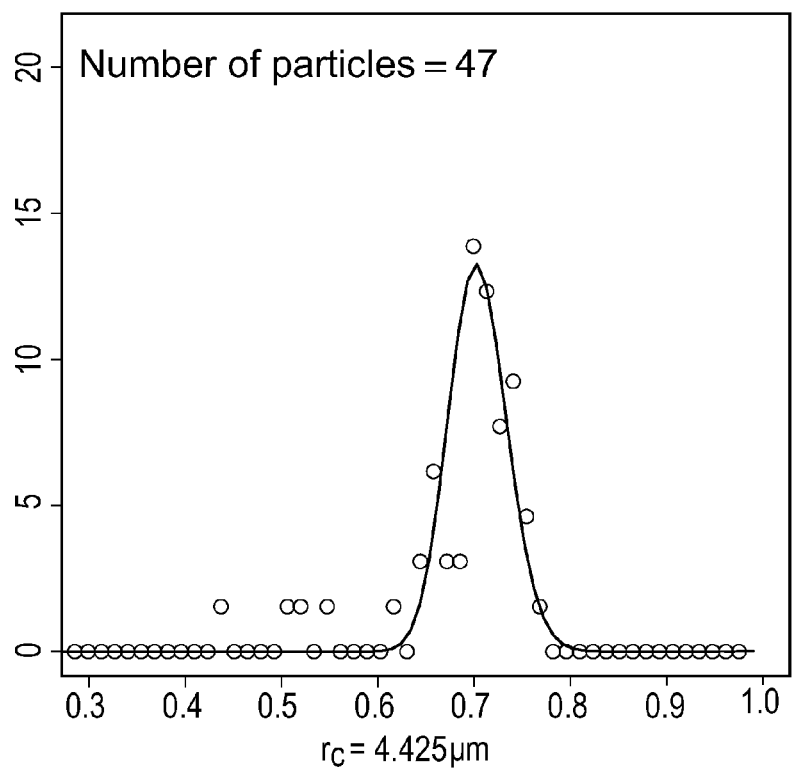
Figure 8U:
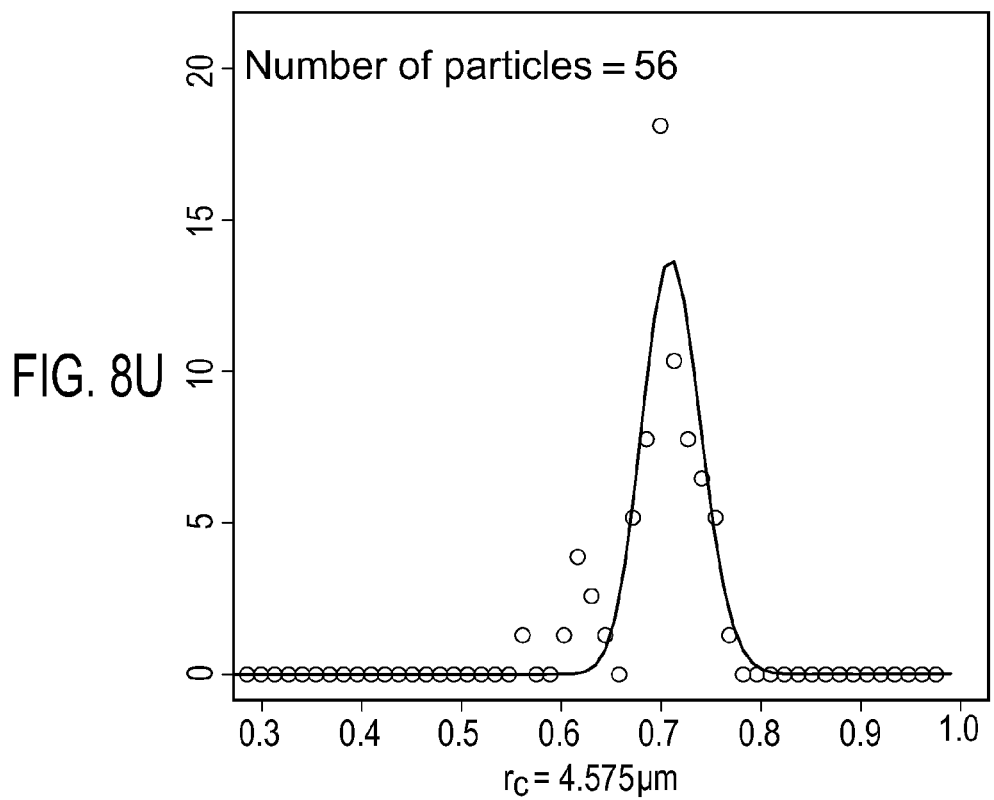
Figure 8V:
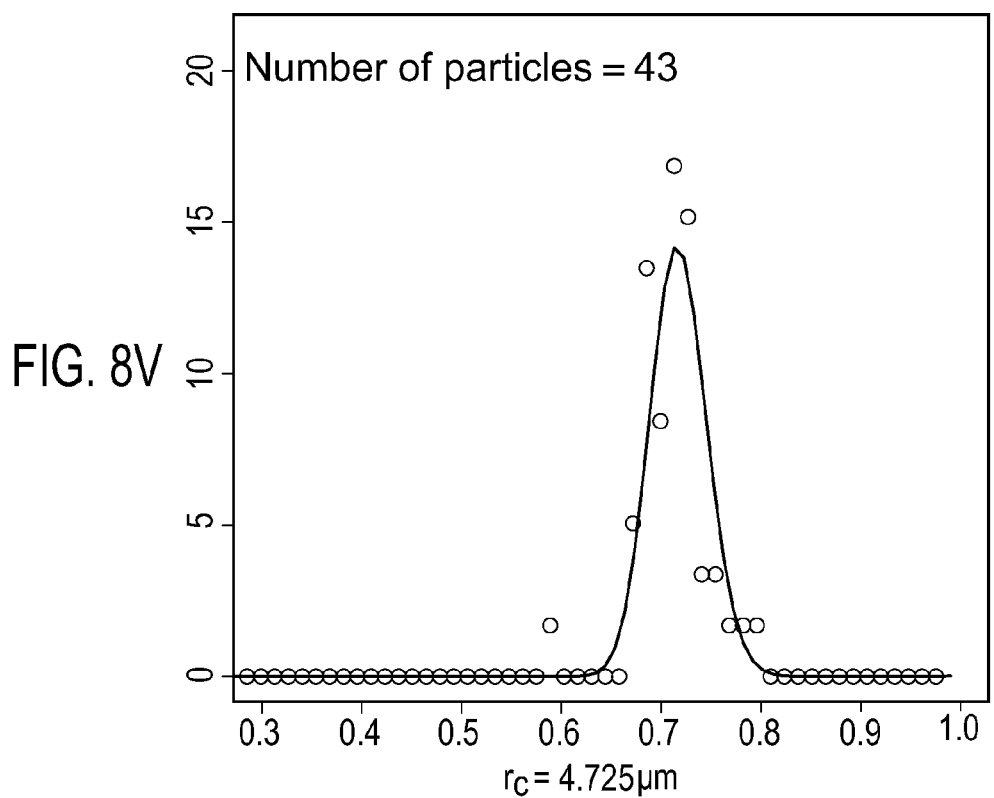
Figure 8W:
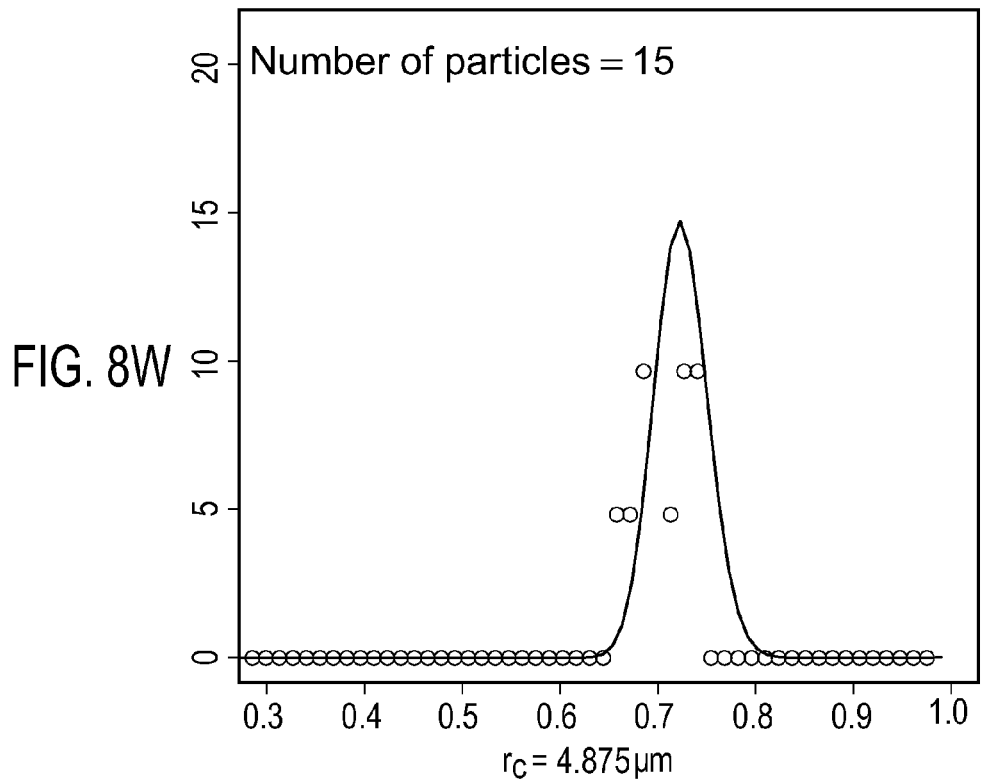
Figure 8X:
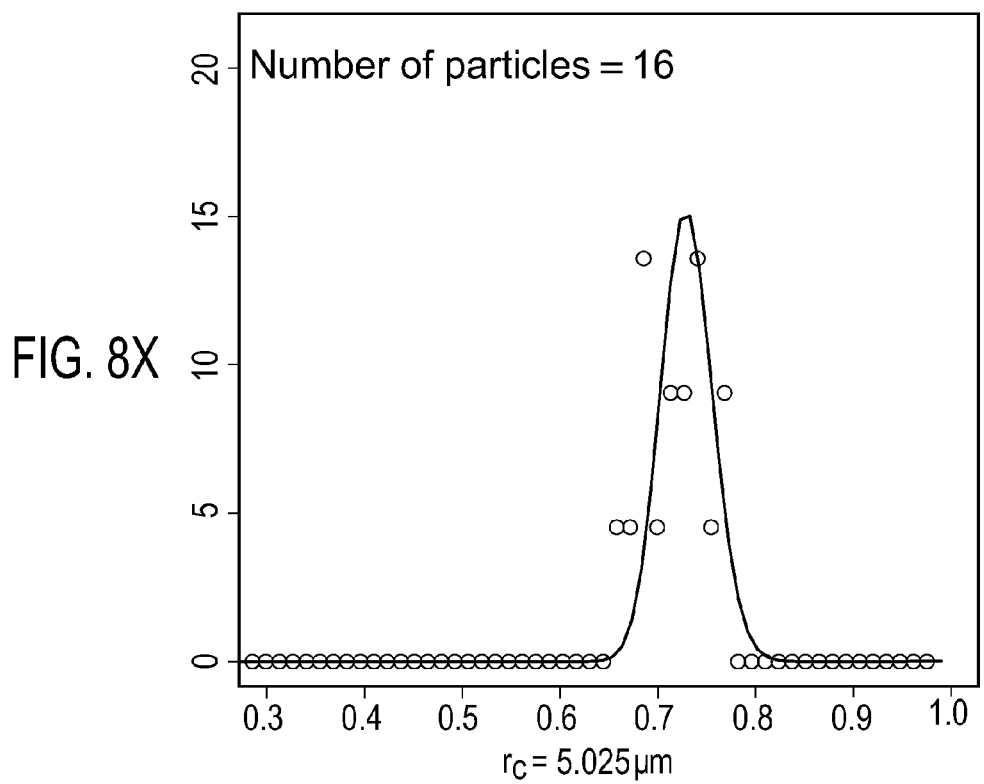
Figure 8Y:
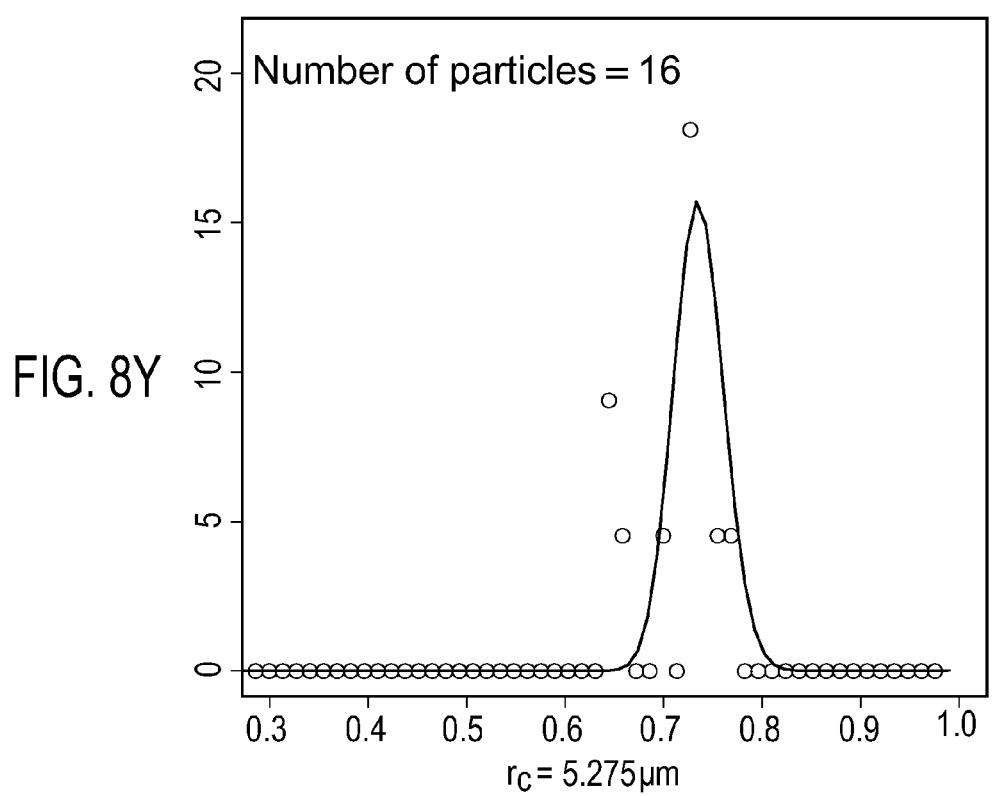

The results presented in FIGS. 3A-3D show that the averaged distributions computed using the model agree with the experiment. A more detailed test of this agreement with the experiment is to compare the conditional probabilities with experimental results, to see if the model captures the dependence on the central particle radius. These comparisons are presented in FIGS. 5-7. Experimental data is plotted as circles, whose area is proportional to the number of observations. These circles are overplotted on a grayscale map of probability obtained from the model. It can be seen that the model quantitatively captures the dependence of $r_c$ for the local packing fraction (FIG. 5), the number of neighbours (FIG. 6) and the number of contacts (FIG. 7). In addition, we show the probability distributions for each given radius $r_c$ in the gallery of graphs in FIGS. 8A-10Y for a more detailed comparison. Due to the broad radius distribution of the emulsion droplets, some of the histograms lack statistics, nevertheless, the trends are successfully reproduced.

The experimental samples we studied all present similar particle size distributions. In order to investigate the behaviour of our model for other distributions, we use numerical simulations to create jammed packings for controlled particle size distributions, using the well known LAMMPS molecular dynamics simulations. These packings were analyzed in the same way as experimental ones, and compared with the model calculations.

Log-normal distributions offer a good statistical description of many polydisperse emulsions:

$$P(r) = \frac{1}{r\sigma\sqrt{2\pi}} \exp\left[-\frac{(\ln r - \mu)^2}{2\sigma^2}\right]$$

For a fixed value of $\mu=1$, we created four jammed packings for increasing values of $\sigma$, thus changing the polydispersity of the packing. Table 1 presents the value of $\langle \Omega_{max} \rangle$ and $\langle p \rangle$ obtained for the different packings. These values clearly show that the set of parameters that characterize a packing weakly depends on the polydispersity. Note, however, that this variation is rather small, so that to a first approximation a reasonable description of the packing may be obtained by assuming the experimentally obtained values.

FIGS. 11A-11L present the comparison of the model and simulations for four different log-normal distributions with increasing variance. While the overall agreement is good, one can see that the model does not accurately predict the neighbour distribution when the sample is close to monodisperse. While the simulations exhibit a distribution of neighbours with a finite width, the model predicts a delta function. The proposed model is able to describe a polydisperse packing once the local source of randomness (poly-dispersity) dominates the non-local one, coming from the long-range positional disorder. The neighbour distributions in all cases are fit to a high degree of accuracy, while the contact distributions show discrepancies when describing the mechanically unstable rattlers. This discrepancy may be a result of the protocol used to create the simulated packings, as we did not observe the same discrepancy in the experimental packings.

We performed conventional numerical simulations for Gaussian distribution of sizes:

$$P(r) = \frac{1}{\sqrt{2\pi}\sigma} \exp\left(-\frac{(r-\mu)^2}{2\sigma^2}\right)$$

Such distributions are parameterized by $\eta=\sigma/\mu$. Results presented in FIGS. 12A-12D correspond to $\eta=1$, 0.28, to allow for a comparison with prior art known results. Numerical simulations show excellent agreement with model predictions for both radii distributions and also capture the distributions presented in the literature.

For practical purposes, such as optimizing the packing fraction by choosing the radius distribution (as is of interest to paint manufacturers) there exist a set of reasonable assumptions that yield realistic predictions. First, assume that both $\Omega_{max}(r)$ and $p(r)$ are independent of r. Next, choose a value of $\Omega_{max}$ slightly less than $4\mu$ to account for the presence of steric effects (e.g. $3:68\mu$). Then it follows that $\langle n \rangle \cong \Omega_{max}/\langle w \rangle$, where $\langle w \rangle = \int dr dr_c w(r,r_c) P(r) P(r_c)$. Finally, assuming that a static packing is close to isostaticity, $\langle z \rangle \cong 6$ and $p \cong 6/\langle n \rangle$. In this way, the model can be exploited to make predictions about packings for a given distribution of particle sizes. This recipe will provide a good starting point for any experimental exploration. Using the bidisperse packings, we demonstrated that such an approximate method yielded good quantitative agreement with measured trends in the density dependence on the size ratio and the volume fraction of small particles.

The foregoing description of embodiments of the present invention have been presented for purposes of illustration and description. It is not intended to be exhaustive or to limit the present invention to the precise form disclosed, and modifications and variations are possible in light of the above teachings or may be acquired from practice of the present invention. The embodiments were chosen and described in order to explain the principles of the present invention and its practical application to enable one skilled in the art to utilize the present invention in various embodiments, and with various modifications, as are suited to the particular use contemplated.

What is claimed is:

1. A method for determining a packing property and characteristic properties of a material having a particulate composition and processing data characteristic of the particulate composition to enable accomplishing at least one of a physical or chemical change of the composition, displaying the properties for use, printing out characteristics of the material for action using the particulate composition and storing the properties for future use of the characteristics of the particulate composition, comprising the steps of:
    obtaining data about characteristics of the particulate composition for the material;
    analyzing the data, using a computer system having a non-transitory computer readable medium, to obtain radius and position information for the particulate composition from the data;
    using the computer system for determining contact information from the radius and position information; and
    using the computer system for determining a packing property from the radius and position information and the contact information;
    using the computer system for determining characteristic properties of the particulate composition and to enable use of the determined characteristic properties to act on those properties to carry out processing of the particulate composition of the material to accomplish at least one of a physical or chemical change of the composition, displaying the properties for use of the material, printing out the characteristics of the material for user action on the material and storing the characteristic properties for future user application of the material having selected ones of the characteristic properties.

2. The method as defined in claim 1 wherein the data comprises image data obtained by the step of using an optical microscope to view the particulate composition and record the image data.

3. The method of claim 1 wherein the packing property is at least one of porosity and density.

4. The method of claim 1 wherein the radius and position information is determined by doing an analytical walk around a representative particle of the particulate composition, the analytical walk done using the computer system.

5. The method of claim 4 wherein the analytical walk comprises a random walk.

6. The method of claim 5 wherein the random walk comprises a biased random walk.

7. The method of claim 6 wherein the biased random analytical walk is performed to estimate a density fluctuation.

8. The method of claim 5 wherein the random walk comprises a one dimensional random walk.

9. The method of claim 4 wherein a number of neighbors is determined based on the analytical walk.

10. The method of claim 1 wherein the contact information is determined from the radius and position information.

11. The method of claim 10 wherein the contact information comprises number of particle neighbors that are also contacts.

12. The method of claim 10 wherein the contact information is determined using a binomial choice among the particle neighbors.

13. The method as defined in claim 1 wherein the particulate material is processed subsequent to determining the characteristic properties to accomplish selected commercial applications.

14. A computer readable medium for processing information to determine a packing property of a particulate material having a particulate composition and using the packing property to process the particulate material, the medium comprising, a computer software module in a computer including a non-transitory computer readable medium containing computer instructions stored therein for causing a computer processor of the computer to perform steps to operate on data characteristic of the particulate material; and the set of instructions being executed by the computer processor to carry out the steps of:

(i) obtaining size information relating to the particulate material;

(ii) determining neighbor information from the size information;

(iii) determining contact information from the size information; and (iv) determining a packing property from the neighbor information and the contact information thereby enabling determination of characteristic properties of the particulate material; and (v) using the characteristic properties to process data characteristic of the particulate material and the particulate composition to enable accomplishing at least one of a physical or chemical change of at least one of the articulate composition or the articulate material, displaying the characteristic properties for user action and utilization of the particulate material, printing out characteristics of the particulate material for user action using a selected particulate material and storing the characteristic properties for future use in processing the particulate material having selected ones of the characteristic properties.

15. The computer readable medium of claim 14 wherein the characteristic properties are at least one of: (a) stored in a computer-accessible storage medium; and (b) provided for display.

16. The computer readable medium of claim 14 wherein the characteristic properties are at least one of porosity and density.

17. The computer readable medium of claim 14 wherein the neighbor information is determined by doing an analytical walk around a representative particle of the particulate composition.

18. The computer readable medium of claim 17 wherein the analytical walk comprises a random walk.

19. The computer readable medium of claim 18 wherein the random walk comprises a biased random walk.

20. The computer readable medium of claim 19 wherein a biased random walk is performed to estimate a density fluctuations.

* * * * *